United States Patent
Lee et al.

(10) Patent No.: US 9,520,567 B2
(45) Date of Patent: *Dec. 13, 2016

(54) LUMINESCENT MATERIAL FOR ORGANIC OPTOELECTRIC DEVICE AND ORGANIC OPTOELECTRIC DEVICE AND DISPLAY DEVICE

(71) Applicant: CHEIL INDUSTRIES INC., Gumi-si, Gyeongsangbuk-do (KR)

(72) Inventors: Han-Ill Lee, Suwon-si (KR); Eun-Sun Yu, Suwon-si (KR); Dong-Min Kang, Suwon-si (KR); Eui-Su Kang, Suwon-si (KR); Yong-Tak Yang, Suwon-si (KR); Jae-Jin Oh, Suwon-si (KR); Dong-Kyu Ryu, Suwon-si (KR); Sang-Shin Lee, Suwon-si (KR); Yu-Na Jang, Suwon-si (KR); Soo-Young Jeong, Suwon-si (KR); Su-Jin Han, Suwon-si (KR); Jin-Seok Hong, Suwon-si (KR)

(73) Assignee: CHEIL INDUSTRIES, INC., Gumi-si, Gyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/760,154

(22) PCT Filed: Sep. 25, 2013

(86) PCT No.: PCT/KR2013/008584
§ 371 (c)(1),
(2) Date: Jul. 9, 2015

(87) PCT Pub. No.: WO2014/185595
PCT Pub. Date: Nov. 20, 2014

(65) Prior Publication Data
US 2015/0340618 A1    Nov. 26, 2015

(30) Foreign Application Priority Data

May 16, 2013 (KR) .................. 10-2013-0055939

(51) Int. Cl.
*H01L 51/00* (2006.01)
*C07D 251/24* (2006.01)
(Continued)

(52) U.S. Cl.
CPC ......... *H01L 51/0054* (2013.01); *C07D 213/06* (2013.01); *C07D 213/16* (2013.01);
(Continued)

(58) Field of Classification Search
CPC ............ H01L 51/0054; H01L 51/0067; H01L 51/5012; H01L 2251/552; C09B 57/00; C07D 401/14; C07D 401/04; C07D 213/06; C07D 213/16; C07D 239/26; C07D 213/22; C07D 251/24; C09K 11/06; C09K 2211/1007
See application file for complete search history.

(56) References Cited

FOREIGN PATENT DOCUMENTS

| CN | 101203583 A | 6/2008 |
|---|---|---|
| CN | 102532105 A | 7/2012 |

(Continued)

OTHER PUBLICATIONS

Search Report mailed Apr. 13, 2015 in corresponding Taiwanese Patent Application No. 103109224.
Search Report mailed Jun. 7, 2016 in corresponding Chinese Patent Application No. 201380074818.1.

*Primary Examiner* — Michelle Mandala
(74) *Attorney, Agent, or Firm* — Lee & Morse, P.C.

(57) ABSTRACT

Disclosed are a luminescent material for an organic optoelectric device represented by Chemical Formula 1, an organic optoelectric device including the luminescent material for an organic optoelectric device, and a display device including the organic optoelectric device.

13 Claims, 1 Drawing Sheet

(51) Int. Cl.

| | |
|---|---|
| *C09K 11/06* | (2006.01) |
| *C07D 401/14* | (2006.01) |
| *C07D 401/04* | (2006.01) |
| *C07D 239/26* | (2006.01) |
| *C07D 213/06* | (2006.01) |
| *C07D 213/16* | (2006.01) |
| *C07D 213/22* | (2006.01) |
| *C09B 57/00* | (2006.01) |
| *H01L 51/50* | (2006.01) |

(52) U.S. Cl.
CPC ......... *C07D 213/22* (2013.01); *C07D 239/26* (2013.01); *C07D 251/24* (2013.01); *C07D 401/04* (2013.01); *C07D 401/14* (2013.01); *C09B 57/00* (2013.01); *C09K 11/06* (2013.01); *H01L 51/0067* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/185* (2013.01); *H01L 51/0081* (2013.01); *H01L 51/0085* (2013.01); *H01L 51/5012* (2013.01); *H01L 51/5016* (2013.01); *H01L 2251/552* (2013.01); *Y02E 10/549* (2013.01)

(56) References Cited

FOREIGN PATENT DOCUMENTS

| | | |
|---|---|---|
| CN | 102858913 A | 1/2013 |
| JP | 2005-276801 A | 10/2005 |
| JP | 2008-094910 A | 4/2008 |
| JP | 2012-059904 A | 3/2012 |
| JP | 2012-216819 A | 11/2012 |
| KR | 10-2010-0063713 A | 6/2010 |
| KR | 10-2011-0041729 A | 4/2011 |
| KR | 10-2011-0077821 A | 7/2011 |
| KR | 10-2011-0115887 A | 10/2011 |
| KR | 10-2011-0123172 A | 11/2011 |
| KR | 10-2011-0130904 A | 12/2011 |
| KR | 10-2012-0116282 A | 10/2012 |
| KR | 10-1218029 B1 | 1/2013 |
| TW | 201240989 A | 10/2012 |
| TW | 201444951 A | 12/2014 |
| WO | WO 2006/130598 A2 | 12/2006 |
| WO | WO 2007-029696 A1 | 3/2007 |
| WO | WO 2009/021107 A1 | 2/2009 |
| WO | WO 2011/137157 A1 | 11/2011 |
| WO | WO 2012/048781 A1 | 4/2012 |
| WO | WO 2012/087960 A1 | 6/2012 |
| WO | WO 2012/133652 A1 | 10/2012 |

LUMINESCENT MATERIAL FOR ORGANIC OPTOELECTRIC DEVICE AND ORGANIC OPTOELECTRIC DEVICE AND DISPLAY DEVICE

CROSS REFERENCE TO RELATED APPLICATIONS

This is the U.S. national phase application based on PCT Application No. PCT/KR2013/008584, filed Sep. 25, 2013, which is based on Korean Patent Application No. 10-2013-0055939, filed May 16, 2013, the entire contents of all of which are hereby incorporated by reference.

TECHNICAL FIELD

A luminescent material for an organic optoelectric device, an organic optoelectric device, and a display device are disclosed.

BACKGROUND ART

An organic optoelectric device is a device that converts electrical energy into photoenergy, and vice versa.

An organic optoelectric device may be classified as follows in accordance with its driving principles. One is an electronic device where excitons generated by photoenergy are separated into electrons and holes and the electrons and holes are transferred to different electrodes respectively and electrical energy is generated, and the other is a light emitting device to generate photoenergy from electrical energy by supplying a voltage or a current to electrodes.

Examples of the organic optoelectric device include an organic photoelectric device, an organic light emitting diode, an organic solar cell, and an organic photo-conductor drum, and the like.

Among them, the organic light emitting diode (OLED) has recently drawn attention due to an increase in demand for flat panel displays. The organic light emitting diode converts electrical energy into light by applying current to an organic light emitting material, and has a structure in which an organic layer is interposed between an anode and a cathode. Herein, the organic layer may include an emission layer, and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and/or stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides a luminescent material for an organic optoelectric device capable of realizing an organic optoelectric device having high efficiency and long lifespan.

Another embodiment provides an organic optoelectric device including the luminescent material for an organic optoelectric device.

Yet another embodiment provides a display device including the organic optoelectric device.

Technical Solution

According to one embodiment, a luminescent material for an organic optoelectric device represented by the Chemical Formula 1 is provided.

[Chemical Formula 1]

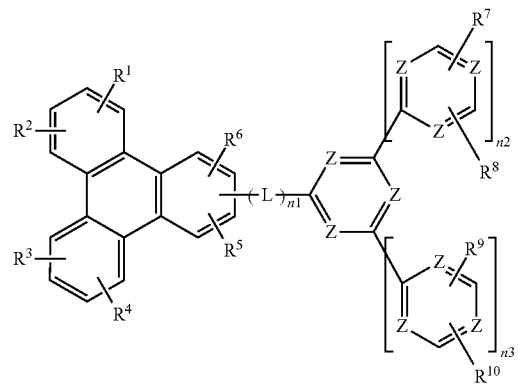

In the Chemical Formula 1,

Z is each independently N or $CR^a$, at least one of Z is N, $R^1$ to $R^{10}$ and $R^a$ are each independently hydrogen, deuterium, a substituted or unsubstituted C1 to C10 alkyl group, a substituted or unsubstituted C6 to C12 aryl group, or a combination thereof, L is a substituted or unsubstituted phenylene group, a substituted or unsubstituted biphenylene group or a substituted or unsubstituted terphenylene group, n1 to n3 are each independently 0 or 1, and n1+n2+n3≥1.

According to another embodiment, an organic optoelectric device includes an anode and a cathode facing each other, and an emission layer interposed between the anode and the cathode and including the luminescent material for an organic optoelectric device.

According to yet another embodiment, a display device including the organic optoelectric device is provided.

Advantageous Effects

The luminescent material for an organic optoelectric device according to the embodiment is an organic compound having bipolar characteristics including a substituent having electron characteristics being capable of accepting electrons well and a triphenylene group being capable of accepting holes well. The organic compound may receive electrons and holes well and thus may be used in a light emission directly and easily transfer these to a dopant. Therefore, the luminescent material according to the embodiment may realize high performance when it is used in an emission layer of an organic optoelectric device.

BEST MODE

Figure 1:
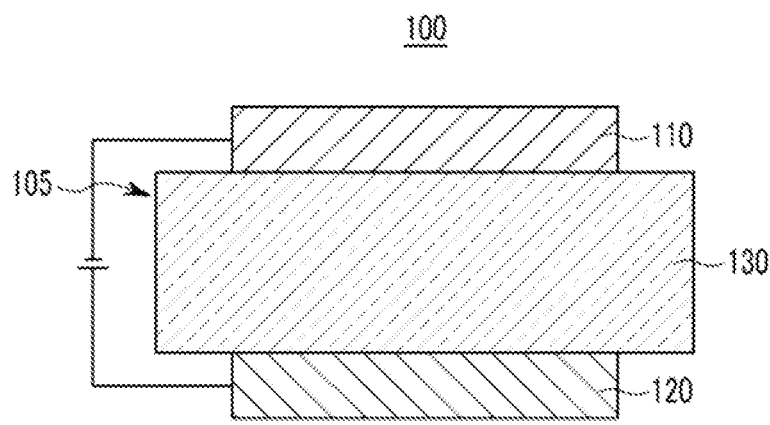
FIGS. 1 and 2 are cross-sectional views of each organic light emitting diode according to one embodiment.

Hereinafter, embodiments of the present invention are described in detail. However, these embodiments are exemplary, and this disclosure is not limited thereto.

As used herein, when a definition is not otherwise provided, the term "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, and the like, or a cyano group, instead of at least one hydrogen of a substituent or a compound.

In addition, two adjacent substituents among the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as trifluoromethyl group may be fused with each other to form a ring. For example, the substituted C6 to C30 aryl group may be fused with another adjacent substituted C6 to C30 aryl group to form a substituted or unsubstituted fluorene ring.

In the present specification, when specific definition is not otherwise provided, the term "hetero" refers to one including 1 to 3 hetero atoms selected from N, O, S, P, and Si, and remaining carbons in one compound or substituent.

As used herein, when a definition is not otherwise provided, the term "combination thereof" refers to at least two substituents bound to each other by a linking group, or at least two substituents condensed to each other.

As used herein, when a definition is not otherwise provided, the term "alkyl group" may refer to an aliphatic hydrocarbon group. The alkyl group may refer to "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group includes 1 to 4 carbon in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

As used herein, the term "heteroaryl group" may refer to aryl group including 1 to 3 hetero atoms selected from N, O, S, P, and Si and remaining carbons in one functional group.

The heteroaryl group may be a fused ring where each ring may include the 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, but is not limited thereto.

In the specification, hole characteristics refer to characteristics capable of donating an electron to form a hole when electric field is applied, and characteristics that hole formed in the anode is easily injected into the emission layer and transported in the emission layer due to conductive characteristics according to HOMO level.

In addition, electron characteristics refer to characteristics capable of accepting an electron when electric field is applied, and characteristics that electron formed in the cathode is easily injected into the emission layer and transported in the emission layer due to conductive characteristics according to LUMO level.

Hereinafter, a luminescent material for an organic optoelectric device according to one embodiment is described.

The luminescent material for an organic optoelectric device according to one embodiment is represented by the Chemical Formula 1.

[Chemical Formula 1]

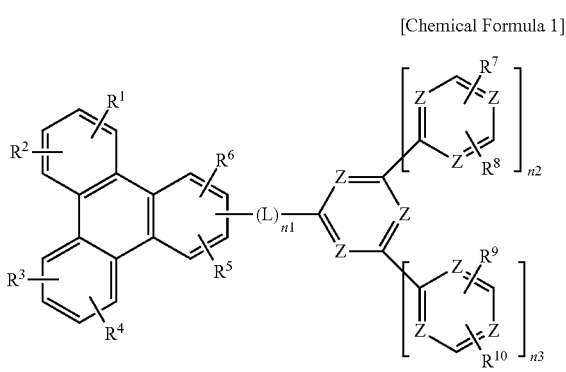

In the Chemical Formula 1,
Z is each independently N or CR$^a$,
at least one of Z is N,
R$^1$ to R$^{10}$ and R$^a$ are each independently hydrogen, deuterium, a substituted or unsubstituted C1 to C10 alkyl group, a substituted or unsubstituted C6 to C12 aryl group, or a combination thereof,
L is a substituted or unsubstituted phenylene group, a substituted or unsubstituted biphenylene group or a substituted or unsubstituted terphenylene group,
n1 to n3 are each independently 0 or 1, and
n1+n2+n3≥1.

The luminescent material may be represented by for example the Chemical Formula 1-I or 1-II, depending on the bonding position of the triphenylene group.

[Chemical Formula 1-I]

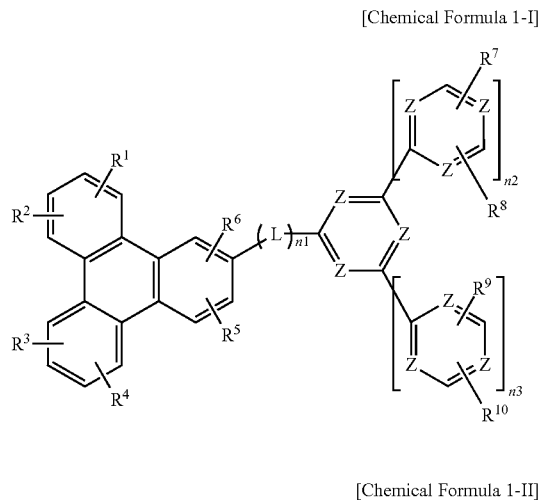

[Chemical Formula 1-II]

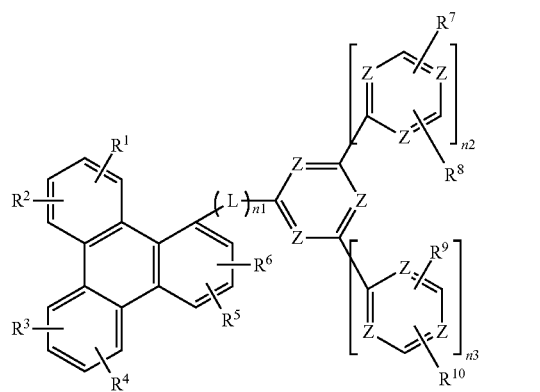

In the Chemical Formula 1-I or 1-II,
Z, R$^1$ to R$^{10}$ and R$^a$, L and n1 to n3 are the same as described above.

The luminescent material represented by the Chemical Formula 1 includes the triphenylene group and at least one nitrogen-containing heteroaryl group.

The luminescent material includes at least one nitrogen-containing ring and thereby, may have a structure of easily accepting electrons when an electric field is applied thereto and thus, decrease a driving voltage of an organic optoelectric device including the luminescent material.

In addition, the luminescent material has a bipolar structure by including both a triphenylene moiety of easily accepting holes and a nitrogen-containing ring moiety of easily accepting electrons and may appropriately balance a flow of the holes and the electrons, and accordingly, improve efficiency of an organic optoelectric device when applied thereto.

The luminescent material represented by the Chemical Formula 1 has at least one kink structure as a center of an arylene group and/or a heteroarylene group.

The kink structure is a structure that two linking parts of the arylene group and/or the heteroarylene group are not a linear structure. For example, as for phenylene, ortho phenylene (o-phenylene) and meta phenylene (m-phenylene) have the kink structure where two linking parts do not form a linear structure, while para phenylene (p-phenylene) has no kink structure because where two linking parts form a linear structure.

In the Chemical Formula 1, the kink structure may be formed as a center of a linking group (L) and/or an arylene group or a heteroarylene group.

For example, when n1 in the Chemical Formula 1 is 0, that is, there is no linking group (L), a kink structure may be formed as a center of an arylene group or a heteroarylene group, and for example, the luminescent material may be represented by the Chemical Formula 1a or 1b.

[Chemical Formula 1a]

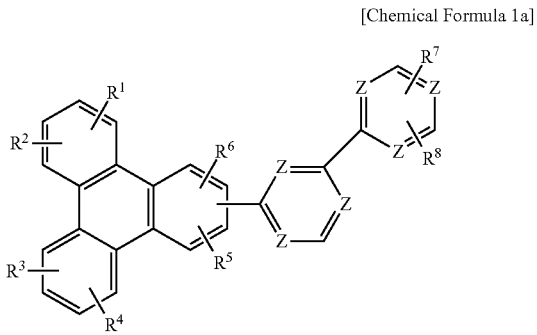

[Chemical Formula 1b]

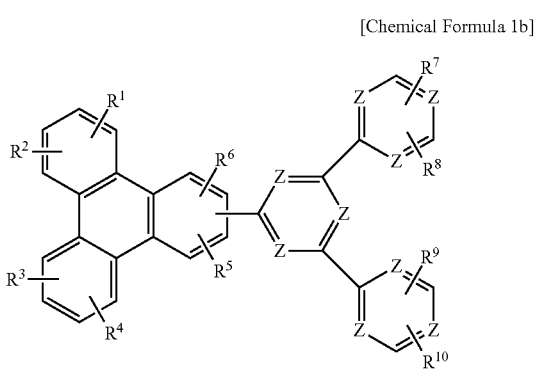

In the Chemical Formula 1a or 1 b, Z and $R^1$ to $R^{10}$ are the same as described above.

For example, when n1 in the Chemical Formula 1 is 1, a kink structure may be formed as a center of a linking group (L), and for example, the L is may be a substituted or unsubstituted phenylene having the kink structure, a substituted or unsubstituted biphenylene group having the kink structure, or a substituted or unsubstituted terphenylene group having the kink structure. The L may be selected from, for example substituted or unsubstituted groups listed in the Group 1.

[Group 1]

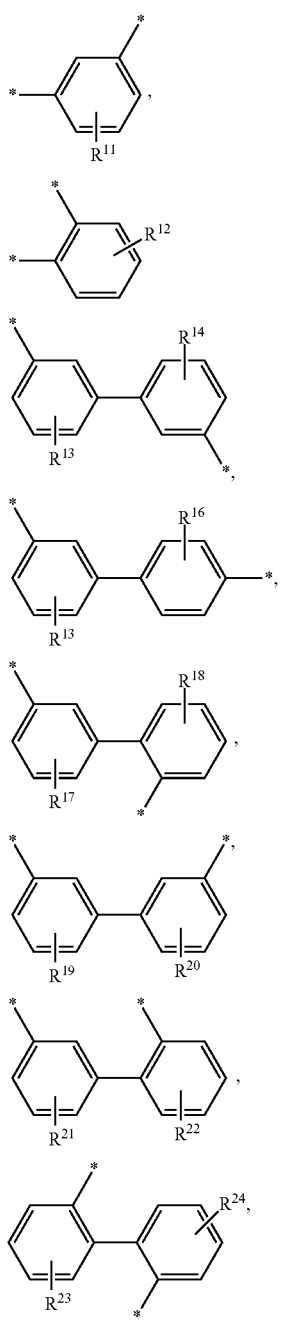

-continued

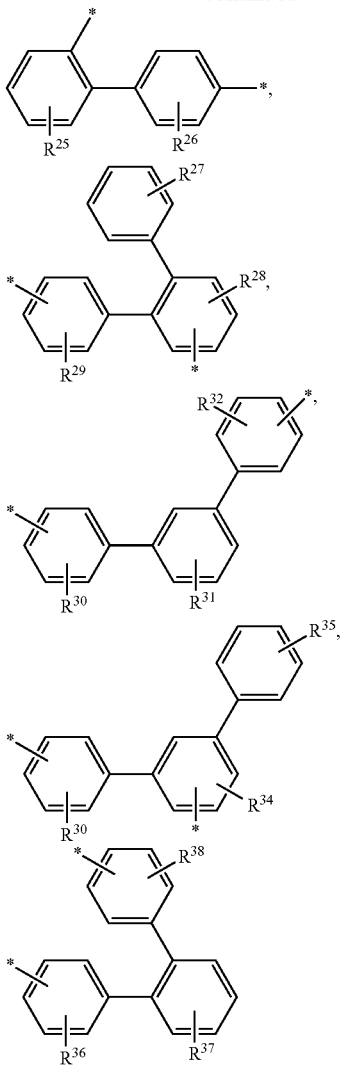

The $R^{11}$ to $R^{38}$ are independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof.

The luminescent material may have at least two kink structures and for example, two to four kink structures.

The luminescent material may appropriately localize a triphenylene moiety easily accepting a hole and a nitrogen-containing ring moiety easily accepting an electron in the compound having the bipolar structure and control a conjugation-system flow, due to the kink structure, and thus, realize improved bipolar characteristics. Accordingly, a lifespan of an organic optoelectric device including the luminescent material in an emission layer may be improved.

In addition, the luminescent material may be effectively prevented from stacking in a process and thus improve process stability and simultaneously, lower a deposition temperature. This stacking prevention effect may be further increased when the luminescent material includes the linking group (L) of the Chemical Formula 1.

The luminescent material may be, for example a compound represented by the Chemical Formulae 1c to 1t.

[Chemical Formula 1c]

[Chemical Formula 1d]

[Chemical Formula 1e]

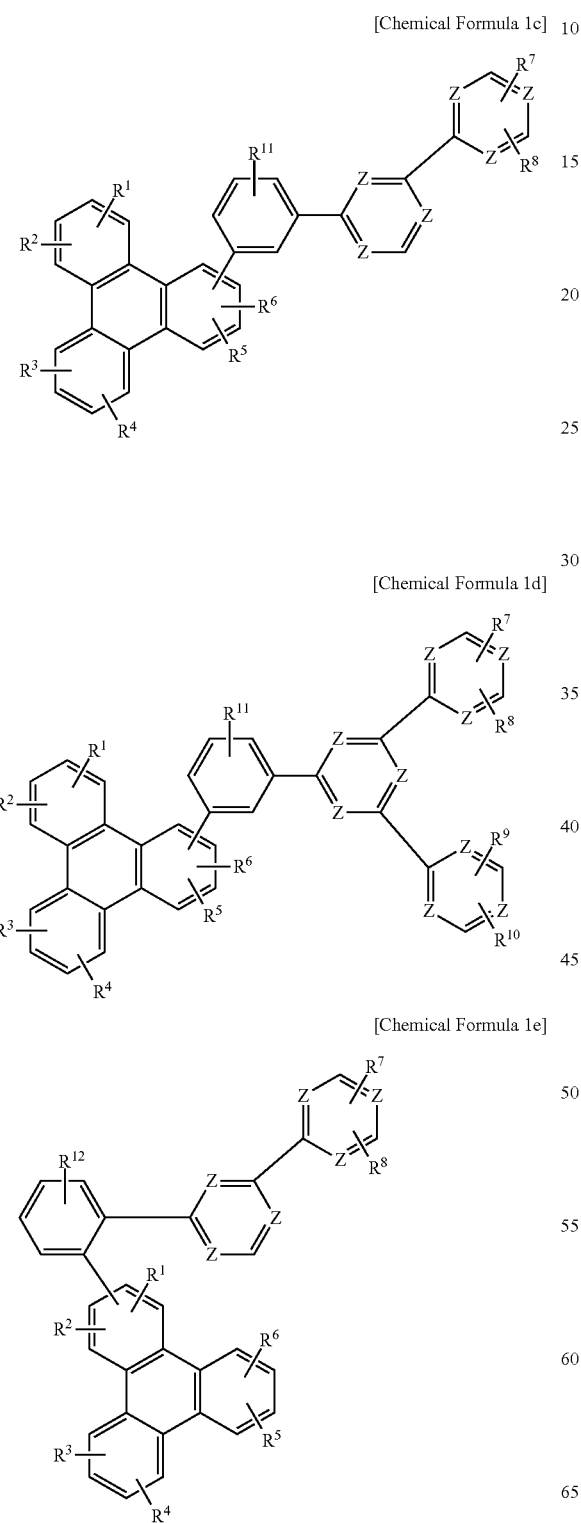

[Chemical Formula 1f]

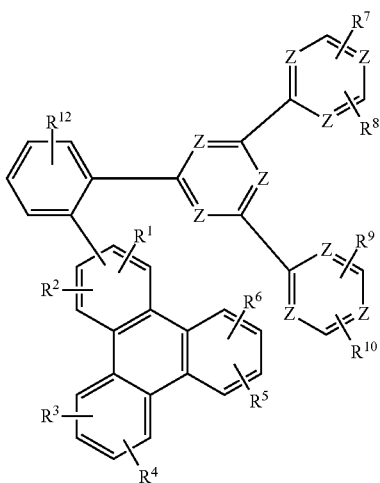

[Chemical Formula 1g]

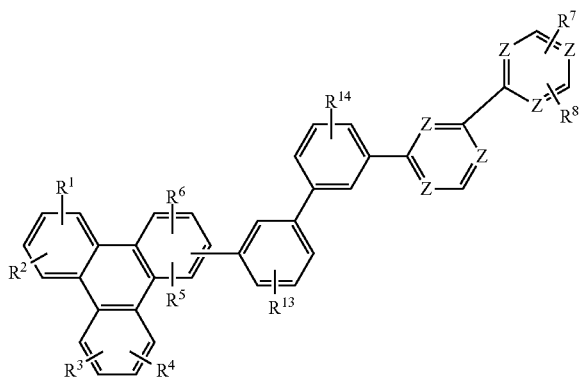

[Chemical Formula 1h]

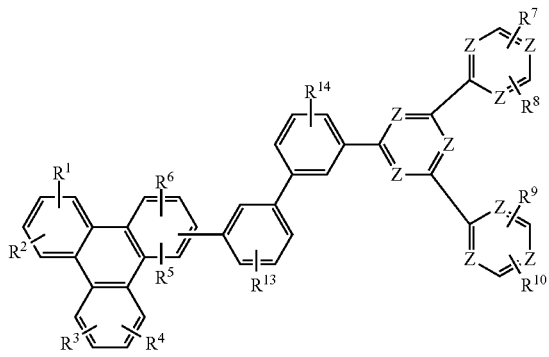

[Chemical Formula 1i]

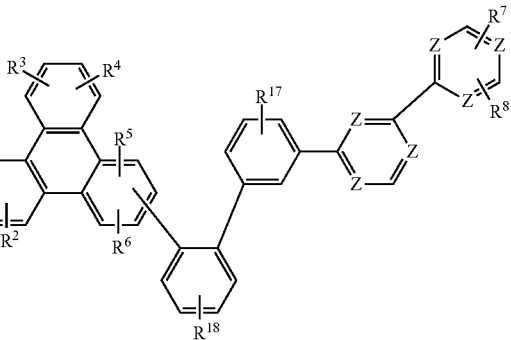

[Chemical Formula 1j]
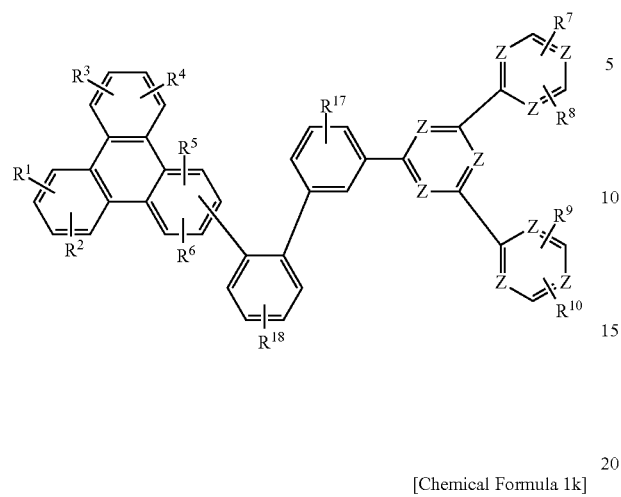
[Chemical Formula 1k]
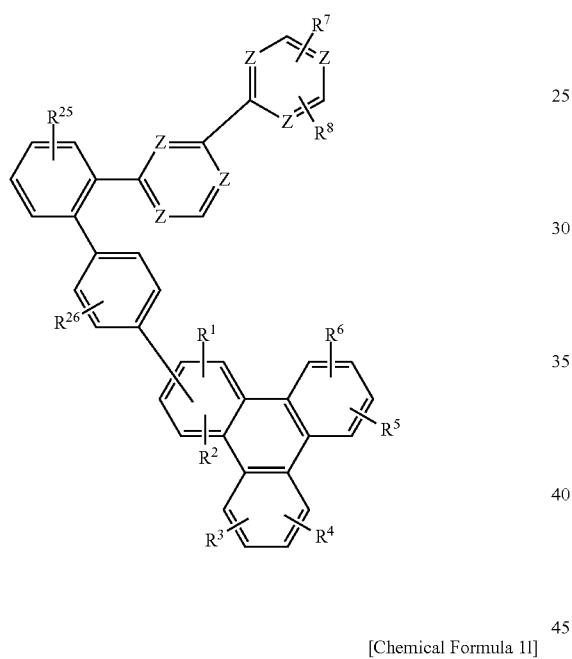
[Chemical Formula 1l]
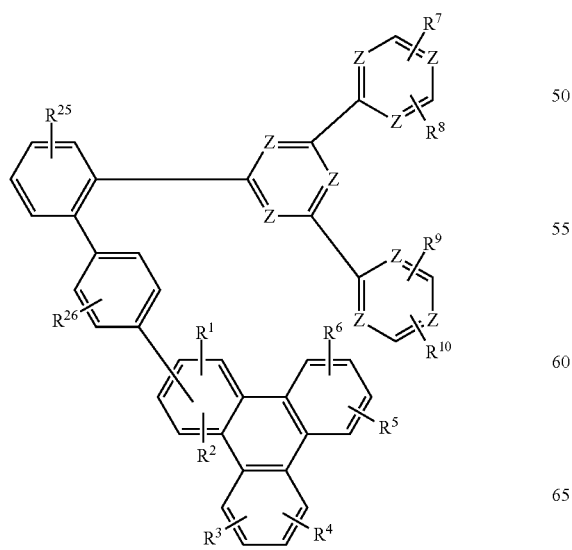
[Chemical Formula 1m]
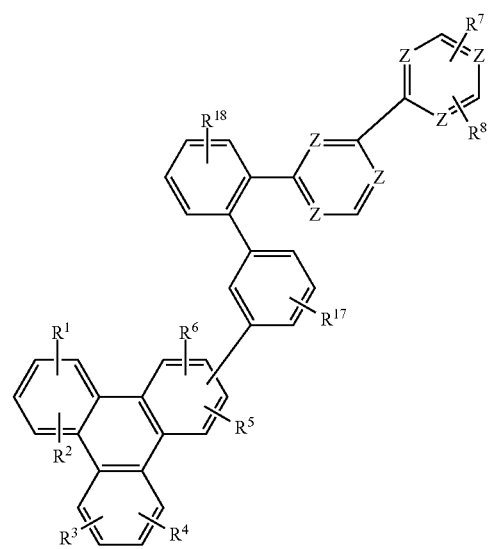
[Chemical Formula 1n]
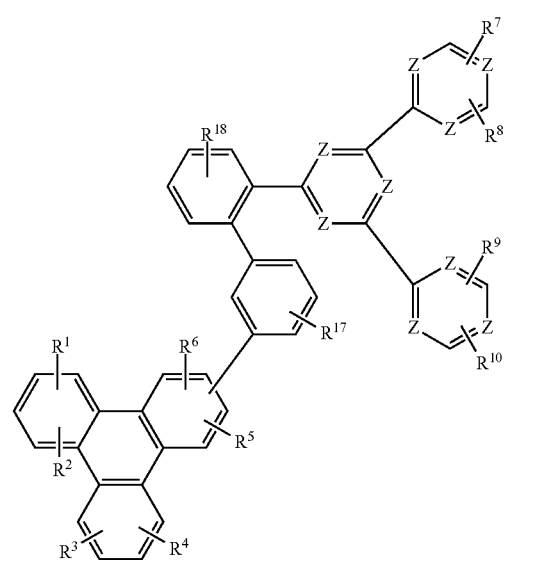
[Chemical Formula 1o]
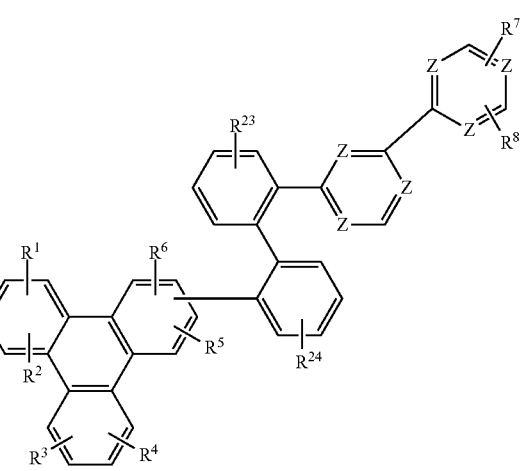

[Chemical Formula 1p]
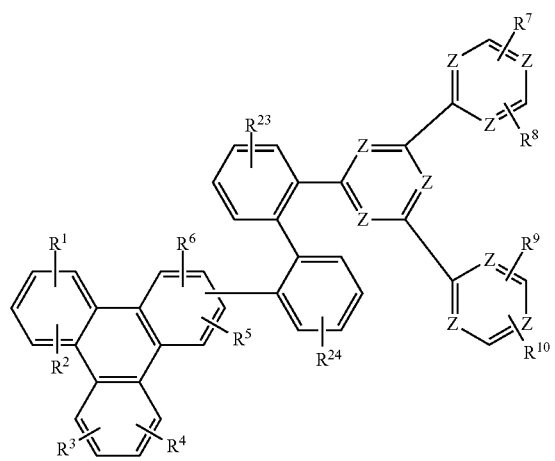
[Chemical Formula 1q]
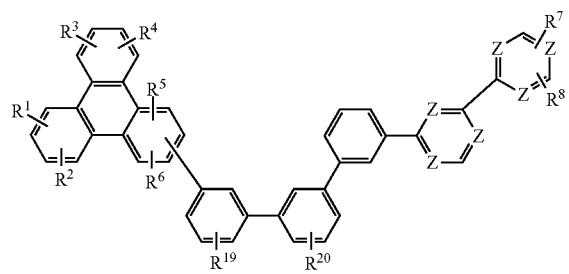
[Chemical Formula 1r]
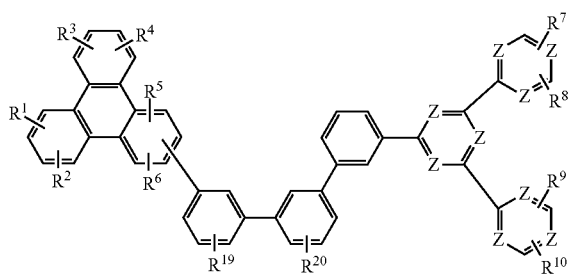
[Chemical Formula 1s]
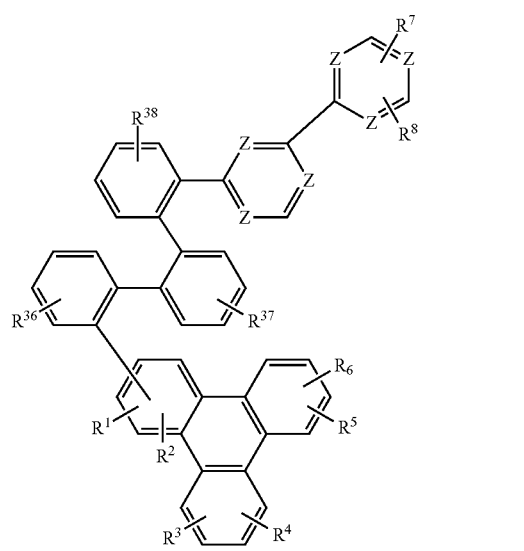
[Chemical Formula 1t]
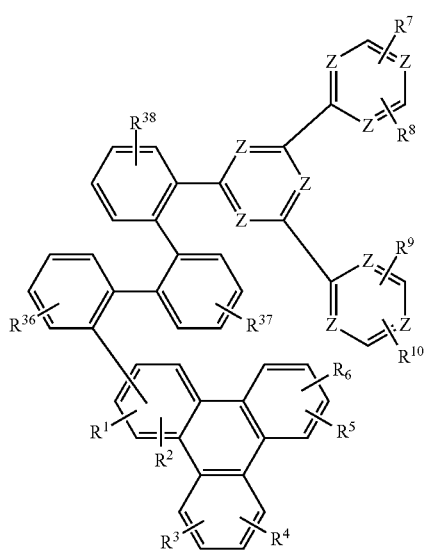
In the Chemical Formulae 1 d to 1 t, Z, $R^1$ to $R^{14}$, $R^{17}$ to $R^{20}$, $R^{23}$ to $R^{26}$ and $R^{36}$ to $R^{38}$ are the same as described above.
The luminescent material may be, for example compounds listed by the Group 2, but are not limited thereto.
[Group 2]
1
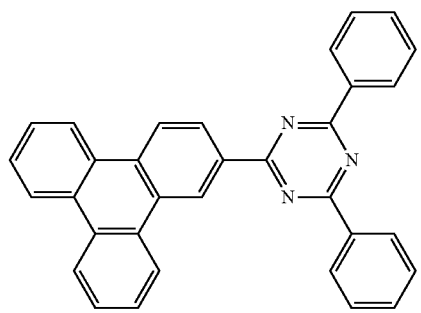
2
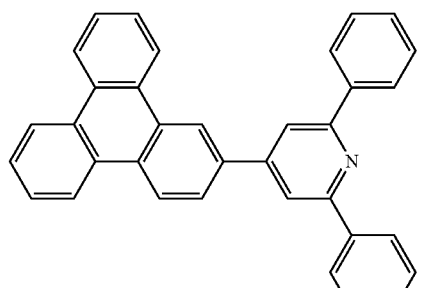
3
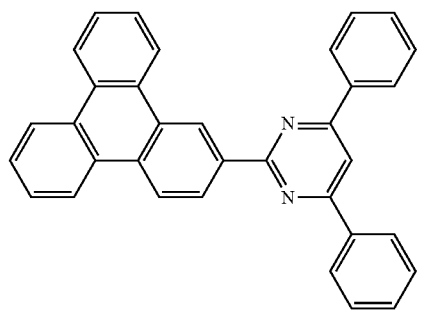

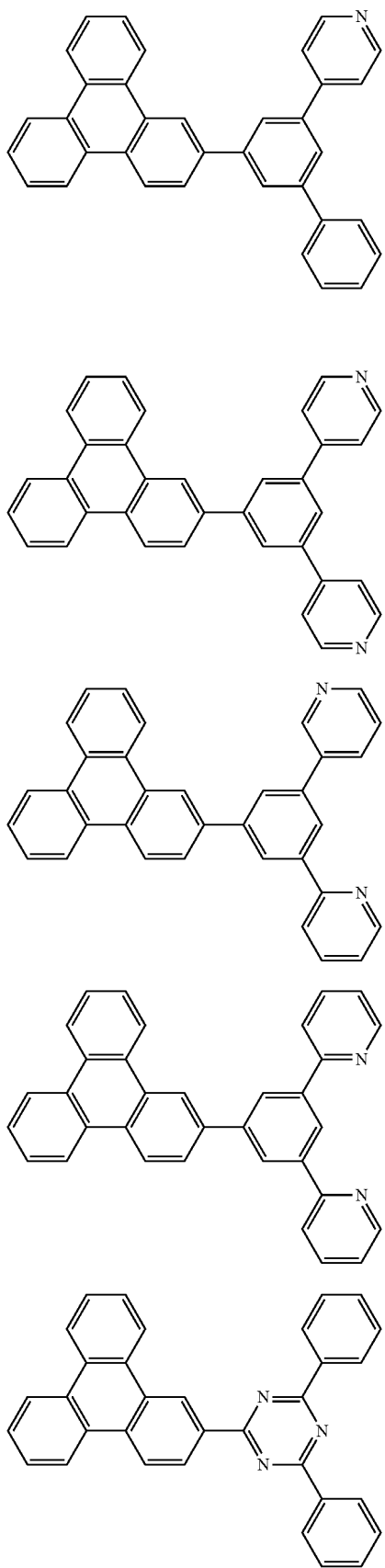
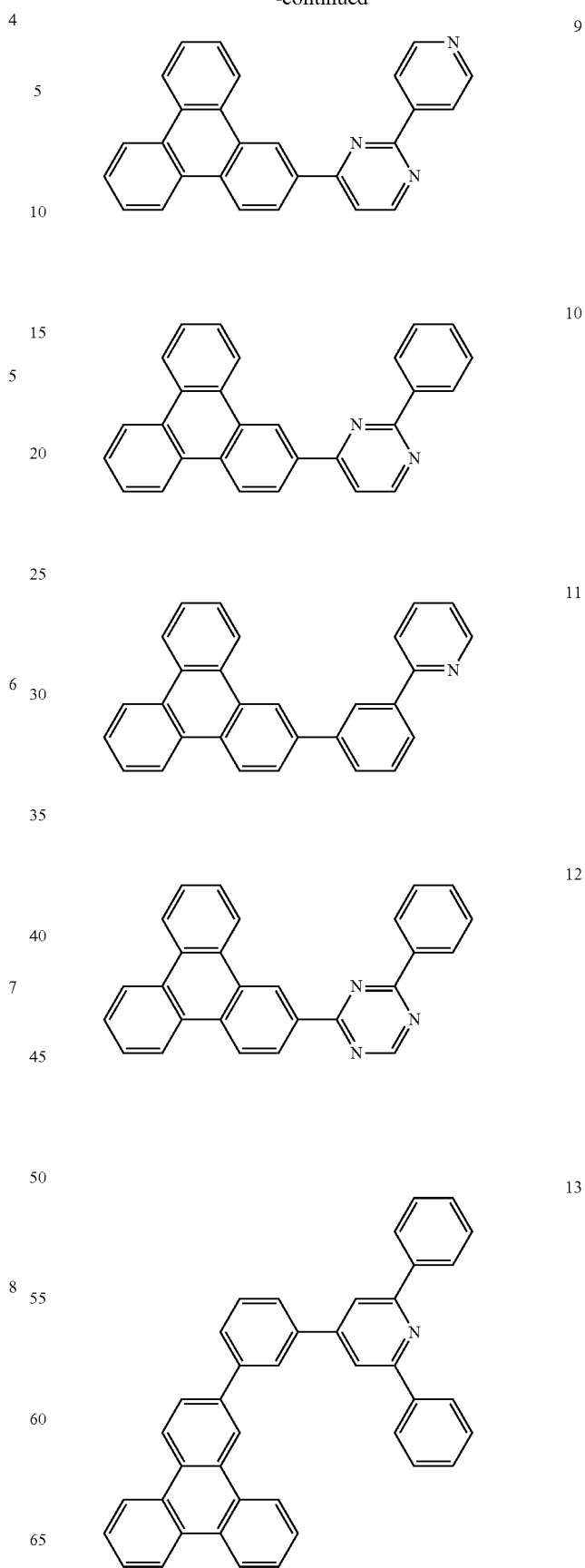

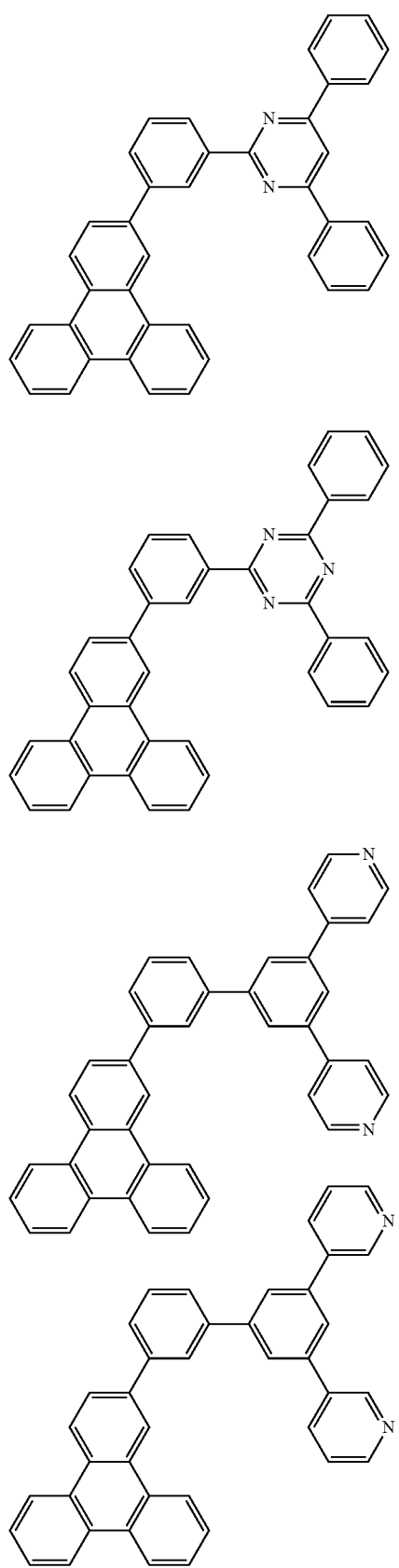
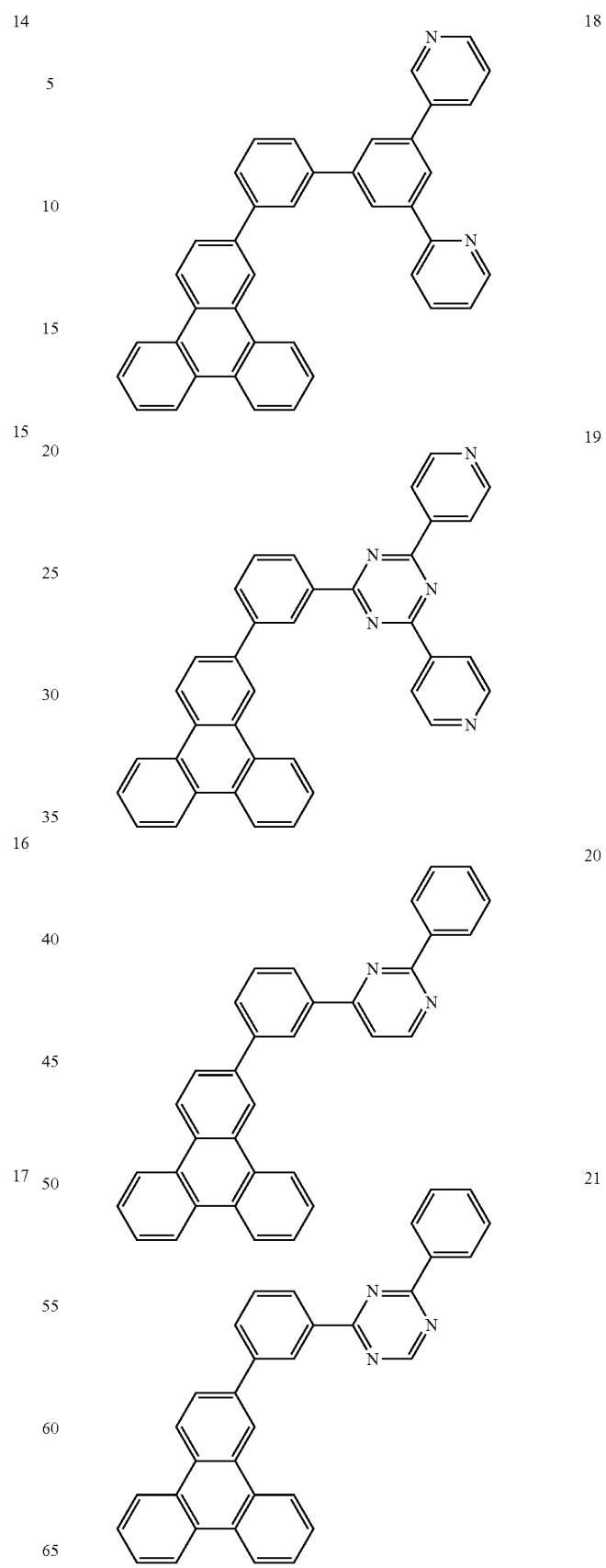

22
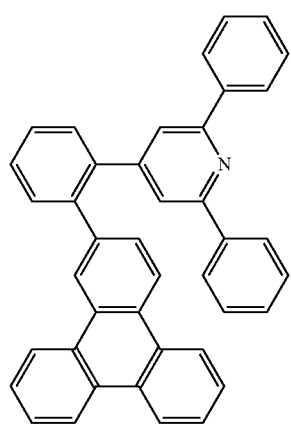
23
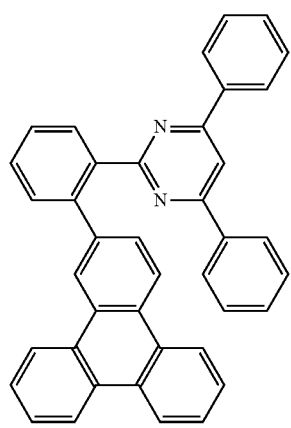
24
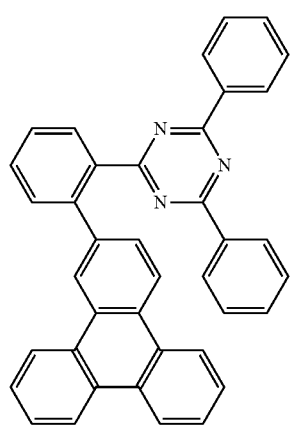
25
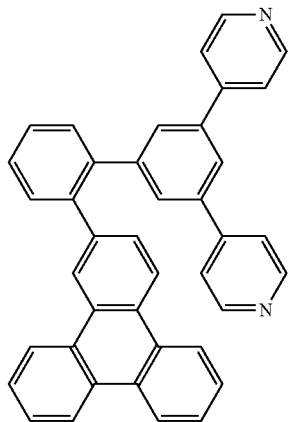
26
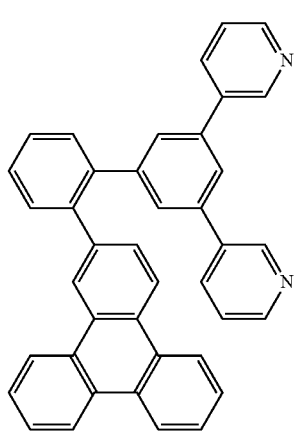
27
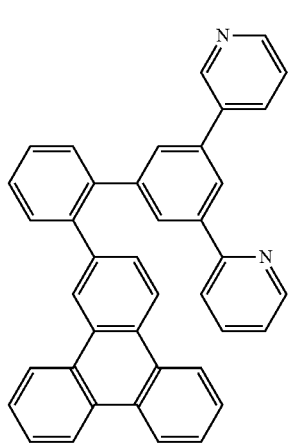

28
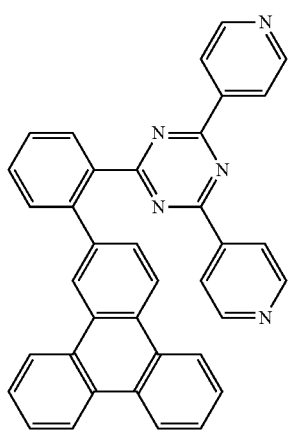
29
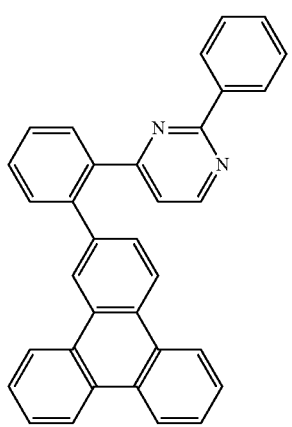
30
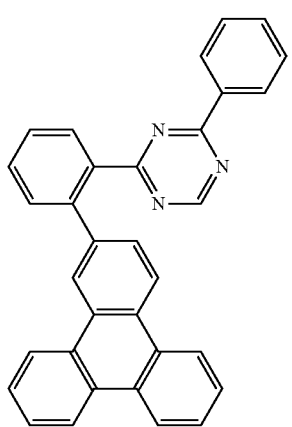
31
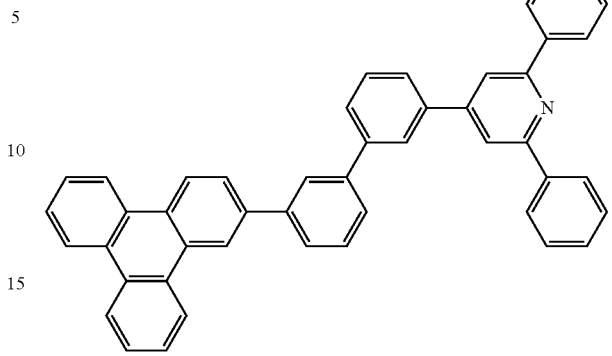
32
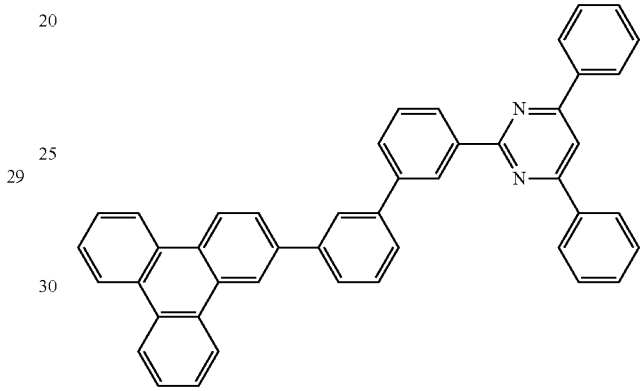
33
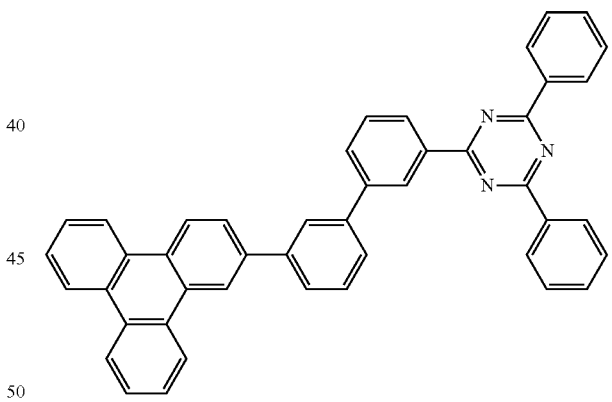
34
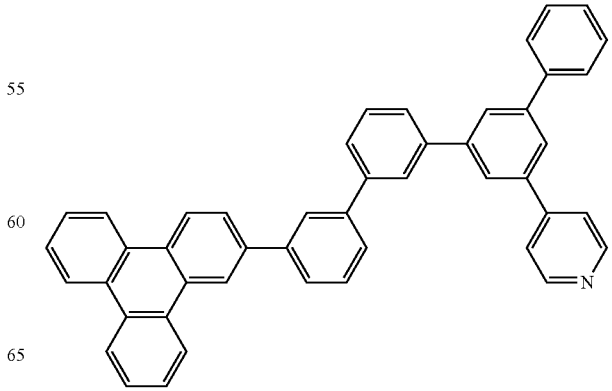

35
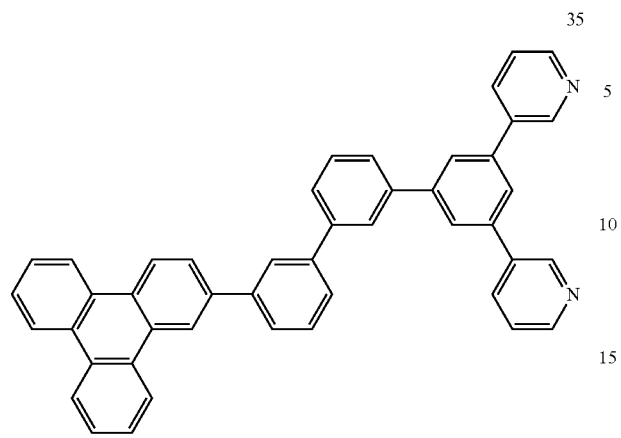
36
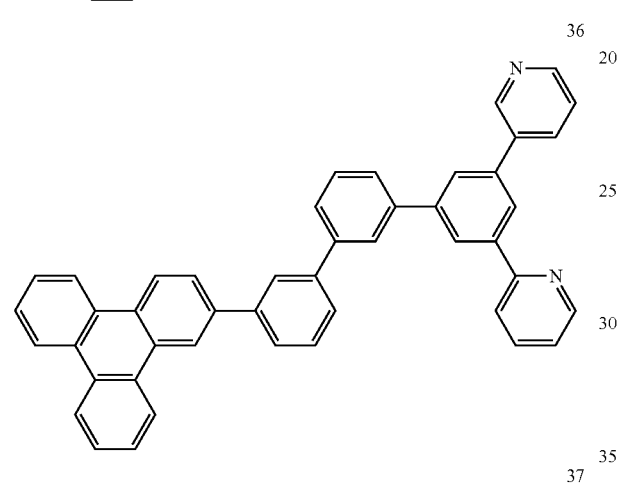
37
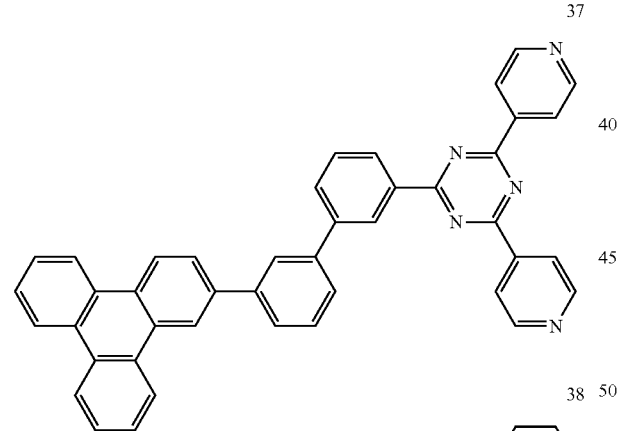
38
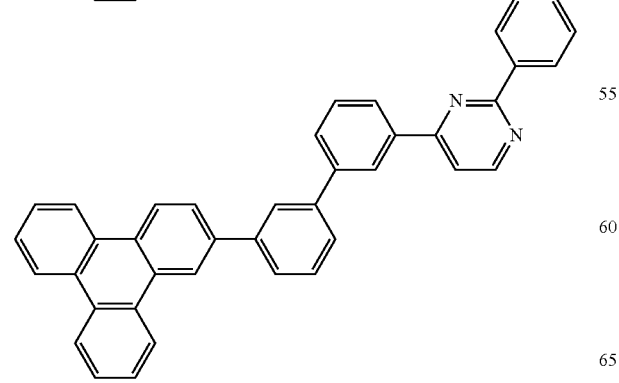
39
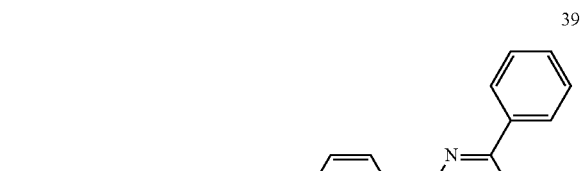
40
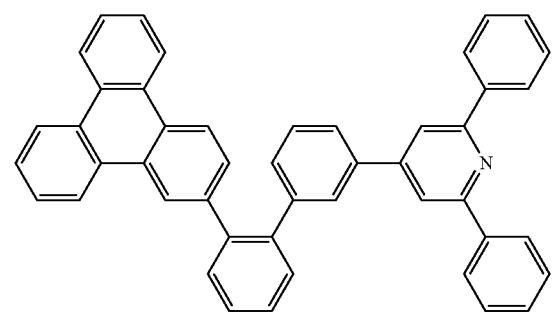
41
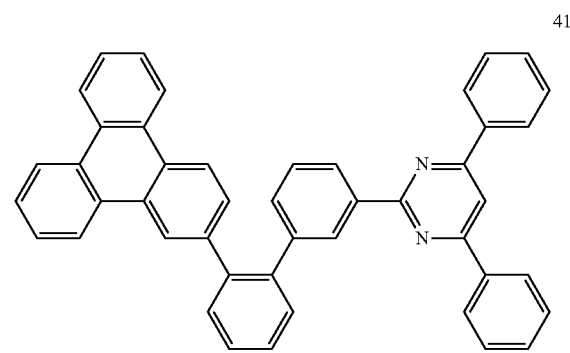
42
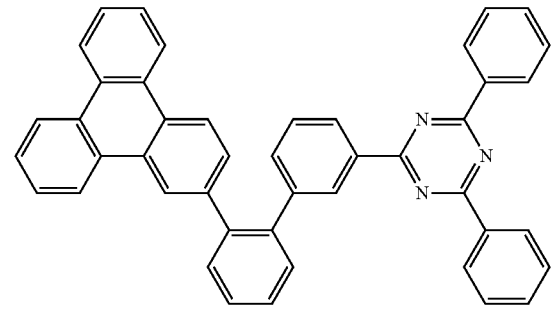

43
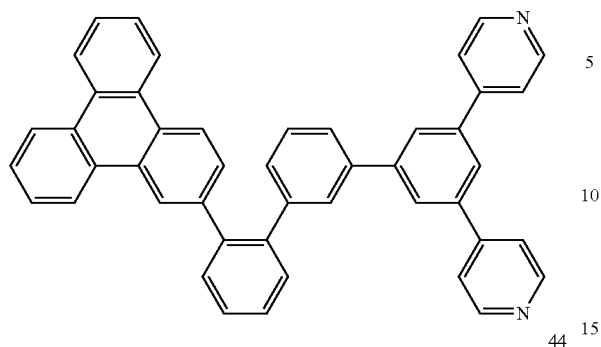
44
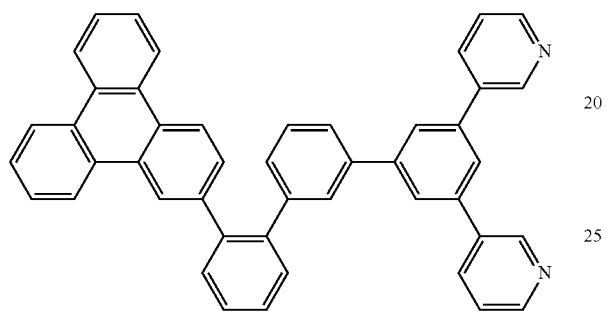
45
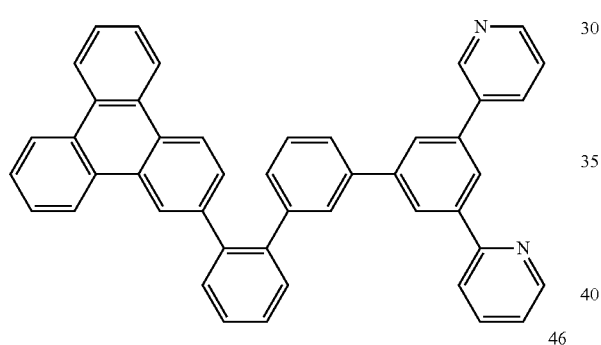
46
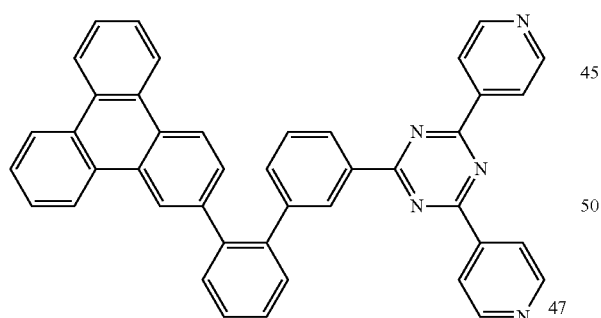
47
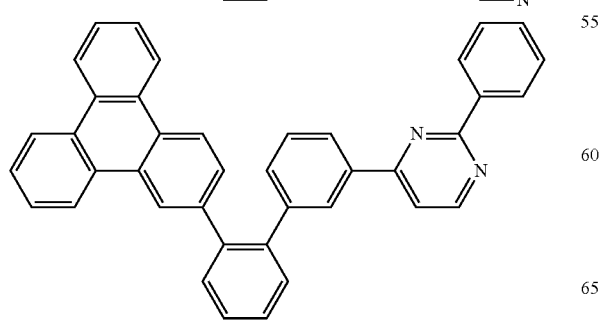
48
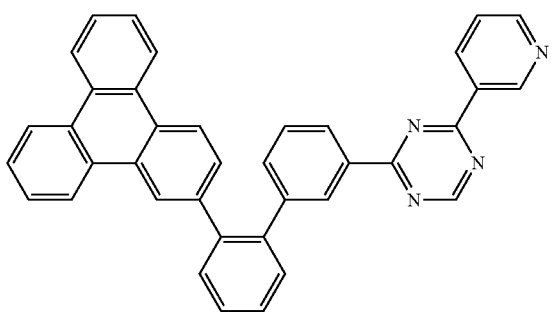
49
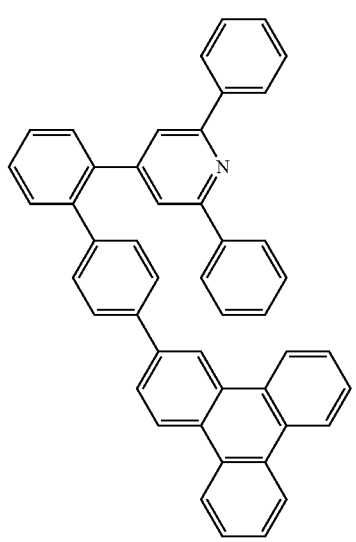
50
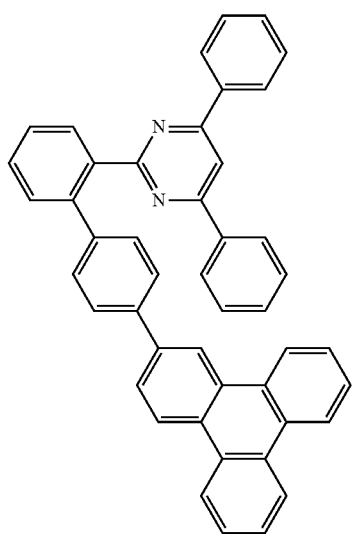

-continued
51
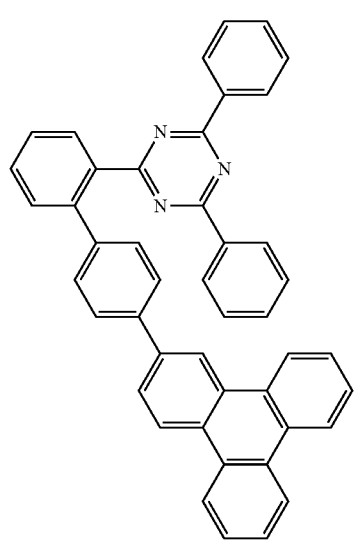
52
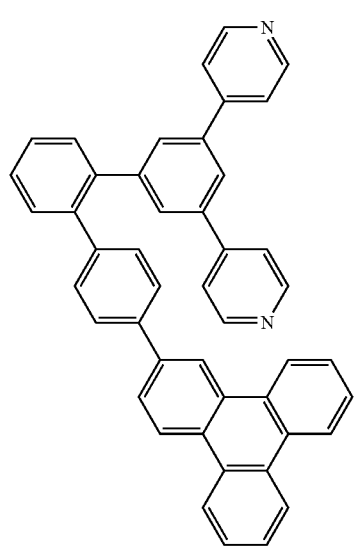
53
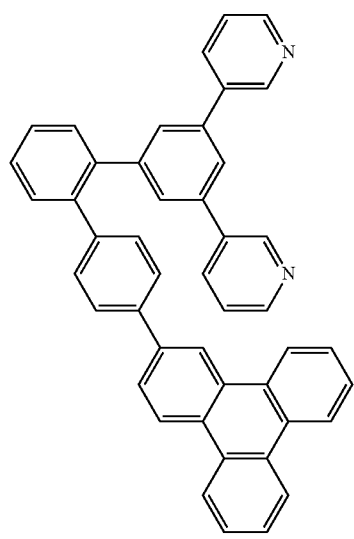
-continued
54
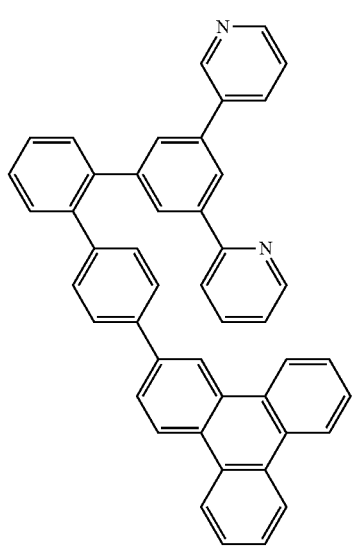
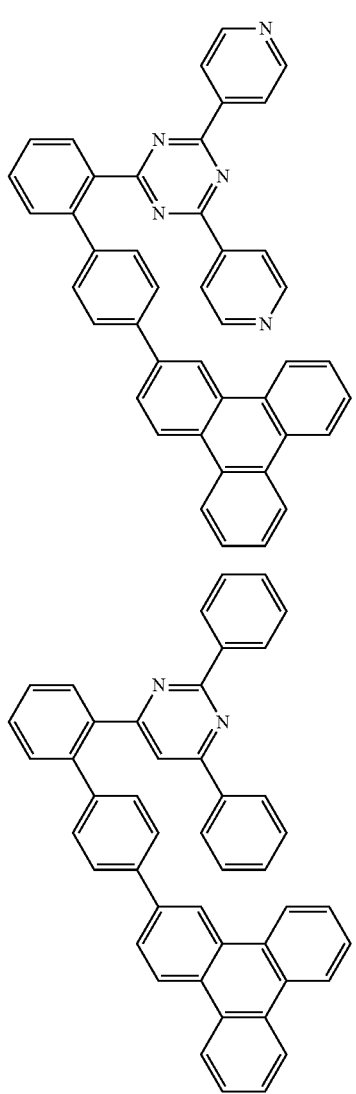

-continued
57
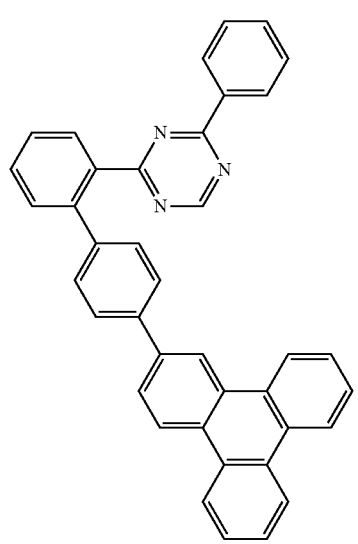
58
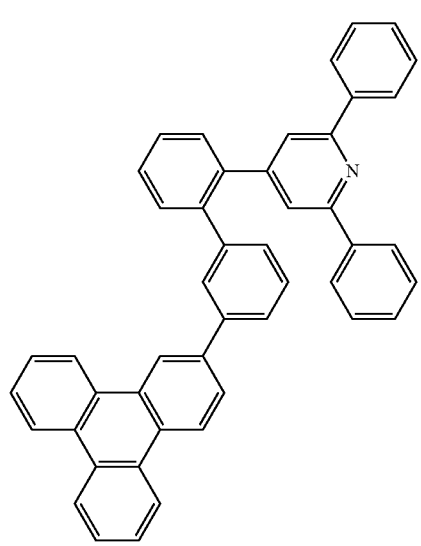
59
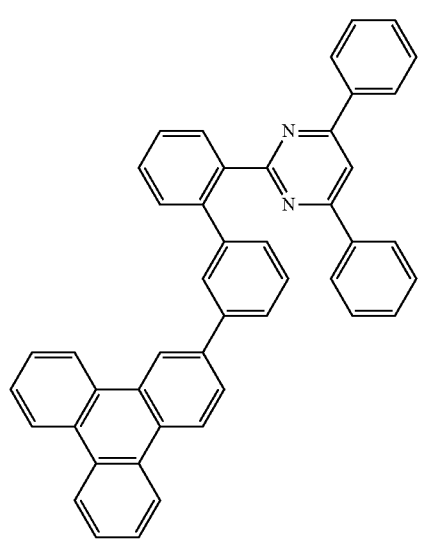
-continued
60
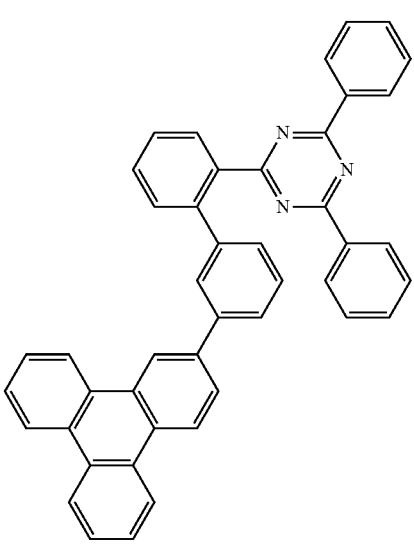
61
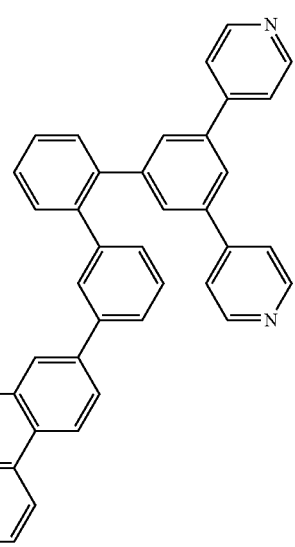
62
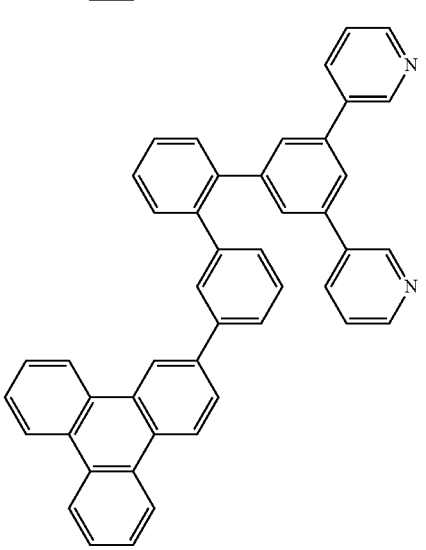

-continued
63
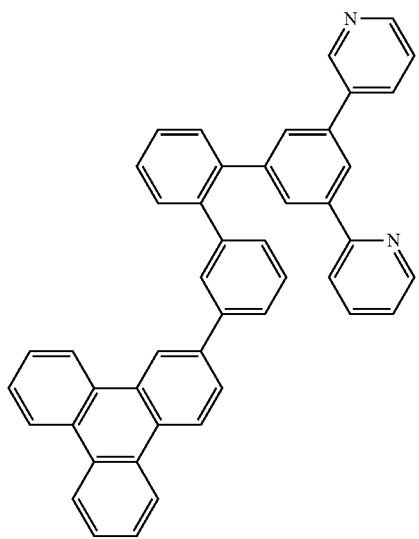
64
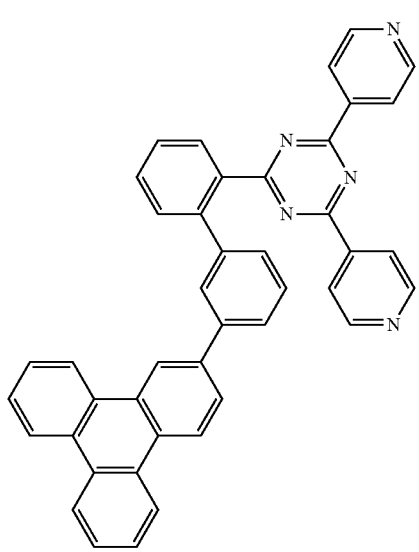
65
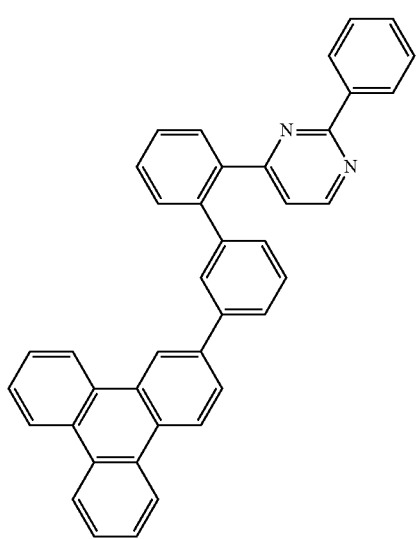
-continued
66
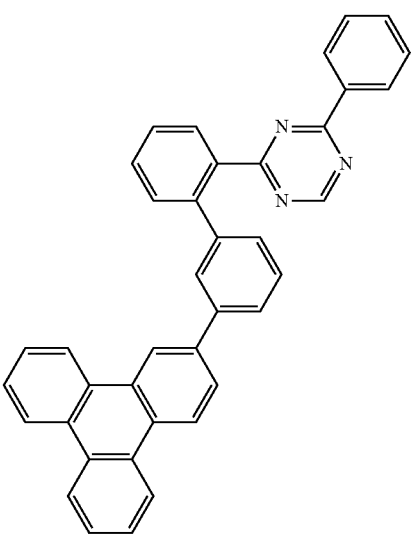
67
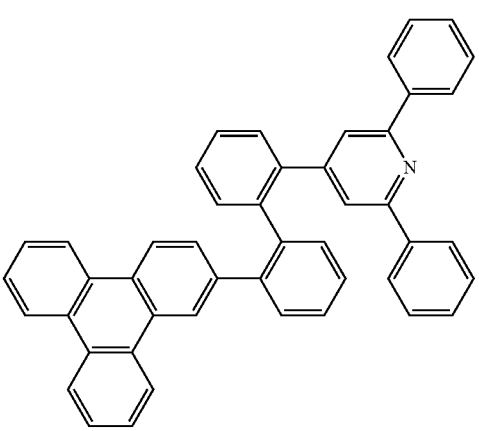
68
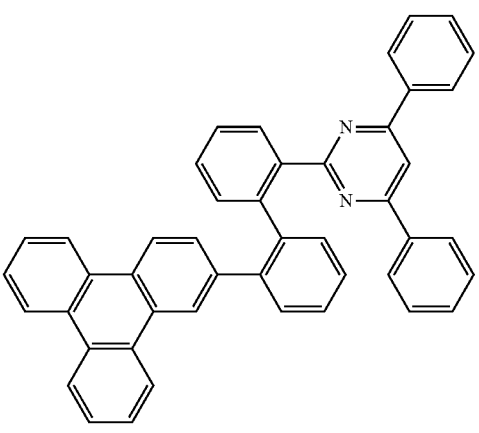

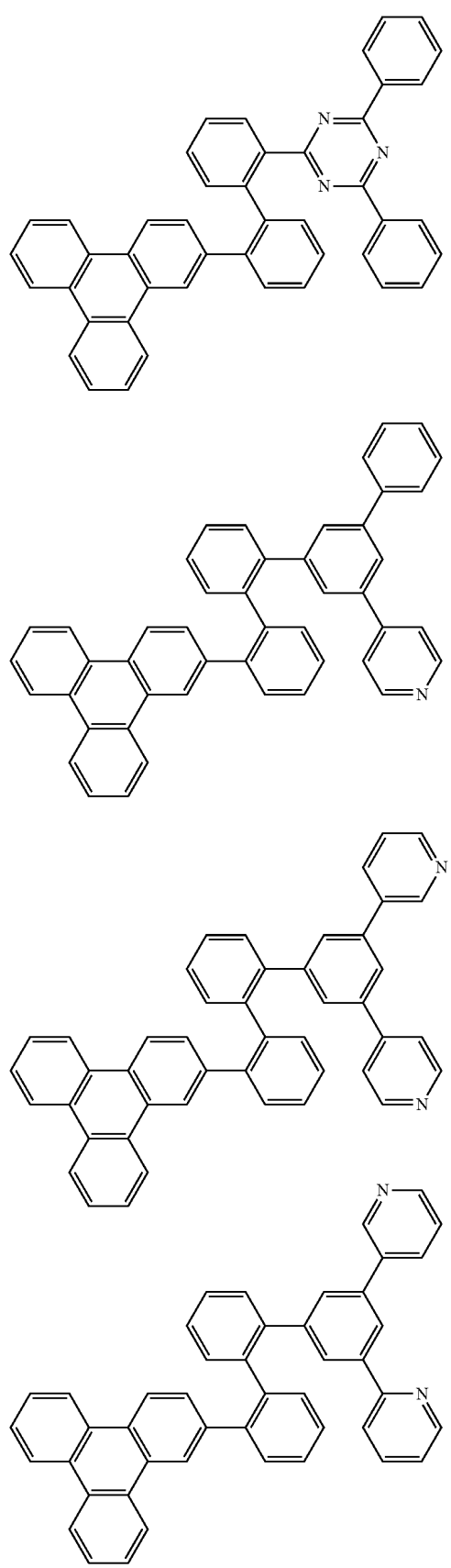
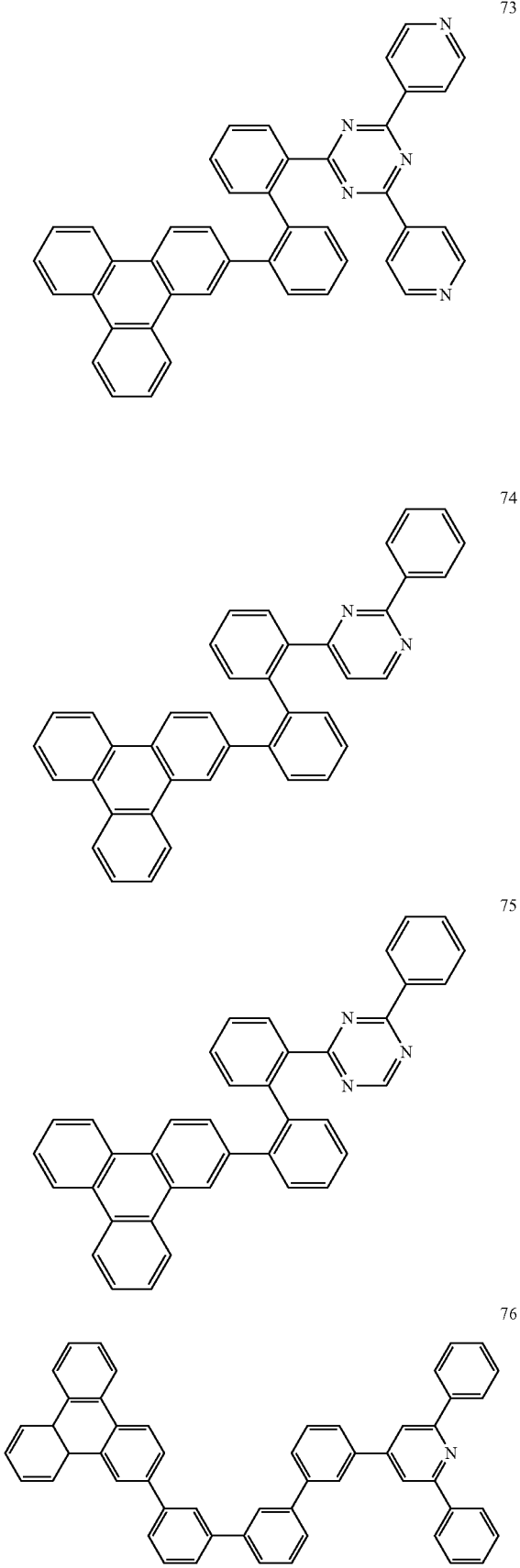

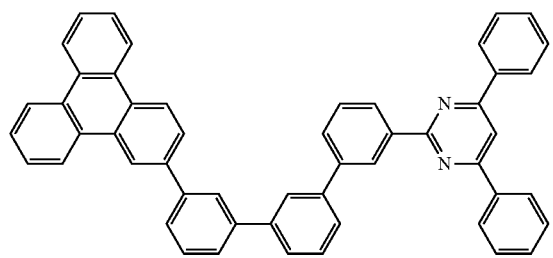
77
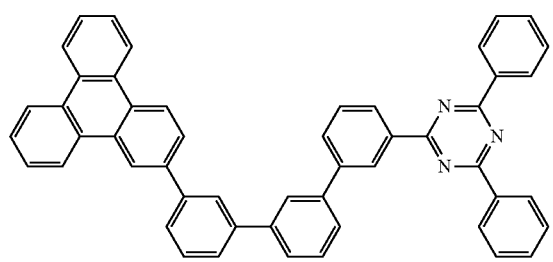
78
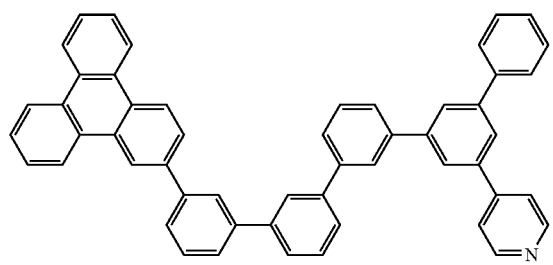
79
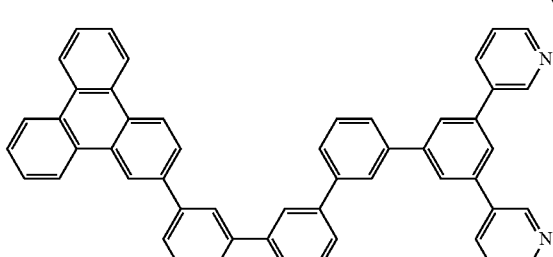
80
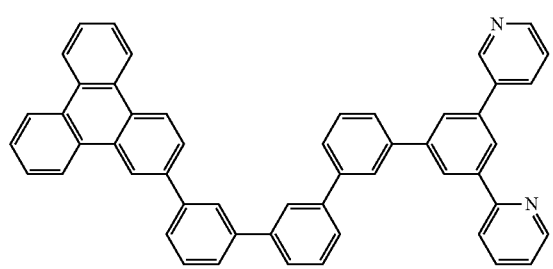
81
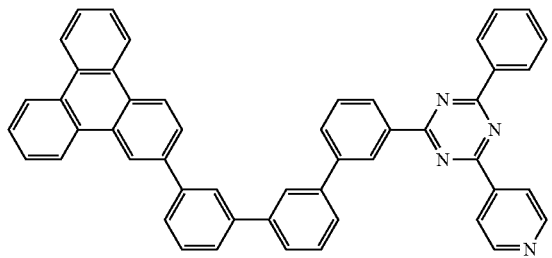
82
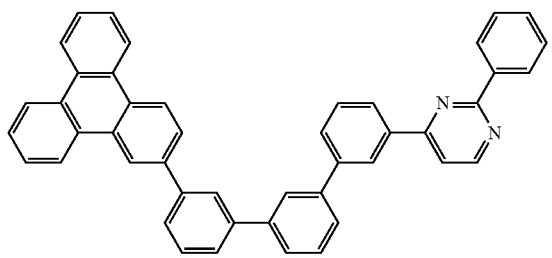
83
83
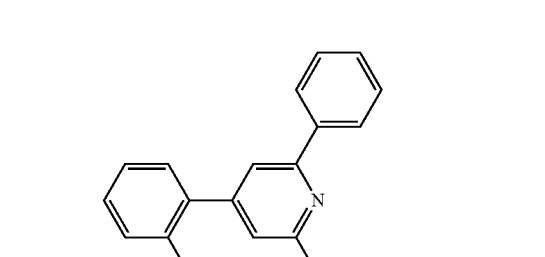
84
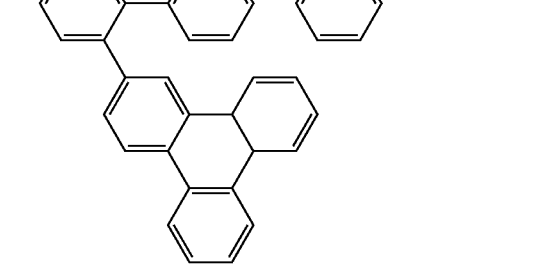
85

86
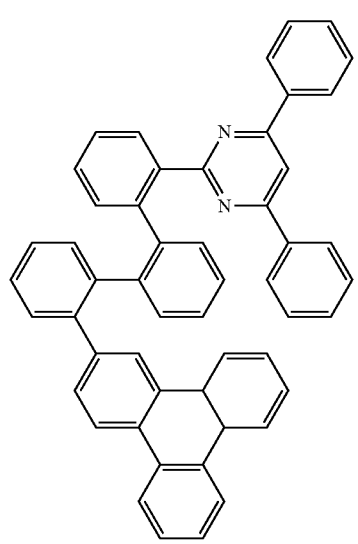
87
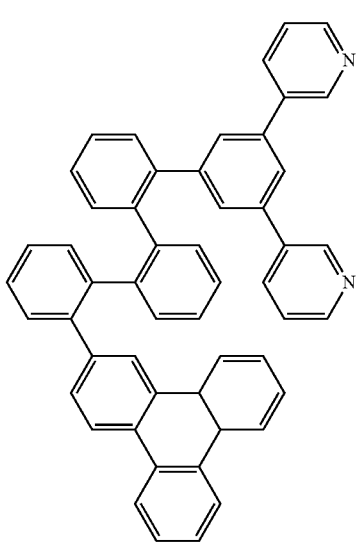
88
89
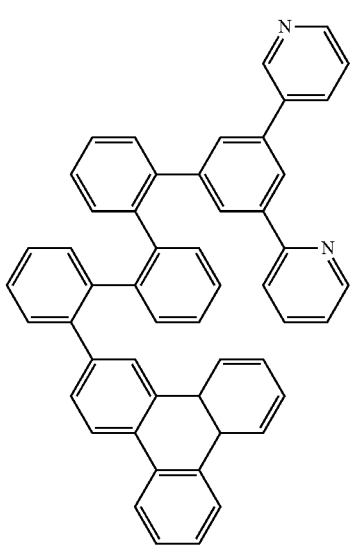
90
91
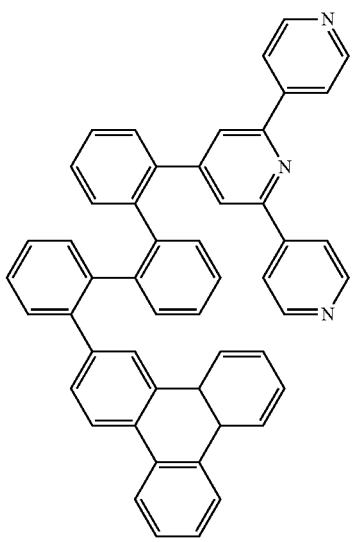

92
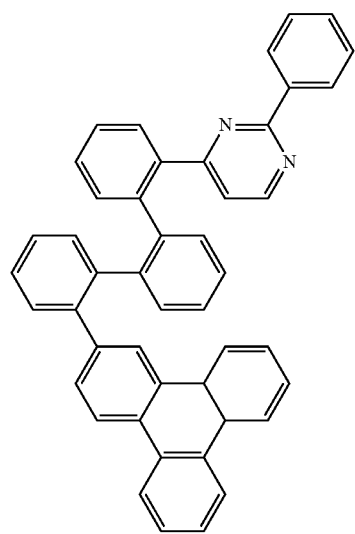
93
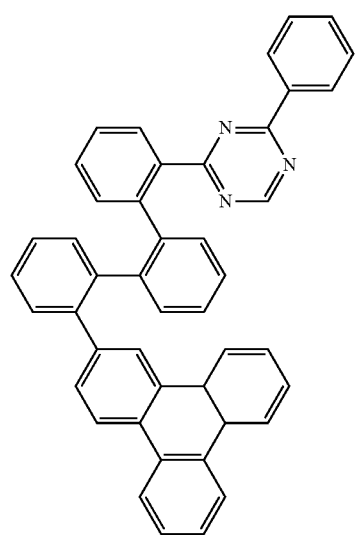
94
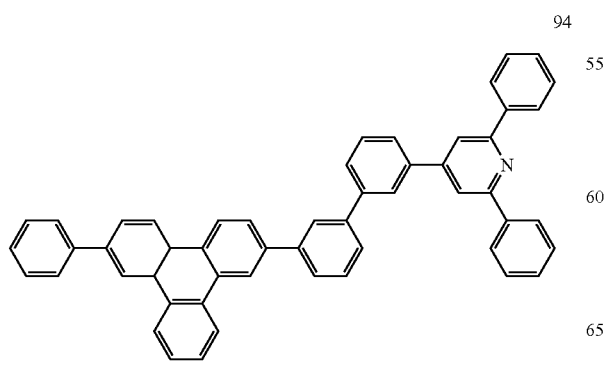
95
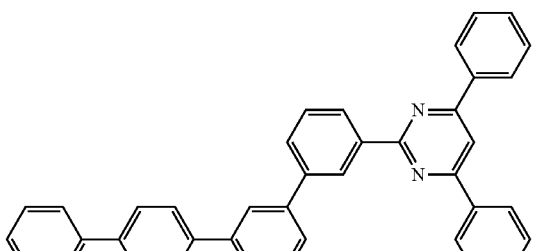
96
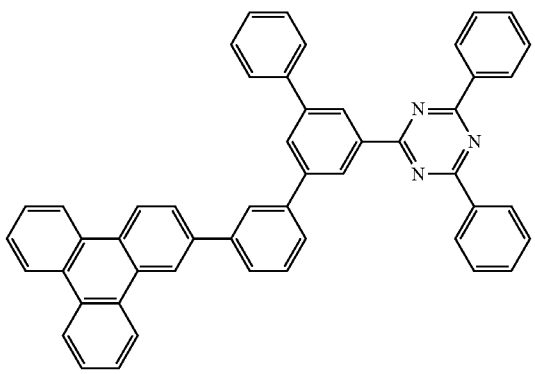
97
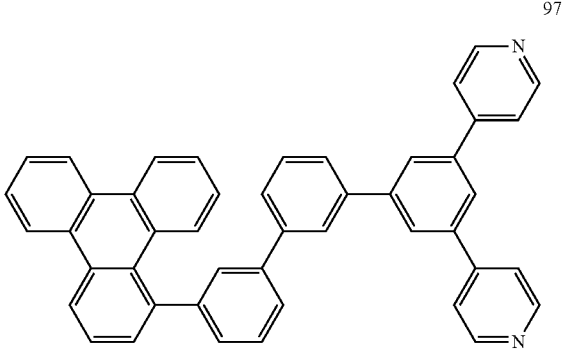
98
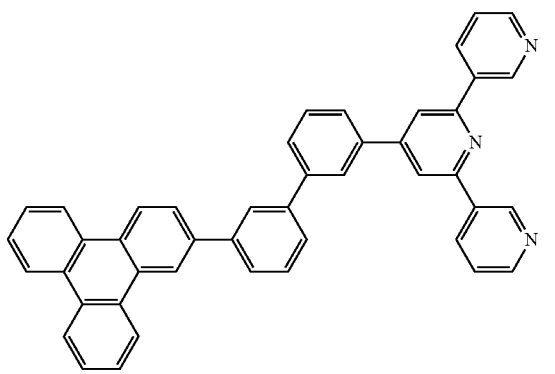

-continued

99

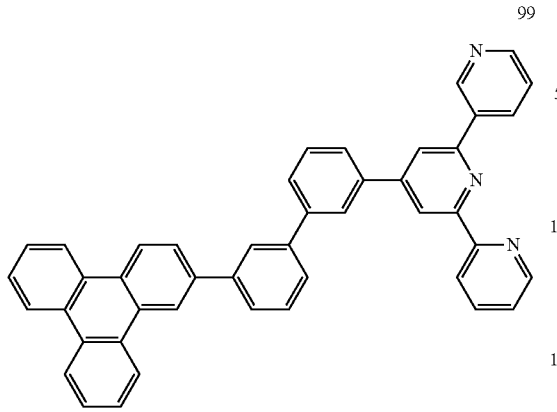

Hereinafter, an organic optoelectric device to which the luminescent material is applied is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

Herein, an organic light emitting diode as one example of an organic optoelectric device is described referring to drawings.

Figure 2:
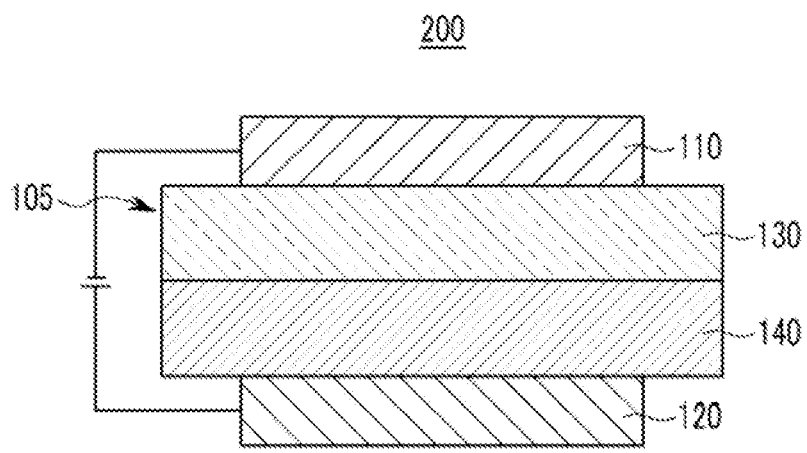

FIGS. 1 and 2 are cross-sectional views of each organic light emitting diode according to one embodiment.

Referring to FIG. 1, an organic light emitting diode 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure such as LiF/Al, LiO2/Al, LiF/Ca, LiF/Al and BaF2/Ca, but is not limited thereto.

The organic layer 105 may include an emission layer 130 including the luminescent material.

The emission layer 130 may include for example the luminescent material at alone, a mixture of at least two kinds of the luminescent material, or a mixture of the luminescent material and other compounds. When the luminescent material is mixed with other compounds, for example they may be mixed as a host and a dopant, and the luminescent material may be for example a host. The host may be, for example a phosphorescent host or fluorescent host, and may be, for example a phosphorescent host.

When the luminescent material is included as a host, a dopant may be an inorganic, organic, or organic/inorganic compound, and may be selected from well-known dopants.

Referring to FIG. 2, an organic light emitting diode 200 further includes a hole auxiliary layer 140 as well as an emission layer 130. The hole auxiliary layer 140 may further increase hole injection and/or hole mobility between the anode 120 and emission layer 130 and block electrons. The hole auxiliary layer 140 may be, for example a hole transport layer (HTL), a hole injection layer (HIL), and/or an electron blocking layer, and may include at least one layer. The hole auxiliary layer 140 may include a well-known material having hole transport capability.

In one embodiment, an organic light emitting diode may further include an electron transport layer (ETL), an electron injection layer (EIL), a hole injection layer (HIL), and the like, as an organic layer 105 in FIG. 1 or FIG. 2. The electron transport layer (ETL) and the electron injection layer (EIL) may include a well-known material having electron transport capability, and the hole injection layer (HIL) may include a well-known material having hole injection characteristics.

The organic light emitting diodes 100 and 200 may be manufactured by forming an anode or a cathode on a substrate, forming an organic layer in accordance with a dry coating method such as evaporation, sputtering, plasma plating, and ion plating or a wet coating method such as spin coating, slit coating, dipping, flow coating, and inkjet printing; and forming a cathode or an anode thereon.

The organic light emitting diode may be applied to an organic light emitting diode (OLED) display.

MODE FOR INVENTION

Hereinafter, the embodiments are illustrated in more detail with reference to examples. These examples, however, are not in any sense to be interpreted as limiting the scope of the invention.

Synthesis of Luminescent Material

Representative Synthesis Method

A representative synthesis method is shown in the representative reaction scheme.

[Representative Reaction Scheme]

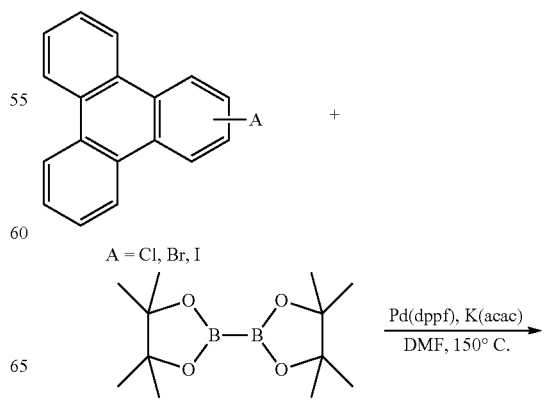

-continued

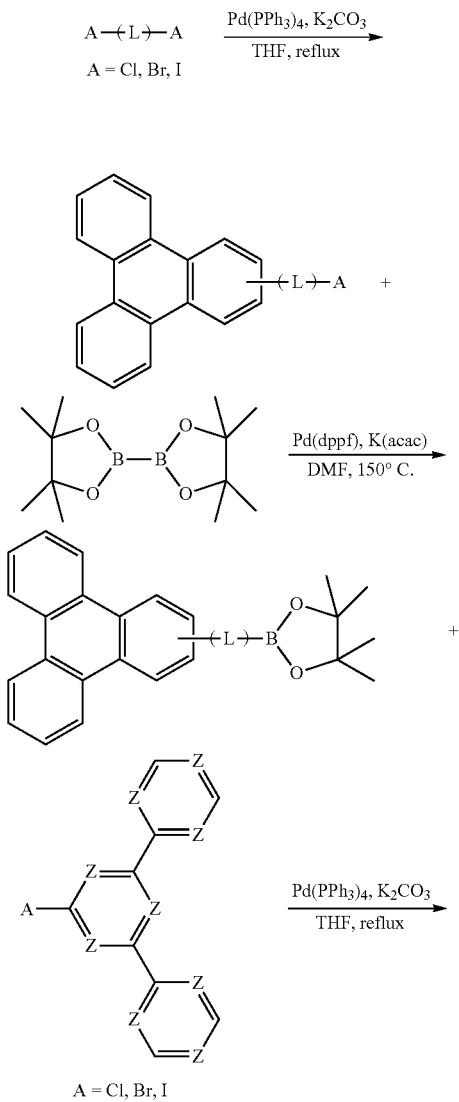
A = Cl, Br, I

Synthesis of Intermediate

Synthesis Example 1

Synthesis of Intermediate I-1

[Reaction Scheme 1]

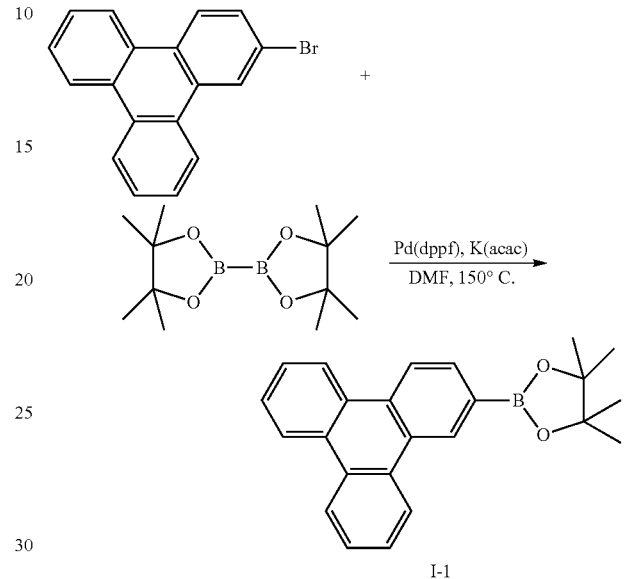

2-bromotriphenylene (100 g, 326 mmol) was dissolved in 1 L of dimethylforamide (DMF) in a nitrogen environment, bis(pinacolato)diboron (99.2 g, 391 mmol), (1,1'-bis(diphenylphosphine)ferrocene)dichloropalladium (II) (2.66 g, 3.26 mmol), and potassium acetate (80 g, 815 mmol) were added thereto, and the mixture was heated and refluxed at 150° C. for 5 hours. When the reaction was complete, water was added to the reaction solution, and the mixture was filtered and dried in a vacuum oven. This obtained residue was separated and purified through flash column chromatography, obtaining the compound I-1 (113 g, 98%).

HRMS (70 eV, EI+): m/z calcd for C24H23BO2: 354.1791. found: 354.

Elemental Analysis: C, 81%; H, 7%

Synthesis Example 2

Synthesis of Intermediate I-2

[Reaction Scheme 2]

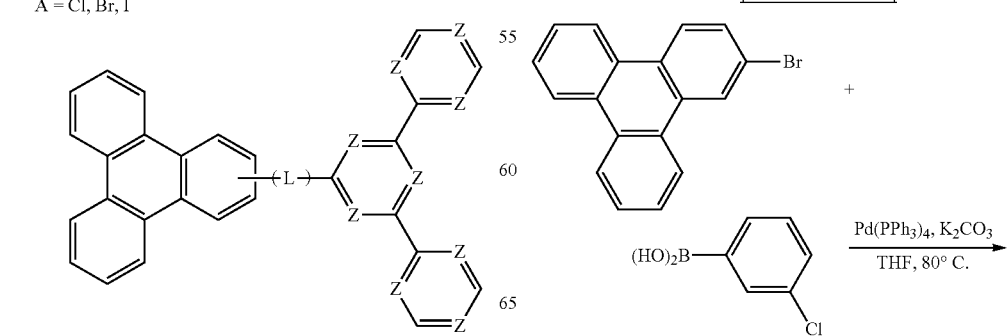

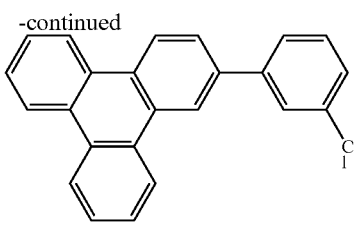

I-2

2-bromotriphenylene (32.7 g, 107 mmol) was dissolved in 0.3 L of tetrahydrofuran (THF) in a nitrogen environment, 3-chlorophenylboronic acid (20 g, 128 mmol) and tetrakis (triphenylphosphine)palladium (1.23 g, 1.07 mmol) were added thereto, and the mixture was agitated. Potassium carbonate (36.8 g, 267 mmol) saturated in water was added to the agitated resultant, and the resulting mixture was heated and refluxed at 80° C. for 24 hours. When the reaction was complete, water was added to the reaction solution, the mixture was extracted with dichloromethane (DCM), anhydrous MgSO4 was used to remove moisture therefrom, and the obtained product was filtered and concentrated under a reduced pressure. The obtained residue was separated and purified through flash column chromatography, obtaining the compound I-2 (22.6 g, 63%).

HRMS (70 eV, El+): m/z calcd for C24H15Cl: 338.0862. found: 338.

Elemental Analysis: C, 85%; H, 5%

Synthesis Example 3

Synthesis of Intermediate I-3

[Reaction Scheme 3]

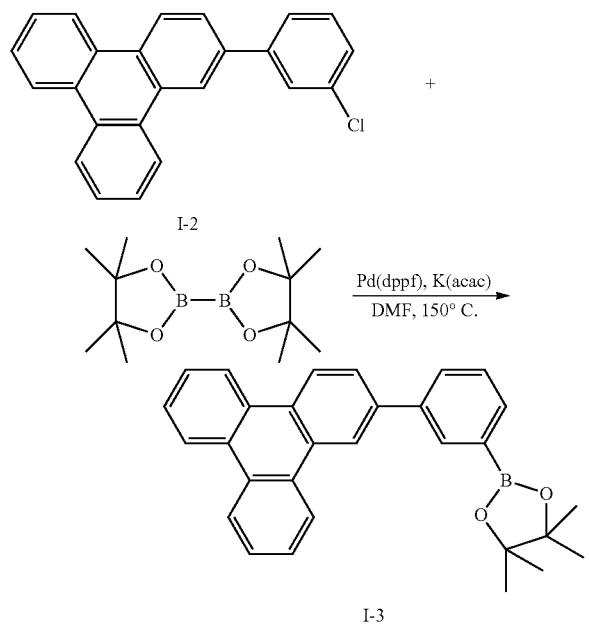

I-3

The compound I-2 (22.6 g, 66.7 mmol) was dissolved in 0.3 L of dimethylforamide (DMF) in a nitrogen environment, bis(pinacolato)diboron (25.4 g, 100 mmol), 1,1'-bis (diphenylphosphine)ferrocene)dichloropalladium (II) (0.54 g, 0.67 mmol), and potassium acetate (16.4 g, 167 mmol) were added thereto, and the mixture was heated and refluxed at 150° C. for 48 hours. When the reaction was complete, water was added to the reaction solution, and the mixture was filtered and dried in a vacuum oven. This obtained residue was separated and purified through flash column chromatography, obtaining a compound I-3 (18.6 g, 65%).

HRMS (70 eV, El+): m/z calcd for C30H27BO2: 430.2104. found: 430.

Elemental Analysis: C, 84%; H, 6%

Synthesis Example 4

Synthesis of Intermediate I-4

[Reaction Scheme 4]

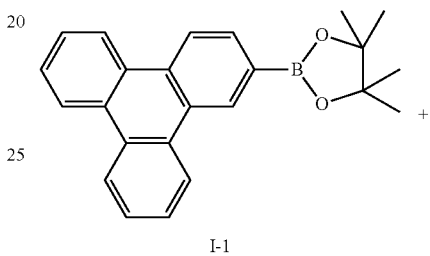

I-1

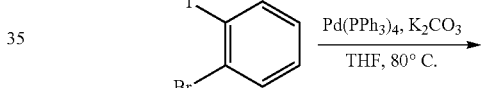

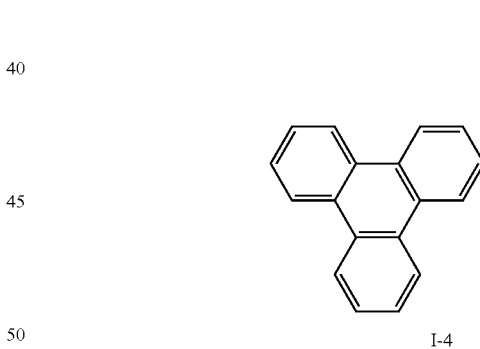

I-4

The compound I-1 (100 g, 282 mmol) was dissolved in 1 L of tetrahydrofuran (THF) in nitrogen environment, 1-bromo-2-iodobenzene (95.9 g, 339 mmol) and tetrakis (triphenylphosphine)palladium (3.26 g, 2.82 mmol) were added thereto, and the mixture was agitated. Potassium carbonate (97.4 g, 705 mmol) saturated in water was added thereto, and the mixture was heated and refluxed at 80° C. for 53 hours. When the reaction was complete, water was added to the reaction solution, the mixture was extracted with dichloromethane (DCM) and then, treated with anhydrous MgSO4 to remove moisture therefrom, and the obtained product was filtered and concentrated under a reduced pressure. The obtained residue was separated and purified through flash column chromatography, obtaining the compound I-4 (95.1 g, 88%).

HRMS (70 eV, El+): m/z calcd for $C_{24}H_{15}Br$: 382.0357. found: 382.

Elemental Analysis: C, 75%; H, 4%

Synthesis Example 5

Synthesis of Intermediate I-5

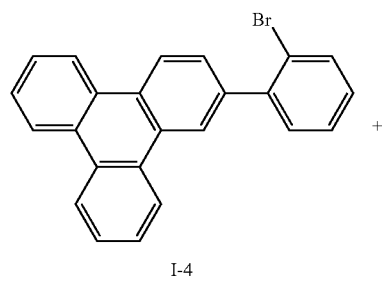

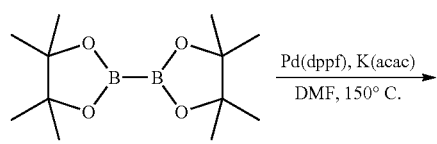

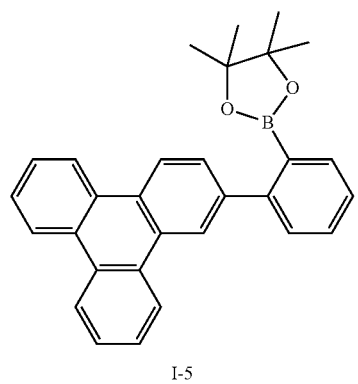

The compound I-4 (90 g, 235 mmol) was dissolved in 0.8 L of dimethylforamide (DMF) in a nitrogen environment, bis(pinacolato)diboron (71.6 g, 282 mmol), (1,1'-bis(diphenylphosphine)ferrocene)dichloropalladium (II) (1.92 g, 2.35 mmol), and potassium acetate (57.7 g, 588 mmol) were added thereto, and the mixture was heated and refluxed at 150° C. for 35 hours. When the reaction was complete, water was added to the reaction solution, and the mixture was filtered and dried in a vacuum oven. This obtained residue was separated and purified through flash column chromatography, obtaining the compound I-5 (74.8 g, 74%).

HRMS (70 eV, El+): m/z calcd for $C_{30}H_{27}BO_2$: 430.2104. found: 430.

Elemental Analysis: C, 84%; H, 6%

Synthesis Example 6

Synthesis of Intermediate I-6

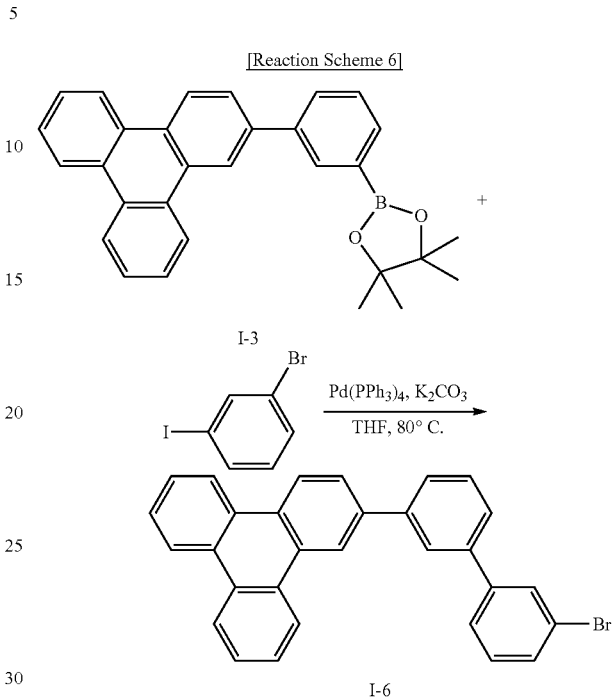

The compound I-3 (50 g, 116 mmol) was dissolved in 0.5 L of tetrahydrofuran (THF) in a nitrogen environment, 1-bromo-3-iodobenzene (39.4 g, 139 mmol) and tetrakis(triphenylphosphine)palladium (1.34 g, 1.16 mmol) were added thereto, and the mixture was agitated. Potassium carbonate (40.1 g, 290 mmol) saturated in water was added thereto, and the resulting mixture was heated and refluxed at 80° C. for 12 hours. When the reaction was complete, water was added to the reaction solution, and the mixture was extracted with dichloromethane (DCM) and then, treated with anhydrous $MgSO_4$ to remove moisture therefrom, and the remaining product was filtered and concentrated under a reduced pressure. The obtained residue was separated and purified through flash column chromatography, obtaining the compound I-6 (42.6 g, 80%).

HRMS (70 eV, El+): m/z calcd for C30H19Br: 458.0670. found: 458.

Elemental Analysis: C, 78%; H, 4%

Synthesis Example 7

Synthesis of Intermediate I-7

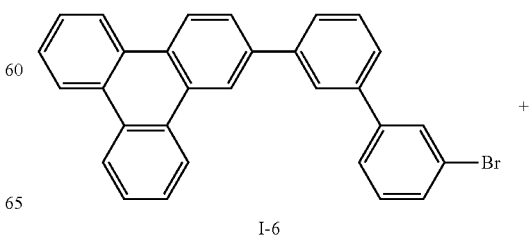

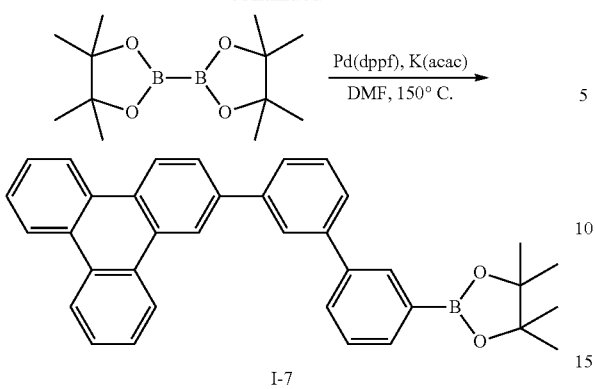
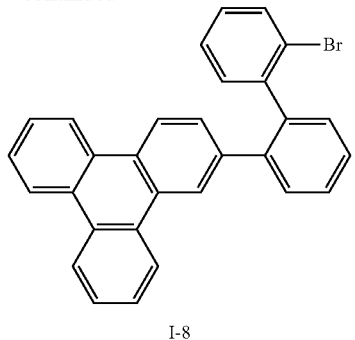

The compound I-6 (40 g, 87.1 mmol) was dissolved in 0.3 L of dimethylforamide (DMF) in a nitrogen environment, bis(pinacolato)diboron (26.5 g, 104 mmol), (1,1'-bis(diphenylphosphine)ferrocene)dichloropalladium (II) (0.71 g, 0.87 mmol), and potassium acetate (21.4 g, 218 mmol) were added thereto, and the mixture was heated and refluxed at 150° C. for 26 hours. When the reaction was complete, water was added to the reaction solution, and the mixture was filtered and dried in a vacuum oven. The obtained residue was separated and purified through flash column chromatography, obtaining the compound I-7 (34 g and 77%).

HRMS (70 eV, El+): m/z calcd for C36H31 BO2: 506.2417. found: 506.

Elemental Analysis: C, 85%; H, 6%

Synthesis Example 8

Synthesis of Intermediate I-8

[Reaction Scheme 8]

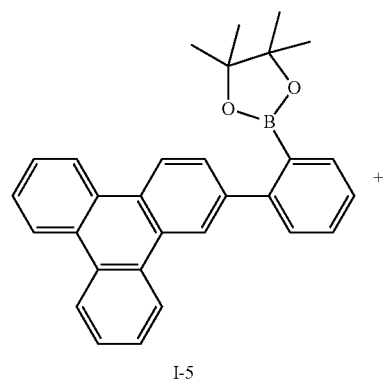

The compound I-5 (70 g, 163 mmol) was dissolved in 0.6 L of tetrahydrofuran (THF) in a nitrogen environment, 1-bromo-2-iodobenzene (55.2 g, 195 mmol) and tetrakis(triphenylphosphine)palladium (1.88 g, 1.63 mmol) were added thereto, and the mixture was agitated. Potassium carbonate (56.3 g, 408 mmol) saturated in water was added thereto, and the mixture was heated and refluxed at 80° C. for 12 hours. When the reaction was complete, water was added to the reaction solution, the mixture was extracted with dichloromethane (DCM) and treated with anhydrous MgSO$_4$ to remove moisture therefrom, and the remaining product was filtered and concentrated under a reduced pressure. The obtained residue was separated and purified through flash column chromatography, obtaining the compound I-8 (68.1 g, 91%).

HRMS (70 eV, El+): m/z calcd for C30H19Br: 458.0670. found: 458.

Elemental Analysis: C, 78%; H, 4%

Synthesis Example 9

Synthesis of Intermediate I-9

[Reaction Scheme 9]

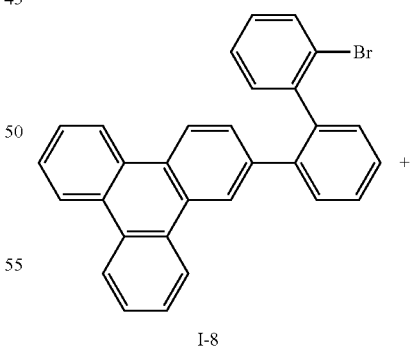

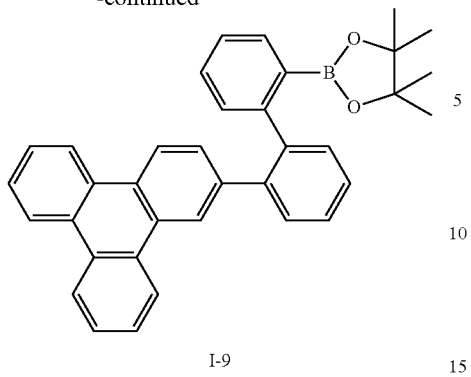

I-9

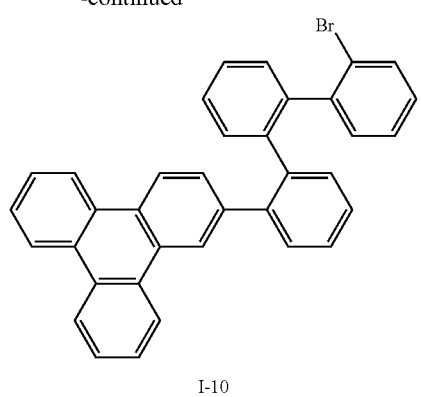

I-10

The compound I-8 (40 g, 87.1 mmol) was dissolved in 0.3 L of dimethylforamide (DMF) in a nitrogen environment, bis(pinacolato)diboron (26.5 g, 104 mmol), 1,1'-bis(diphenylphosphine)ferrocene)dichloropalladium (II) (0.71 g, 0.87 mmol), and potassium acetate (21.4 g, 218 mmol) were added thereto, and the mixture was heated and refluxed at 150° C. for 23 hours. When the reaction was complete, water was added to the reaction solution, and the mixture was filtered and dried in a vacuum oven. The obtained residue was separated and purified through flash column chromatography, obtaining the compound I-9 (30.4 g, 69%).

HRMS (70 eV, El+): m/z calcd for C36H31 BO2: 506.2417. found: 506.

Elemental Analysis: C, 85%; H, 6%

Synthesis Example 10

Synthesis of Intermediate I-10

[Reaction Scheme 10]

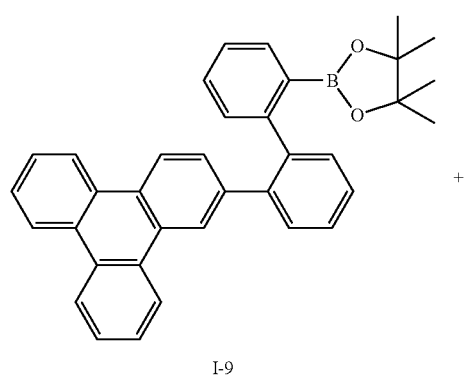

The compound I-9 (30 g, 59.2 mmol) was dissolved in 0.3 L of tetrahydrofuran (THF) in a nitrogen environment, 1-bromo-2-iodobenzene (20.1 g, 71.1 mmol) and tetrakis (triphenylphosphine)palladium (0.68 g, 0.59 mmol) were added thereto, and the mixture was agitated. Potassium carbonate (20.5 g, 148 mmol) saturated in water was added thereto, and the resulting mixture was heated and refluxed at 80° C. for 16 hours. When the reaction was complete, water was added to the reaction solution, and the mixture was extracted with dichloromethane (DCM) and then, treated with anhydrous MgSO4 to remove moisture therefrom, and the remaining product was filtered and concentrated under a reduced pressure. The obtained residue was separated and purified through flash column chromatography, obtaining the compound I-10 (32.4 g, 85%).

HRMS (70 eV, El+): m/z calcd for C36H23Br: 534.0983. found: 534.

Elemental Analysis: C, 81%; H, 4%

Synthesis Example 11

Synthesis of Intermediate I-11

[Reaction Scheme 11]

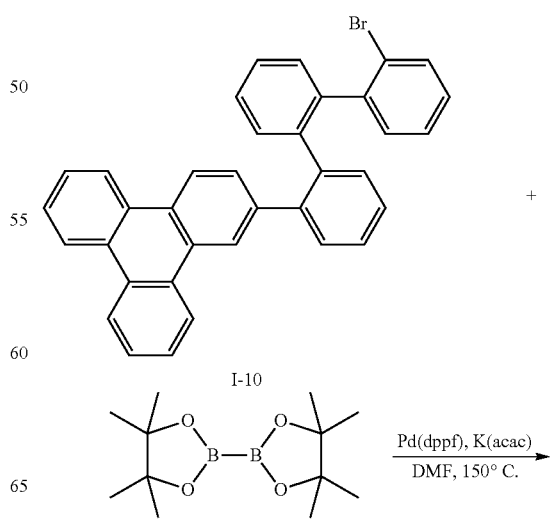

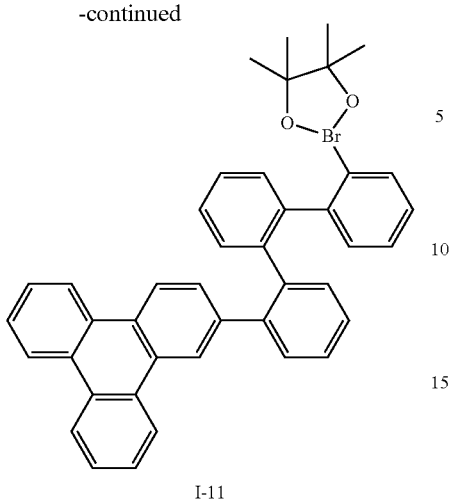

I-11

The compound I-10 (30 g, 56 mmol) was dissolved in 0.3 L of dimethylforamide (DMF) in a nitrogen environment, bis(pinacolato)diboron (17.1 g, 67.2 mmol), (1,1'-bis(diphenylphosphine)ferrocene)dichloropalladium (II) (0.46 g, 0.56 mmol), and potassium acetate (13.7 g, 140 mmol) were added thereto, and the mixture was heated and refluxed at 150° C. for 25 hours. When the reaction was complete, water was added to the reaction solution, and the mixture was filtered and dried in a vacuum oven. The obtained residue was separated and purified through flash column chromatography, obtaining the compound I-11 (22.8 g, 70%).

HRMS (70 eV, El+): m/z calcd for C42H35BO2: 582.2730. found: 582.

Elemental Analysis: C, 87%; H, 6%

Synthesis of Final Compound

Synthesis Example 12

Synthesis of Compound 1

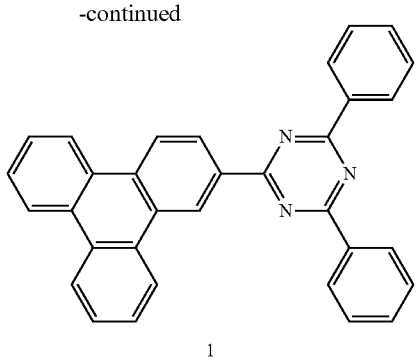

1

The compound 1-1 (20 g, 56.5 mmol) was dissolved in 0.2 L of tetrahydrofuran (THF) in a nitrogen environment, 2-chloro-4,6-diphenyl-1,3,5-triazine (15.1 g, 56.5 mmol) and tetrakis(triphenylphosphine)palladium (0.65 g, 0.57 mmol) were added thereto, and the mixture was agitated. Potassium carbonate (19.5 g, 141 mmol) saturated in water was added thereto, and the resulting mixture was heated and refluxed at 80° C. for 20 hours. When the reaction was complete, water was added to the reaction solution, the mixture was extracted with dichloromethane (DCM) and then, treated with anhydrous MgSO4 to remove moisture, and the obtained product was filtered and concentrated under a reduced pressure. This obtained residue was separated and purified through flash column chromatography, obtaining the compound 1 (22.1 g, 85%).

HRMS (70 eV, El+): m/z calcd for C33H21N3: 459.1735. found: 459.

Elemental Analysis: C, 86%; H, 5%

Synthesis Example 13

Synthesis of Compound 13

[Reaction Scheme 12]

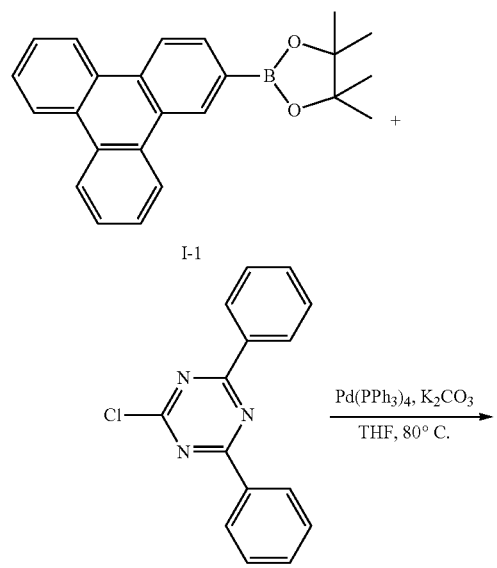

[Reaction Scheme 13]

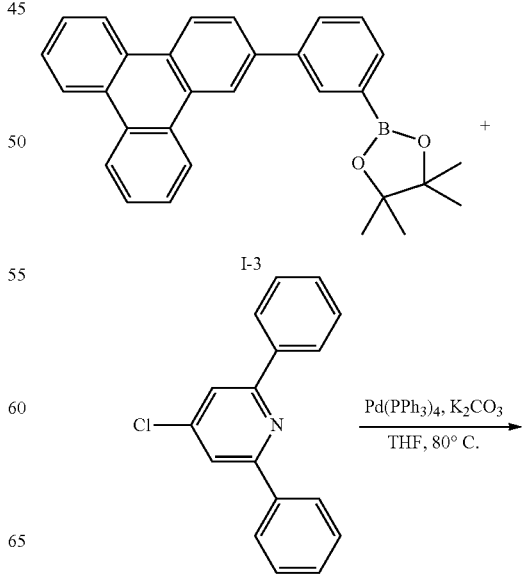

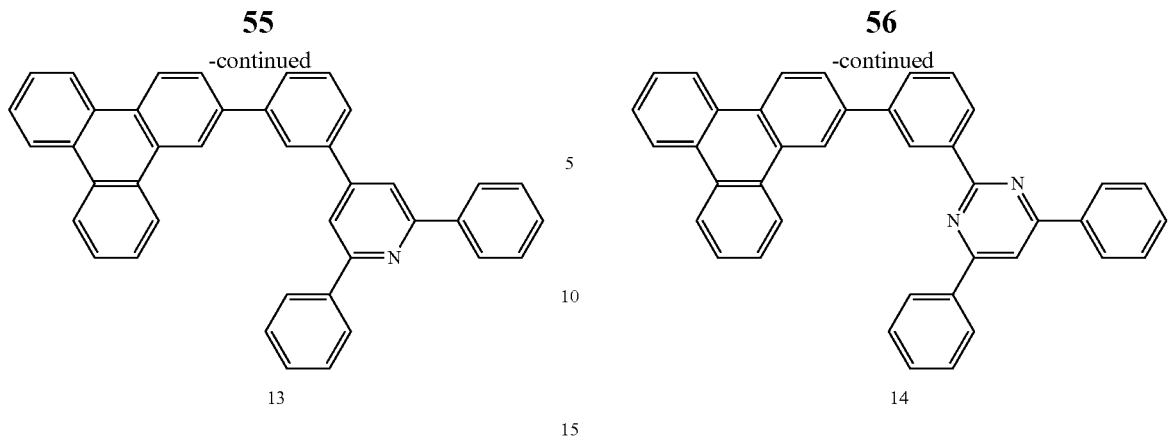

13  14

The compound 1-3 (20 g, 46.5 mmol) was dissolved in 0.2 L of tetrahydrofuran (THF) in a nitrogen environment, 4-chloro-2,6-diphenylpyridine (12.4 g, 46.5 mmol) and tetrakis(triphenylphosphine)palladium (0.54 g, 0.47 mmol) were added thereto, and the mixture was agitated. Potassium carbonate (16.1 g, 116 mmol) saturated in water was added thereto, and the resulting mixture was heated and refluxed at 80° C. for 17 hours. When the reaction was complete, water was added to the reaction solution was extracted with dichloromethane (DCM) and treated with anhydrous MgSO$_4$ to remove moisture, and the obtained product was filtered and concentrated under a reduced pressure. The obtained residue was separated and purified through flash column chromatography, obtaining the compound 13 (18.9 g, 76%).

HRMS (70 eV, EI+): m/z calcd for C41H27N: 533.2143. found: 533.

Elemental Analysis: C, 92%; H, 5%

The compound 1-3 (20 g, 46.5 mmol) was dissolved in 0.2 L of tetrahydrofuran (THF) in a nitrogen environment, 2-chloro-4,6-diphenylpyrimidine (12.4 g, 46.5 mmol) and tetrakis(triphenylphosphine)palladium (0.54 g, 0.47 mmol) were added thereto, and the mixture was agitated. Potassium carbonate (16.1 g, 116 mmol) saturated in water was added thereto, and the resulting mixture was heated and refluxed at 80° C. for 15 hours. When the reaction was complete, water was added to the reaction solution, the mixture was extracted with dichloromethane (DCM) and then, treated with anhydrous MgSO4 to remove moisture therefrom, and the obtained product was filtered and concentrated under a reduced pressure. The obtained residue was separated and purified through flash column chromatography, obtaining the compound 14 (20.4 g, 82%).

HRMS (70 eV, EI+): m/z calcd for C40H26N2: 534.2096. found: 534.

Elemental Analysis: C, 90%; H, 5%

Synthesis Example 14

Synthesis of Compound 14

Synthesis Example 15

Synthesis of Compound 15

[Reaction Scheme 14]

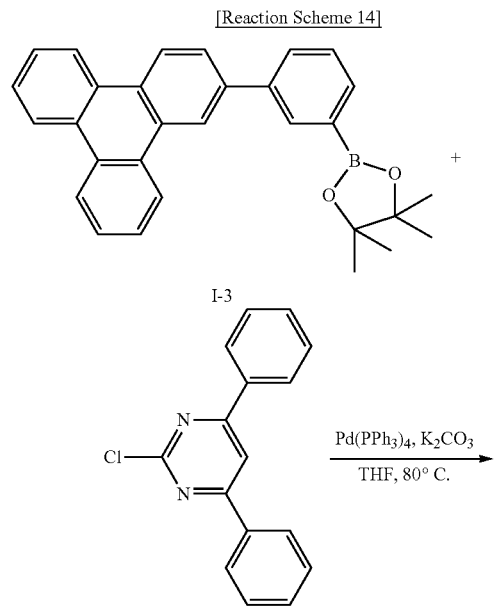

[Reaction Scheme 15]

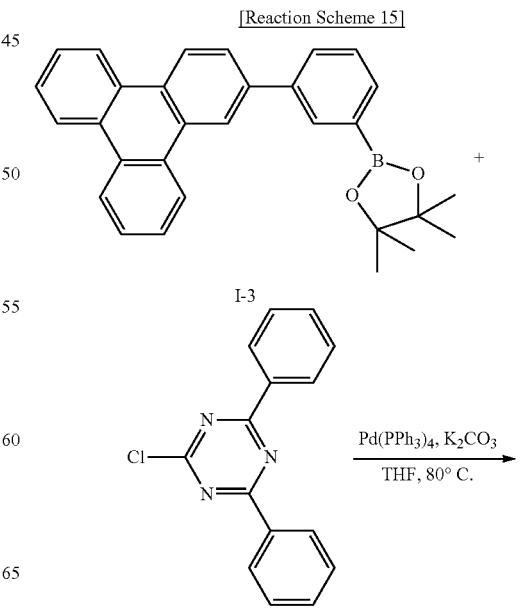

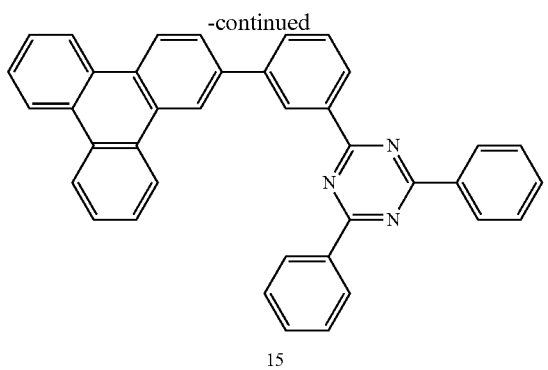

The compound 1-3 (20 g, 46.5 mmol) was dissolved in 0.2 L of tetrahydrofuran (THF) in a nitrogen environment, 2-chloro-4,6-diphenyl-1,3,5-triazine (12.4 g, 46.5 mmol) and tetrakis(triphenylphosphine)palladium (0.54 g, 0.47 mmol) were added thereto, and the mixture was agitated. Potassium carbonate (16.1 g, 116 mmol) saturated in water was added thereto, and the resulting mixture was heated and refluxed at 80° C. for 20 hours. When the reaction was complete, water was added to the reaction solution, the mixture was extracted with dichloromethane (DCM) and then, treated with anhydrous MgSO$_4$ to remove moisture therefrom, and the obtained product was filtered and concentrated under a reduced pressure. This obtained residue was separated and purified through flash column chromatography, obtaining the compound 15 (21.2 g, 85%).

HRMS (70 eV, El+): m/z calcd for C39H25N3: 535.2048. found: 535.

Elemental Analysis: C, 87%; H, 5%

Synthesis Example 16

Synthesis of Compound 24

[Reaction Scheme 16]

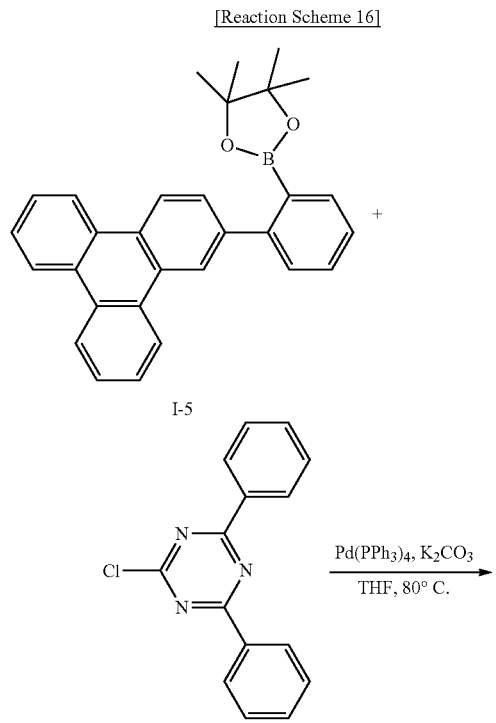

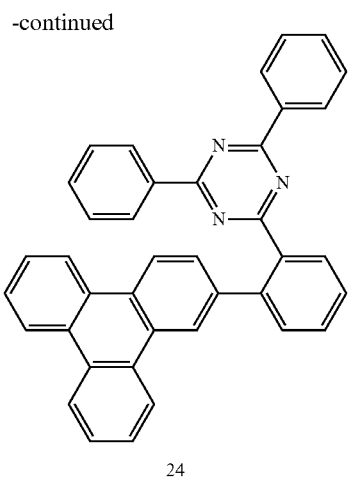

The compound 1-5 (20 g, 46.5 mmol) was dissolved in 0.2 L of tetrahydrofuran (THF) in a nitrogen environment, 2-chloro-4,6-diphenyl-1,3,5-triazine (12.4 g, 46.5 mmol) and tetrakis(triphenylphosphine)palladium (0.54 g, 0.47 mmol) were added thereto, and the mixture was agitated. Potassium carbonate (16.1 g, 116 mmol) saturated in water were added thereto, and the resulting mixture were heated and refluxed at 80° C. for 27 hours. When the reaction was complete, water was added to the reaction solution, the mixture was extracted with dichloromethane (DCM) and treated with anhydrous MgSO$_4$ to remove moisture, and the obtained product was filtered and concentrated under a reduced pressure. The obtained residue was separated and purified through flash column chromatography, obtaining the compound 24 (19.7 g, 79%).

HRMS (70 eV, El+): m/z calcd for C39H25N3: 535.2048. found: 535.

Elemental Analysis: C, 87%; H, 5%

Synthesis Example 17

Synthesis of Compound 33

[Reaction Scheme 17]

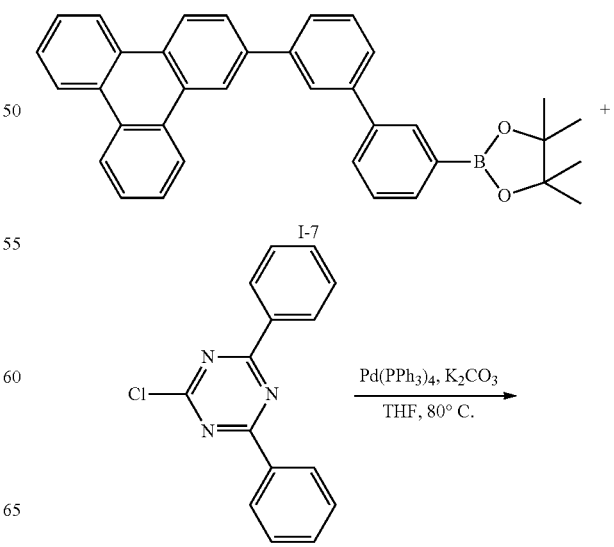

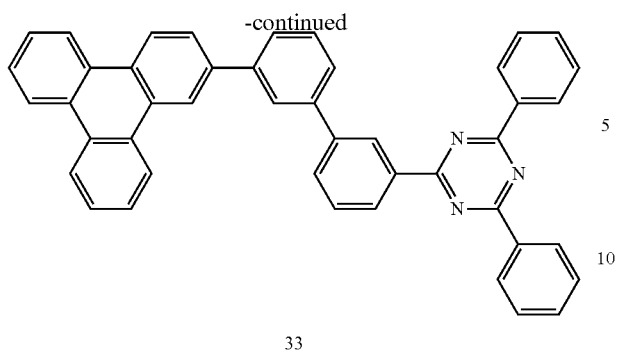

33

The compound 1-7 (20 g, 39.5 mmol) was dissolved in 0.2 L of tetrahydrofuran (THF) in a nitrogen environment, 2-chloro-4,6-diphenyl-1,3,5-triazine (10.6 g, 39.5 mmol) and tetrakis(triphenylphosphine)palladium (0.46 g, 0.4 mmol) were added thereto, and the mixture was agitated. Potassium carbonate (13.6 g, 98.8 mmol) saturated in water was added thereto, and the mixture was heated and refluxed at 80° C. for 23 hours. When the reaction was complete, water was added to the reaction solution, and the mixture was extracted with dichloromethane (DCM) and then, treated with anhydrous MgSO$_4$ to remove moisture therefrom, and the obtained product was filtered and concentrated under a reduced pressure. The obtained residue was separated and purified through flash column chromatography, obtaining the compound 33 (17.9 g, 74%).

HRMS (70 eV, El+): m/z calcd for C45H29N3: 611.2361. found: 611.

Elemental Analysis: C, 88%; H, 5%

Synthesis Example 18

Synthesis of Compound 69

[Reaction Scheme 18]

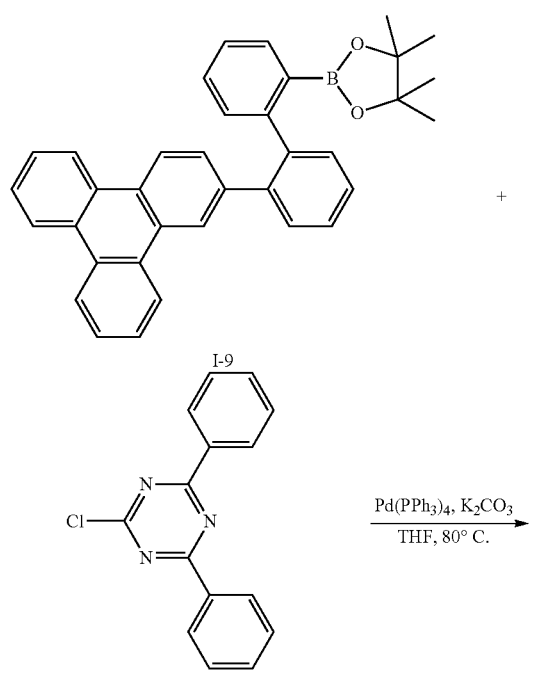

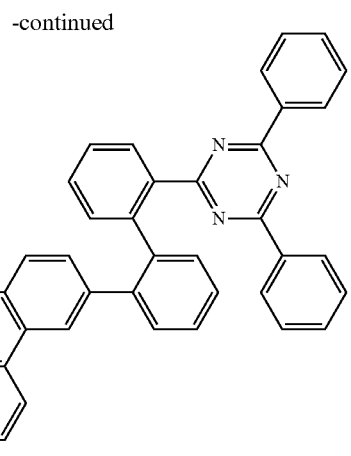

69

The compound 1-9 (20 g, 39.5 mmol) was dissolved in 0.2 L of tetrahydrofuran (THF) in a nitrogen environment, 2-chloro-4,6-diphenyl-1,3,5-triazine (10.6 g, 39.5 mmol) and tetrakis(triphenylphosphine)palladium (0.46 g, 0.4 mmol) were added thereto, and the mixture was agitated. Potassium carbonate (13.6 g, 98.8 mmol) saturated in water was added thereto, and the resulting mixture was heated and refluxed at 80° C. for 32 hours. When the reaction was complete, water was added to the reaction solution, the mixture was extracted with dichloromethane (DCM) and then, treated with anhydrous MgSO$_4$ to remove moisture therefrom, and the obtained product was filtered and concentrated under a reduced pressure. This obtained residue was separated and purified through flash column chromatography, obtaining the compound 69 (15.2 g, 63%).

HRMS (70 eV, El+): m/z calcd for C45H29N3: 611.2361. found: 611.

Elemental Analysis: C, 88%; H, 5%

Synthesis Example 19

Synthesis of Compound 87

[Reaction Scheme 19]

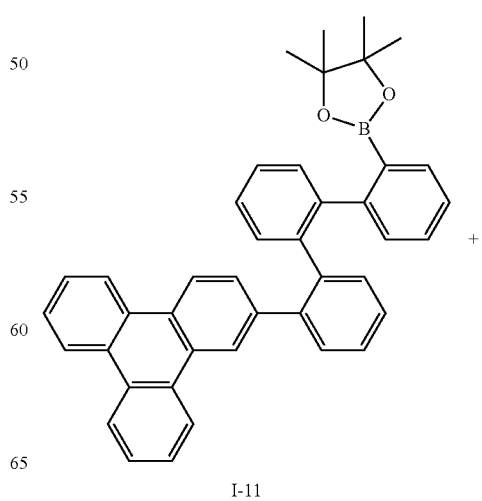

I-11

-continued

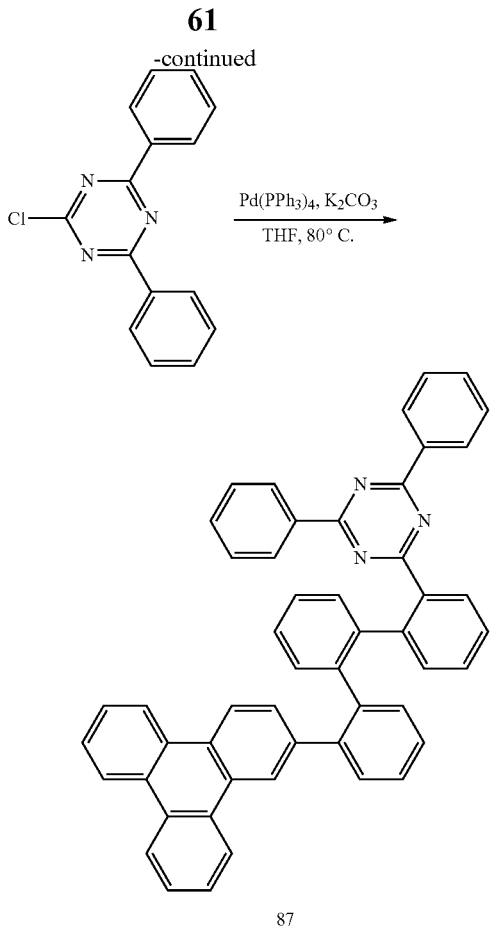

87

The compound 1-11 (20 g, 34.3 mmol) was dissolved in 0.15 L of tetrahydrofuran (THF) in a nitrogen environment, 2-chloro-4,6-diphenyl-1,3,5-triazine (9.19 g, 34.3 mmol) and tetrakis(triphenylphosphine)palladium (0.4 g, 0.34 mmol) were added thereto, and the mixture was agitated. Potassium carbonate (11.9 g, 85.8 mmol) saturated in water was added thereto, and the resulting mixture was heated and refluxed at 80° C. for 29 hours. When the reaction was complete, water was added to the reaction solution, the resulting mixture was extracted with dichloromethane (DCM) and then, treated with anhydrous MgSO$_4$ to remove moisture therefrom, and the obtained product was filtered and concentrated under a reduced pressure. The obtained residue was separated and purified through flash column chromatography, obtaining the compound 87 (16.3 g, 69%).

HRMS (70 eV, EI+): m/z calcd for C51H33N3: 687.2674. found: 687.

Elemental Analysis: C, 89%; H, 5%

Manufacture of Organic Light Emitting Diode

Example 1

The compound 1 obtained in Synthesis Example 12 was used as a host of an emission layer, and Ir(PPy)3 was used as a dopant of an emission layer to manufacture an organic light emitting diode.

A 1000 Å-thick ITO was used as an anode, and a 1000 Å-thick aluminum (Al) was used as a cathode. Specifically, an organic light emitting diode was manufactured by manufacturing the anode by cutting an ITO glass substrate having 15 Ω/cm$^2$ of sheet resistance into a size of 50 mm×50 mm×0.7 mm and cleaning with a ultrasonic wave in acetone, isopropyl alcohol, and pure water respectively for 15 minutes and with UV ozone for 30 minutes.

On the substrate upper, a 800 Å-thick hole transport layer (HTL) was formed by depositing N4,N4'-di(naphthalen-1-yl)-N4,N4'-diphenylbiphenyl-4,4'-diamine (NPB) (80 nm) with a vacuum degree of 650×10$^{-7}$ Pa at a deposition speed ranging from 0.1 to 0.3 nm/s. Subsequently, a 300 Å-thick emission layer was formed by vacuum-depositing the compound 1 obtained in Synthesis Example 12 as a host and Ir(PPy)3 as a phosphorescent dopant. Herein, 7 wt % of the phosphorescent dopant was deposited by adjusting a depositing rate of the phosphorescent dopant based on 100 wt % of the total amount of the emission layer.

On the emission layer, a 50 Å-thick hole blocking layer was formed by using bis(2-methyl-8-quinolinolate)-4-(phenylphenolato)aluminium (BAlq) under the same deposition condition. Subsequently, a 200 Å-thick electron transport layer (ETL) was formed by depositing Alq3 under the same vacuum deposition condition. LiF and Al were sequentially deposited to from a cathode on the electron transport layer (ETL), manufacturing an organic light emitting diode.

Finally, the organic light emitting diode has a structure of ITO/NPB (80 nm)/EML (compound 1 (93 wt %)+Ir(PPy)3 (7 wt %), 30 nm)/Balq (5 nm)/Alq3 (20 nm)/LiF (1 nm)/Al (100 nm).

Example 2

An organic light emitting diode was manufactured according to the same method as Example 1 except for using the compound 13 of Synthesis Example 13, instead of the compound 1 of Synthesis Example 12, as a host of the emission layer.

Example 3

An organic light emitting diode was manufactured according to the same method as Example 1 except for using the compound 14 of Synthesis Example 14, instead of the compound 1 of Synthesis Example 12, as a host of the emission layer.

Example 4

An organic light emitting diode was manufactured according to the same method as Example 1 except for using the compound 15 of Synthesis Example 15, instead of the compound 1 of Synthesis Example 12, as a host of the emission layer.

Example 5

An organic light emitting diode was manufactured according to the same method as Example 1 except for using the compound 24 of Synthesis Example 16, instead of the compound 1 of Synthesis Example 12, as a host of the emission layer.

Example 6

An organic light emitting diode was manufactured according to the same method as Example 1 except for using the compound 33 of Synthesis Example 17, instead of the compound 1 of Synthesis Example 12, as a host of the emission layer.

Example 7

An organic light emitting diode was manufactured according to the same method as Example 1 except for using the compound 69 of Synthesis Example 18, instead of the compound 1 of Synthesis Example 12, as a host of the emission layer.

Example 8

An organic light emitting diode was manufactured according to the same method as Example 1 except for using the compound 87 of Synthesis Example 19, instead of the compound 1 of Synthesis Example 12, as a host of the emission layer.

Comparative Example 1

An organic light emitting diode was manufactured according to the same method as Example 1 except for using the CBP having the following chemical formula, instead of the compound 1 of Synthesis Example 12, as a host of the emission layer.

Comparative Example 2

An organic light emitting diode was manufactured according to the same method as Example 1 except for using the HOST1 having the following chemical formula, instead of the compound 1 of Synthesis Example 12, as a host of the emission layer.

Comparative Example 3

An organic light emitting diode was manufactured according to the same method as Example 1 except for using the HOST2 having the following chemical formula, instead of the compound 1 of Synthesis Example 12, as a host of the emission layer.

Chemical formulae of the NPB, BAlq, CBP, Ir(PPy)3, HOST1 and HOST2 used for manufacture the organic light emitting diode are as follows.

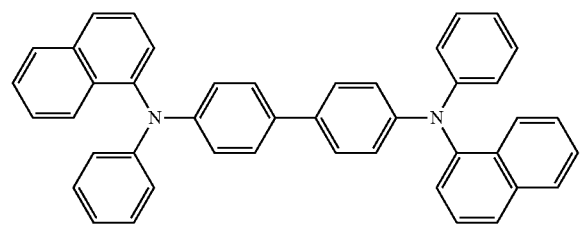

[NPB]

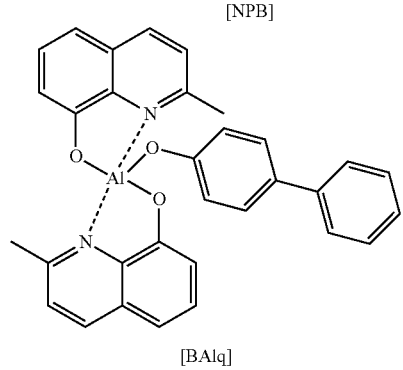

[BAlq]

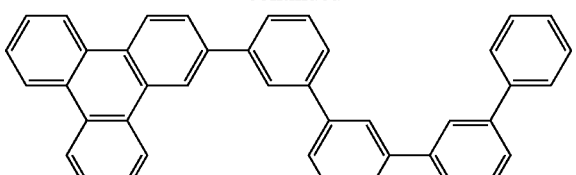

[HOST1]

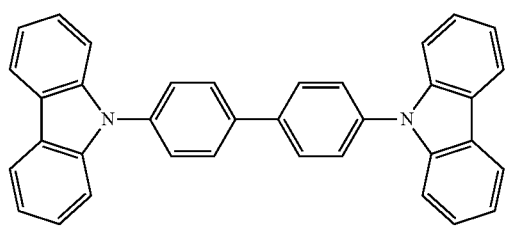

[CBP]

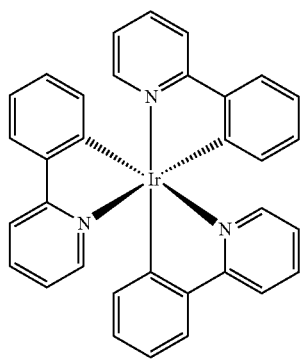

[Ir(PPy)$_3$]

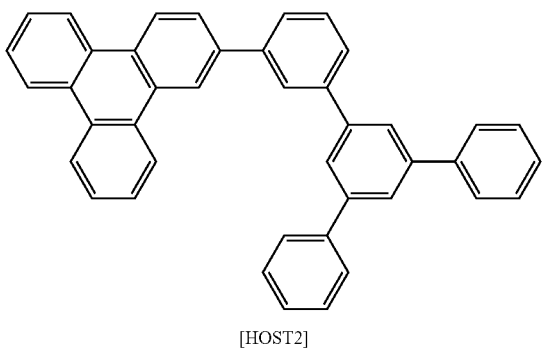

[HOST2]

Evaluation

Current density and luminance changes depending on a voltage and luminous efficiency of each organic light emitting diode according to Examples 1 to 8 and Comparative Examples 1 to 3 were measured.

The measurements were specifically performed in the following method, and the results were provided in the following Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0V to 10V using a luminance meter (Minolta Cs-1000 A).

(3) Measurement of Luminous Efficiency

Current efficiency (cd/A) at the same current density (10 mA/cm2) were calculated by using the luminance, current density, and voltages (V) from the items 1) current density change depending on voltage change and 2) luminance change depending on voltage change.

(4) Measurement of Life-Span

Luminance (cd/m$^2$) was maintained at 5000 cd/m$^2$ and a time at current efficiency (cd/A) decreases to 90% was measured.

TABLE 1

| No. | Compound | Driving voltage (V) | Color (EL color) | Efficiency (cd/A) | 90% life-span (h) At 5000 cd/m$^2$ |
|---|---|---|---|---|---|
| Example 1 | compound 1 | 3.5 | Green | 88.5 | 150 |
| Example 2 | compound 13 | 4.0 | Green | 78.2 | 200 |
| Example 3 | compound 14 | 3.9 | Green | 77.0 | 330 |
| Example 4 | compound 15 | 3.6 | Green | 79.8 | 350 |
| Example 5 | compound 24 | 3.5 | Green | 80.2 | 300 |
| Example 6 | compound 33 | 4.2 | Green | 74.3 | 1,500 |
| Example 7 | compound 69 | 4.4 | Green | 75.5 | 1,550 |
| Example 8 | compound 87 | 4.5 | Green | 70.1 | 2,500 |
| Comparative Example 1 | CBP | 4.8 | Green | 31.4 | 40 |
| Comparative Example 2 | HOST1 | 7.2 | Green | 42.1 | 350 |
| Comparative Example 3 | HOST2 | 6.5 | Green | 55.0 | 100 |

From the Table 1, the organic light emitting diodes according to Examples 1 to 8 showed remarkably improved luminous efficiency and life-span compared with the organic light emitting diodes according to Comparative Examples 1 to 3.

Specifically, the luminescent materials used for the organic light emitting diodes according to Examples 1 to 8 include nitrogen and have a structure for easily accepting electrons unlike the luminescent materials used for the organic light emitting diodes according to Comparative Examples 1 to 3. Accordingly, the organic light emitting diodes according to Examples 1 to 8 showed a lower driving voltage compared with the organic light emitting diodes according to Comparative Examples 1 to 3.

In addition, the luminescent materials used in the organic light emitting diodes according to Examples 1 to 8 had a triphenylene moiety of easily accepting holes and a bipolar structure including a nitrogen-containing ring moiety easily accepting electrons and appropriately balanced a flow between holes and electrons and thus, the organic light emitting diodes according to Examples 1 to 8 showed higher efficiency than the organic light emitting diodes according to Comparative Examples 1 to 3.

In addition, the luminescent materials used for the organic light emitting diodes according to Examples 1 to 8 have a structure of appropriately localizing the triphenylene moiety easily accepting holes and the nitrogen-containing ring moiety easily accepting electrons and controlled a conjugation-system flow and thus, the organic light emitting diodes according to Examples 1 to 8 showed a higher life-span than the organic light emitting diodes according to Comparative Examples 1 or 3. Furthermore, the organic light emitting diodes according to Examples 6, 7, and 8 showed about 3 times or more improved life-span than that according to Comparative Example 2 when their 90% life-spans were compared and also, about 1.6 times or more increased luminous efficiency than that according to Comparative Example 2 despite the life-span improvement.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A luminescent material for an organic optoelectric device, the luminescent material being represented by the Chemical Formula 1:

[Chemical Formula 1]

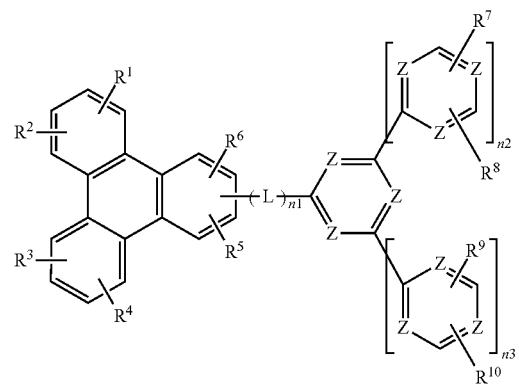

wherein, in Chemical Formula 1, each Z is independently N or CR$^a$, at least two Zs are N, at least two Zs in the Z-containing ring bonded to L or the triphenylene group being N, R$^1$ to R$^{10}$ and R$^a$ are each independently hydrogen, deuterium, a substituted or unsubstituted C1 to C10 alkyl group, a substituted or unsubstituted C6 to C12 aryl group, or a combination thereof, L is a substituted or unsubstituted phenylene group, a substituted or unsubstituted biphenylene group, or a substituted or unsubstituted terphenylene group, n1 to n3 are each independently 0 or 1, and n1+n2+n3≥1.

2. The luminescent material for an organic optoelectric device of claim 1, wherein the luminescent material is represented by Chemical Formula 1-I or Chemical Formula 1-II:

[Chemical Formula 1-I]

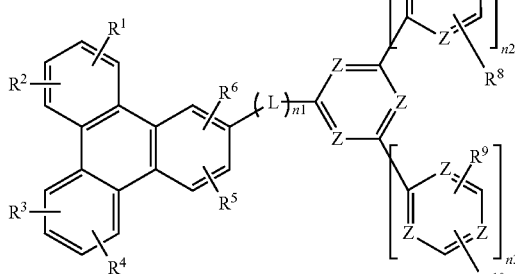

[Chemical Formula 1-II]

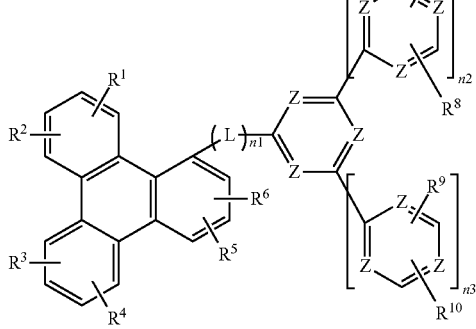

wherein, in Chemical Formula 1-I and 1-II, each Z is independently N or CR$^a$, at least two Zs are N, at least two Zs in the Z-containing ring bonded to L or the triphenylene group being N, R$^1$ to R$^{10}$ and R$^a$ are each independently hydrogen, deuterium, a substituted or unsubstituted C1 to C10 alkyl group, a substituted or unsubstituted C6 to C12 aryl group, or a combination thereof, L is a substituted or unsubstituted phenylene group, a substituted or unsubstituted biphenylene group, or a substituted or unsubstituted terphenylene group, n1 to n3 are each independently 0 or 1, and n1+n2+n3≥1.

3. The luminescent material for an organic optoelectric device of claim 1, wherein L is a substituted or unsubstituted phenylene group having a kink structure, a substituted or unsubstituted biphenylene group having a kink structure, or a substituted or unsubstituted terphenylene group having a kink structure.

4. The luminescent material for an organic optoelectric device of claim 3, wherein L is one of the following substituted or unsubstituted groups

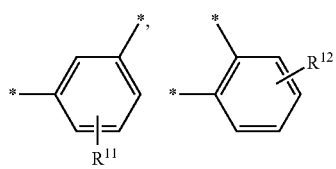

-continued

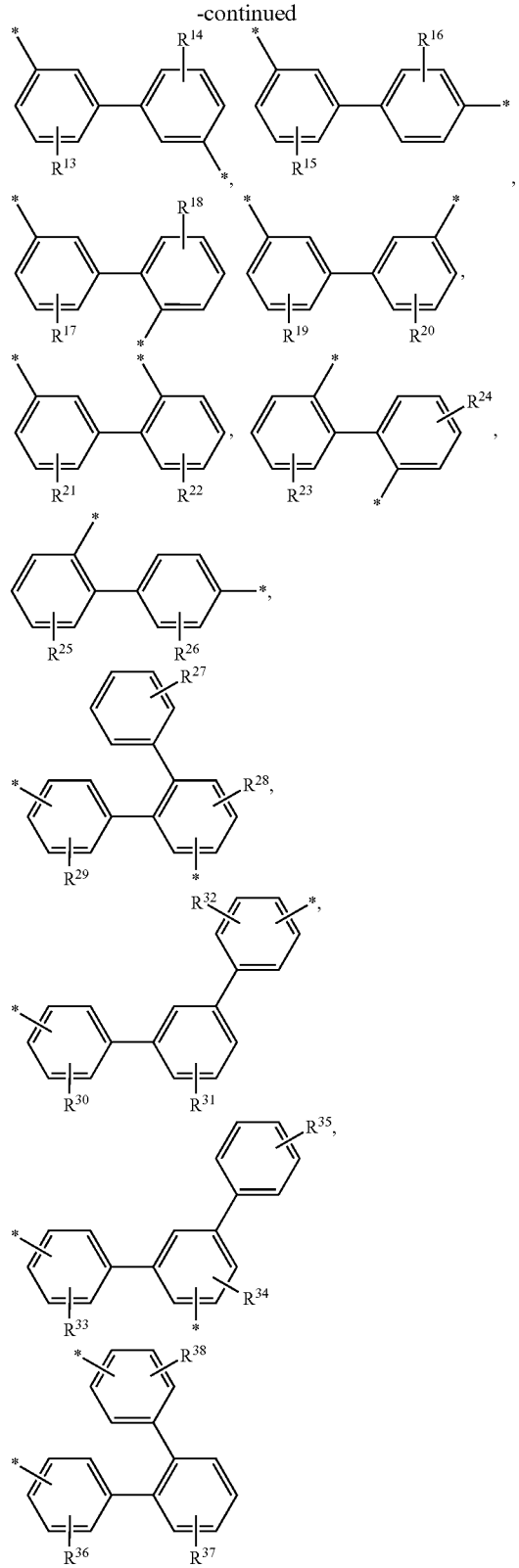

wherein:

R$^{11}$ to R$^{38}$ are each independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof, and

* represents a binding site to a neighboring atom.

5. The luminescent material for an organic optoelectric device of claim 1, wherein the luminescent material includes at least two kink structures.

6. The luminescent material for an organic optoelectric device of claim 1, wherein the luminescent material is represented by Chemical Formula 1a or 1b:

[Chemical Formula 1a]

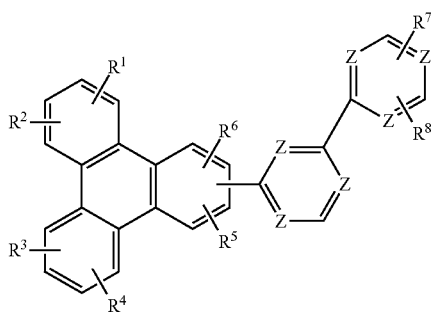

[Chemical Formula 1b]

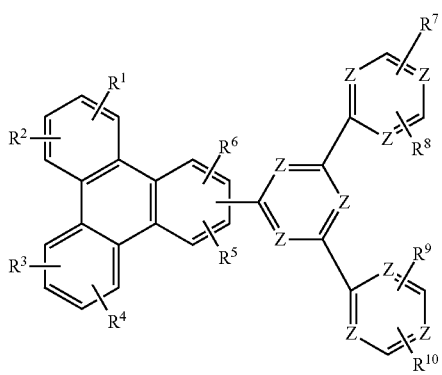

wherein, in Chemical Formula 1a and 1b, each Z is independently N or $CR^a$, at least two Zs are N, at least two Zs in the Z-containing ring bonded to L or the triphenylene group being N, and $R^1$ to $R^{10}$ and $R^a$ are each independently hydrogen, deuterium, a substituted or unsubstituted C1 to C10 alkyl group, a substituted or unsubstituted C6 to C12 aryl group, or a combination thereof.

7. The luminescent material for an organic optoelectric device of claim 1, wherein the luminescent material is represented by one of Chemical Formulae 1c to 1t:

[Chemical Formula 1c]

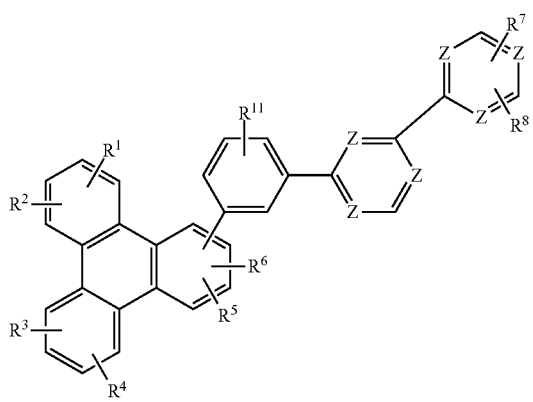

[Chemical Formula 1d]

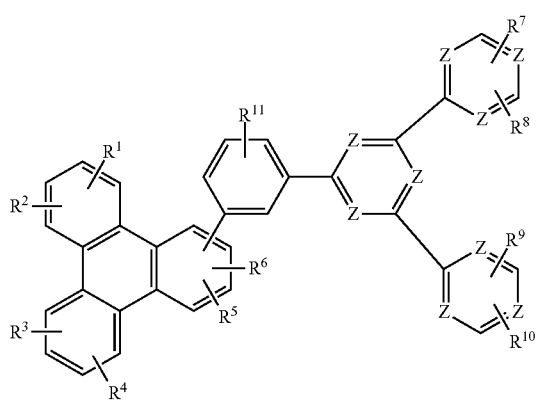

[Chemical Formula 1e]

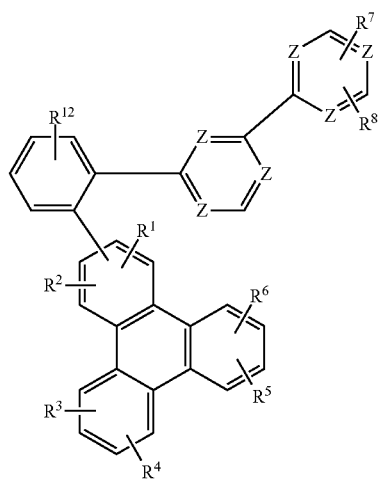

[Chemical Formula 1f]
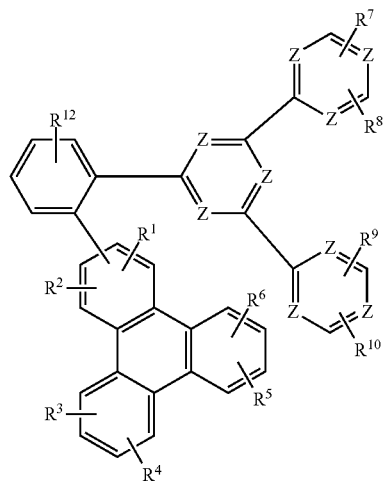
[Chemical Formula 1g]
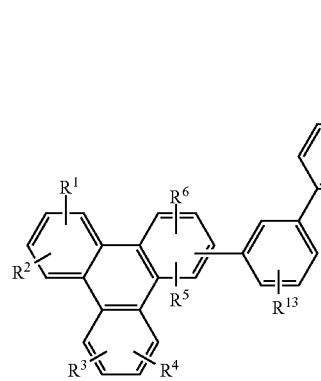
[Chemical Formula 1h]
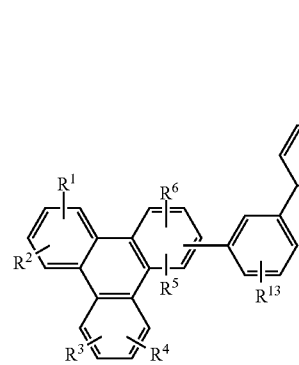
[Chemical Formula 1i]
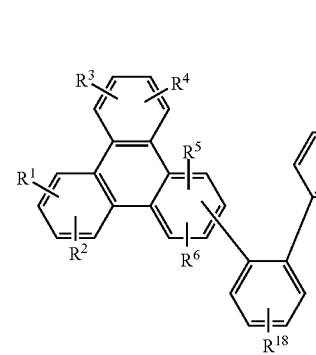
[Chemical Formula 1j]
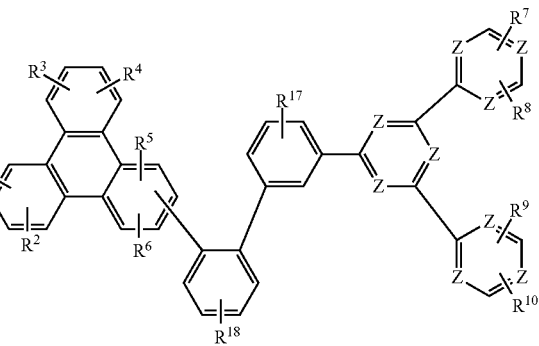
[Chemical Formula 1k]
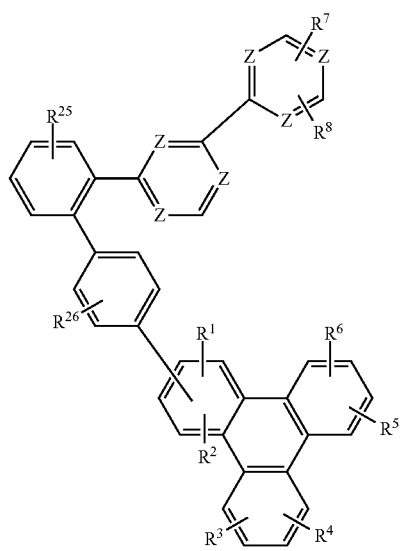
[Chemical Formula 1l]
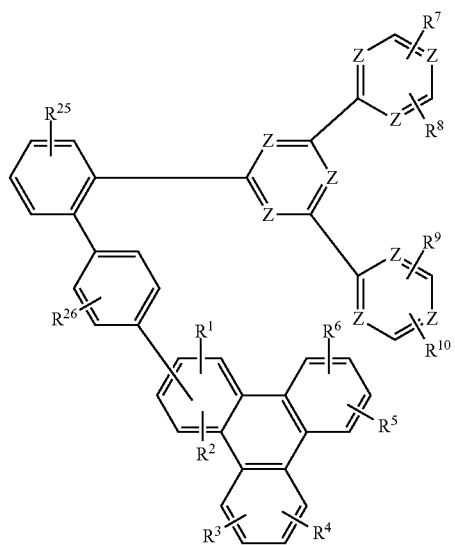

[Chemical Formula 1m]
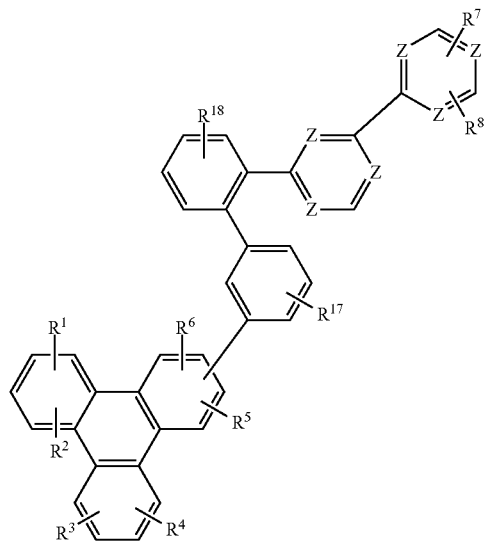
[Chemical Formula 1n]
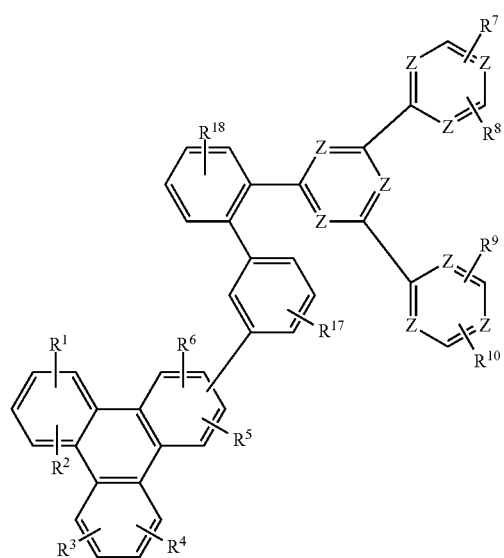
[Chemical Formula 1o]
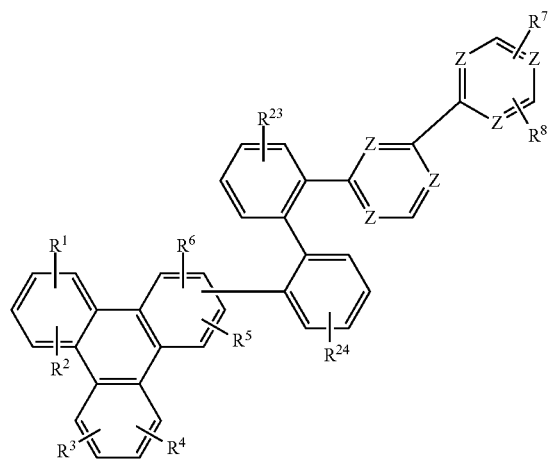
[Chemical Formula 1p]
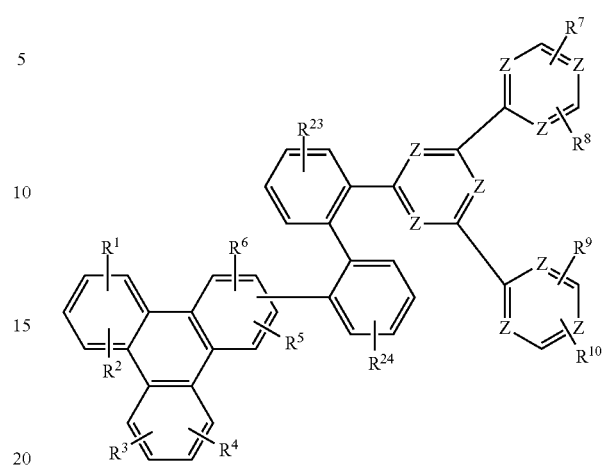
[Chemical Formula 1q]
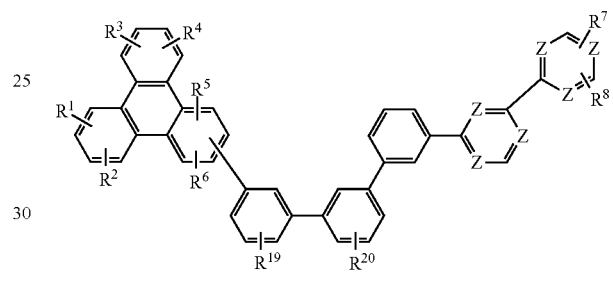
[Chemical Formula 1r]
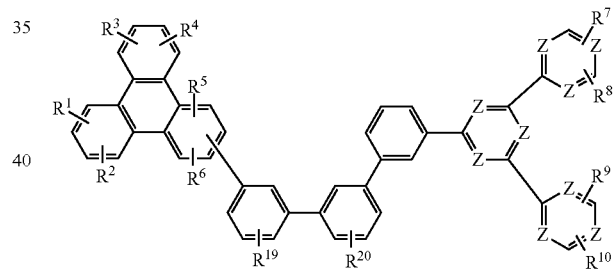
[Chemical Formula 1s]
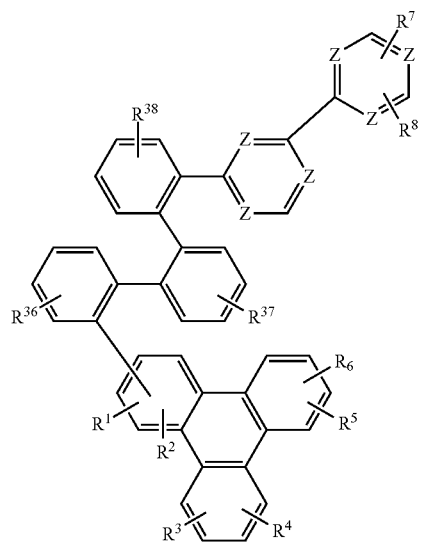

-continued

[Chemical Formula 1t]

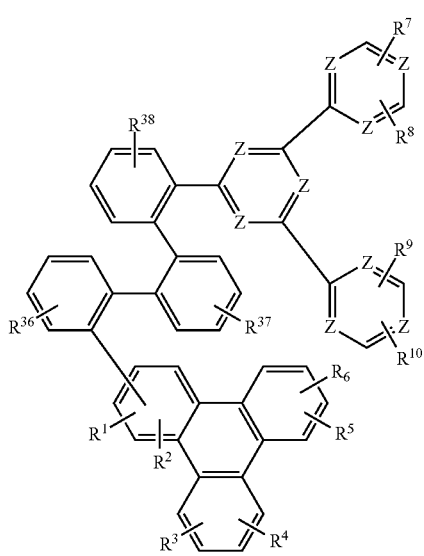

wherein, in Chemical Formulae 1c to 1 t, each Z is independently N or CR$^a$, at least two Zs are N, at least two Zs in the Z-containing ring bonded to L or the triphenylene group being N, R$^1$ to R$^{10}$ and R$^a$ are each independently hydrogen, deuterium, a substituted or unsubstituted C1 to C10 alkyl group, a substituted or unsubstituted C6 to C12 aryl group, or a combination thereof, R$^{11}$ to R$^{14}$, R$^{17}$ to R$^{20}$, R$^{23}$ to R$^{26}$ and R$^{36}$ to R$^{38}$ are each independently hydrogen, deuterium, a substituted or unsubstituted C1 to C10 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C6 to C30 heteroarylamine group, a substituted or unsubstituted C1 to C30 alkoxy group, a halogen, a halogen-containing group, a cyano group, a hydroxyl group, an amino group, a nitro group, a carboxyl group, a ferrocenyl group, or a combination thereof.

8. The luminescent material for an organic optoelectric device of claim 1, wherein the luminescent material includes one of the following compounds:

1

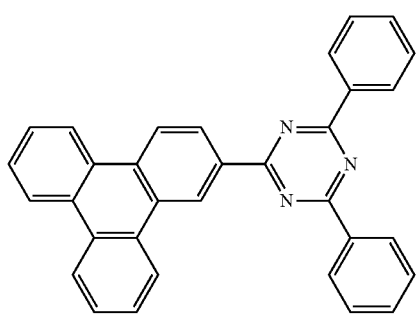

2

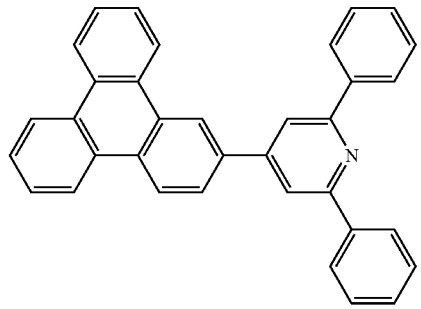

3

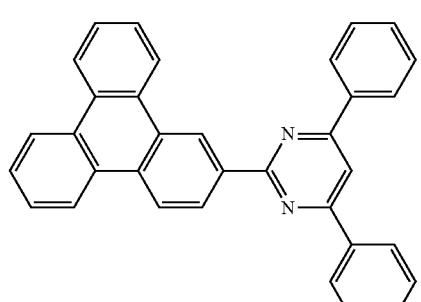

4

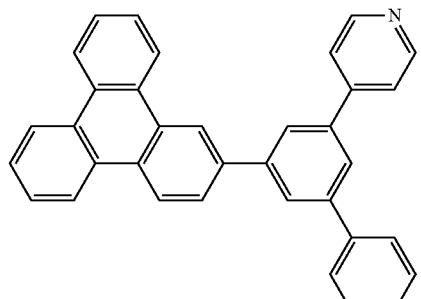

5

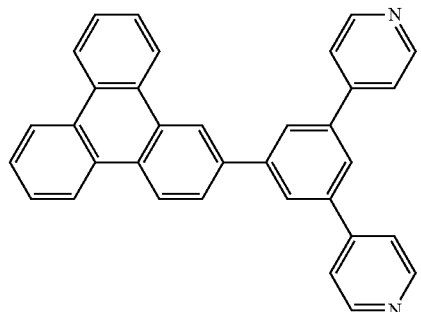

6

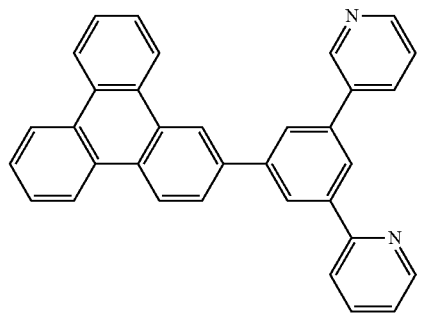

7
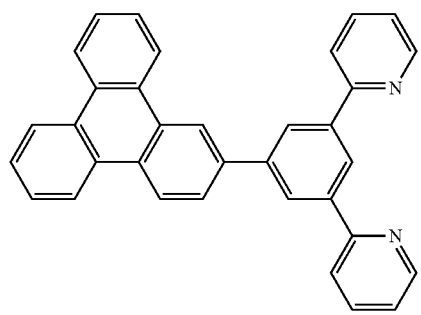
8
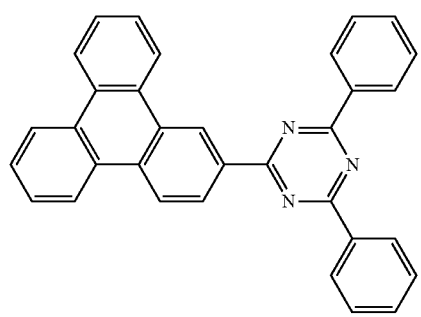
9
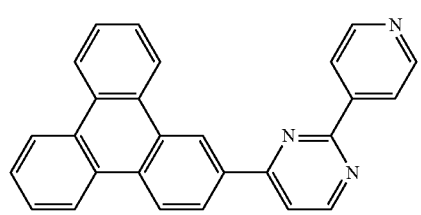
10
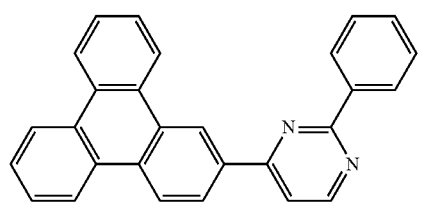
11
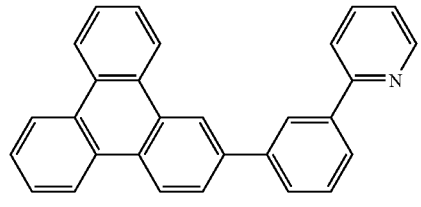
12
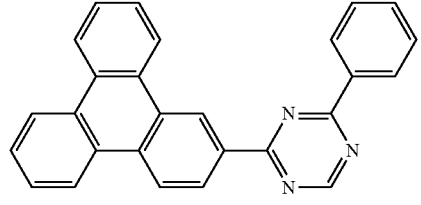
13
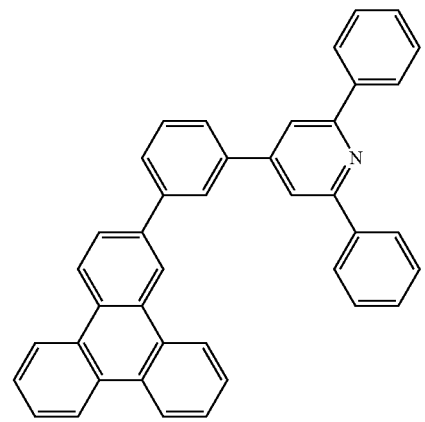
14
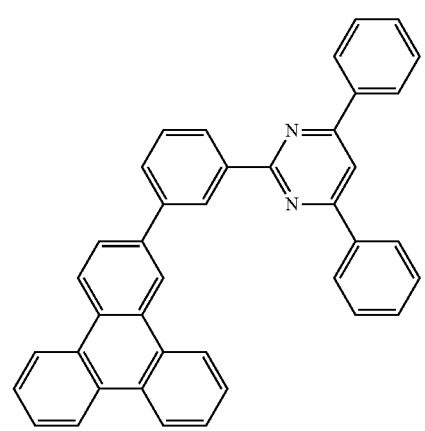
15
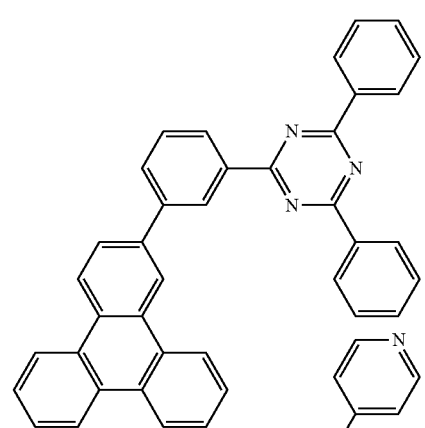
16
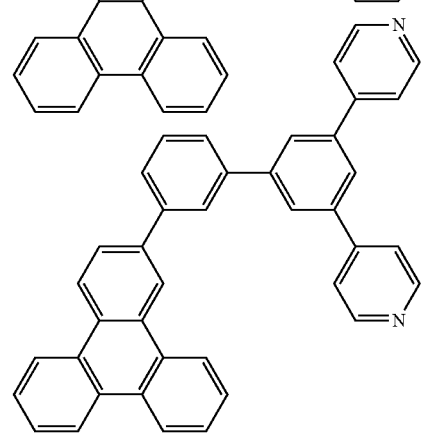

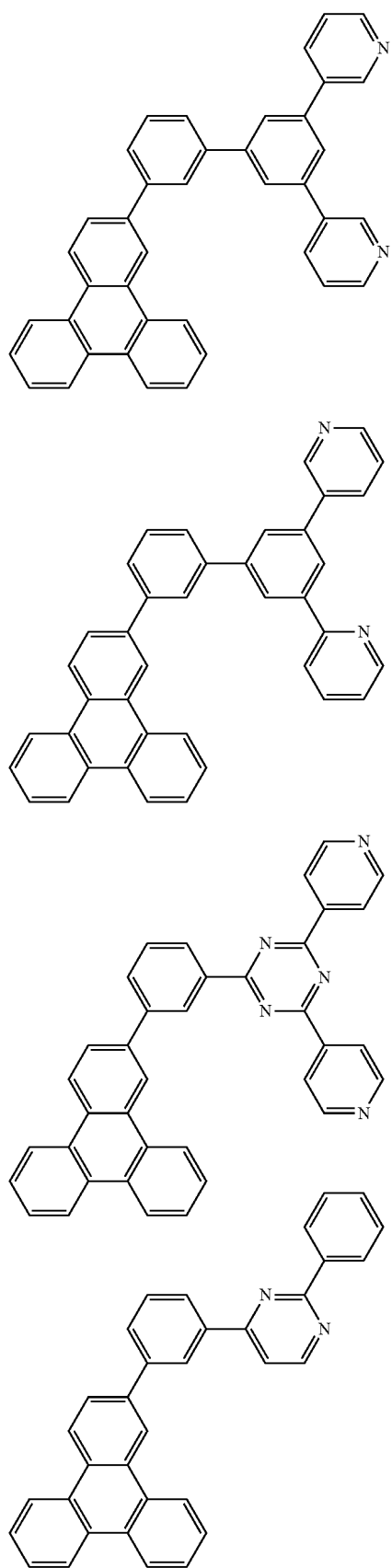
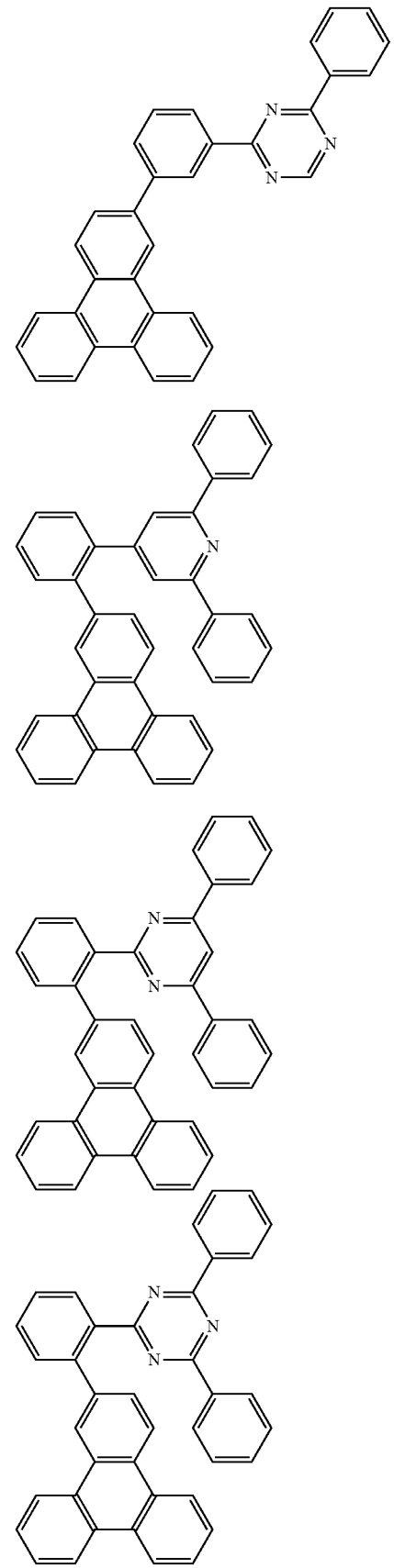

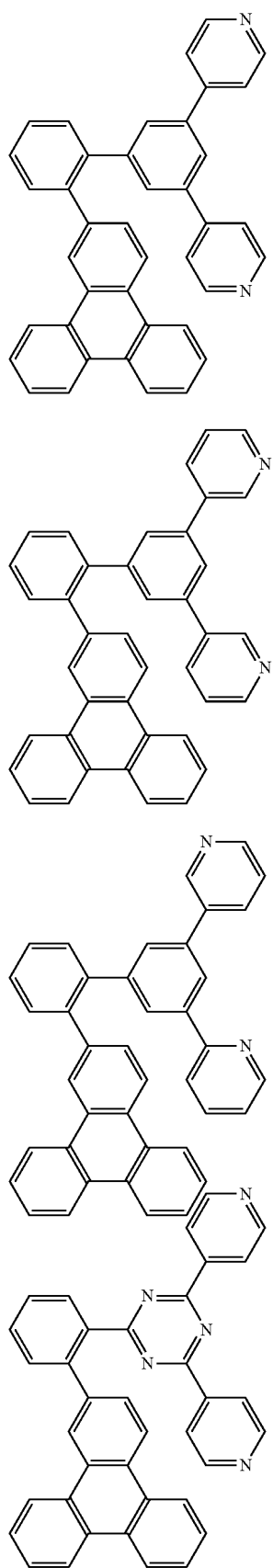
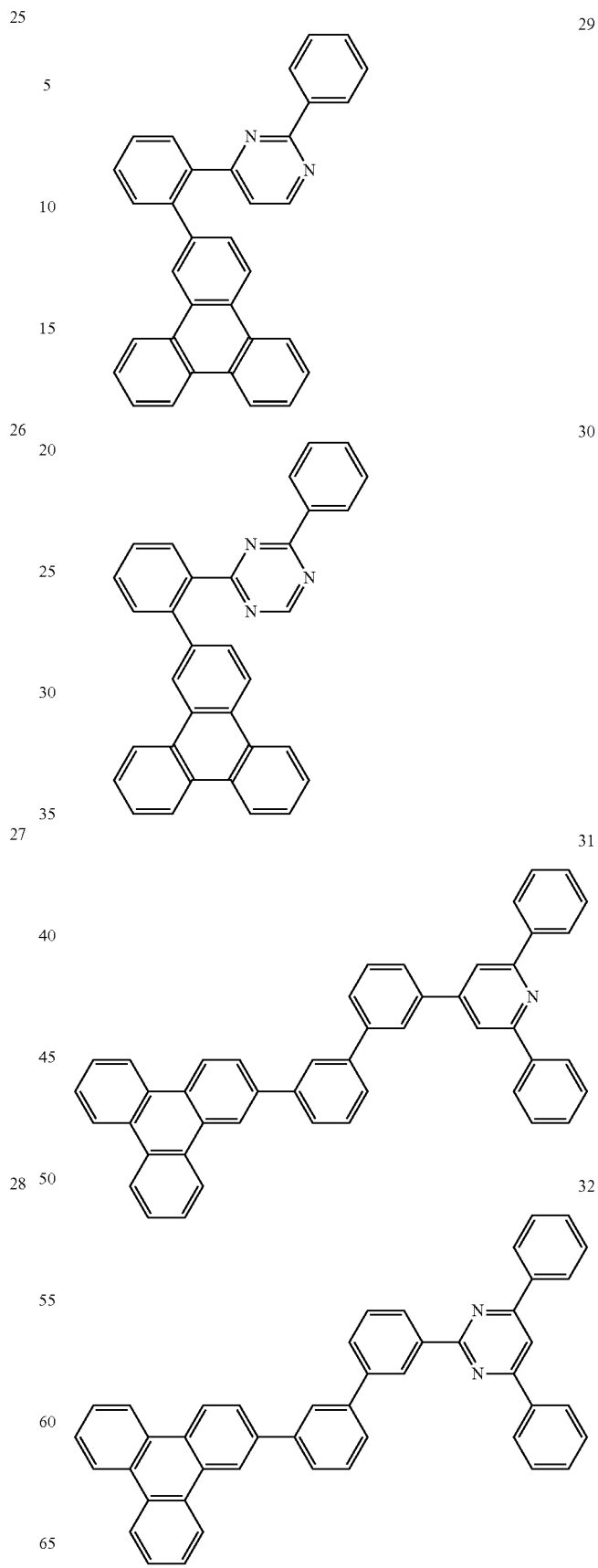

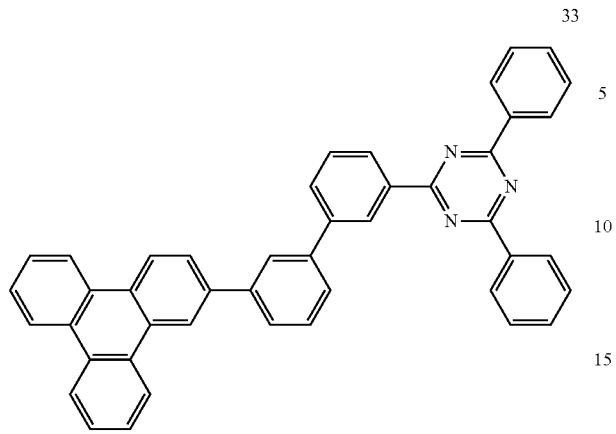
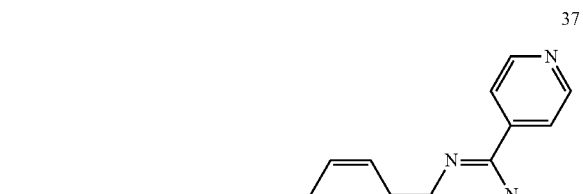
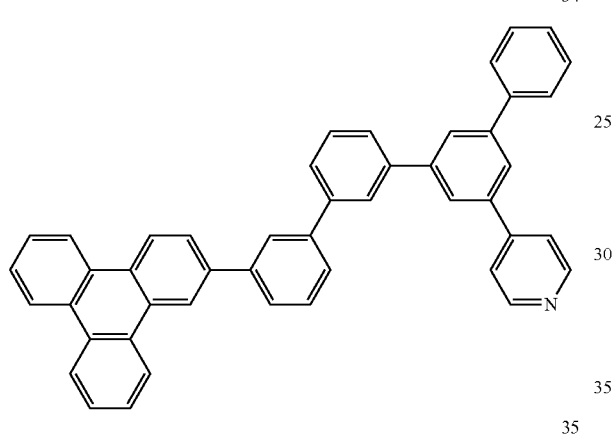
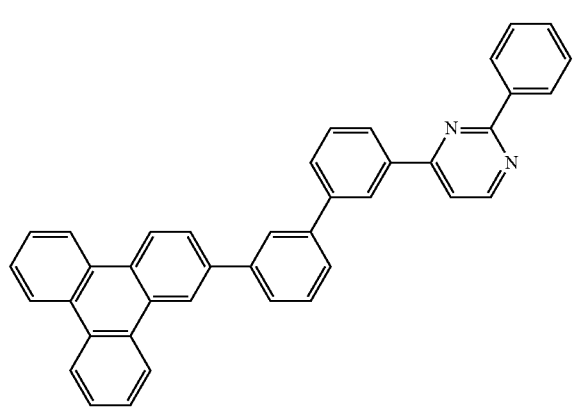
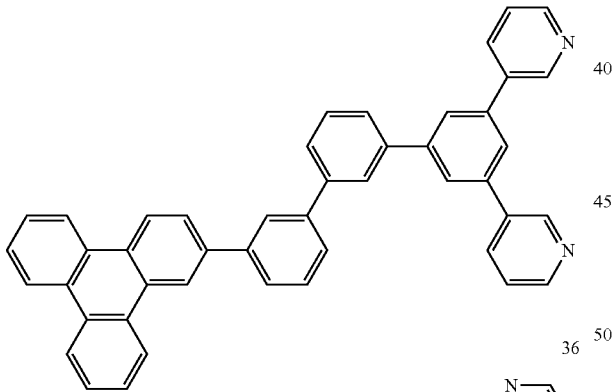
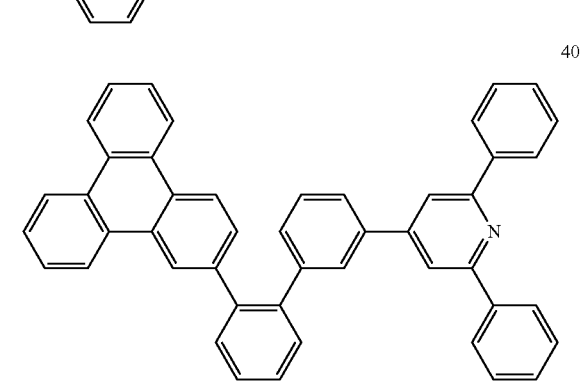

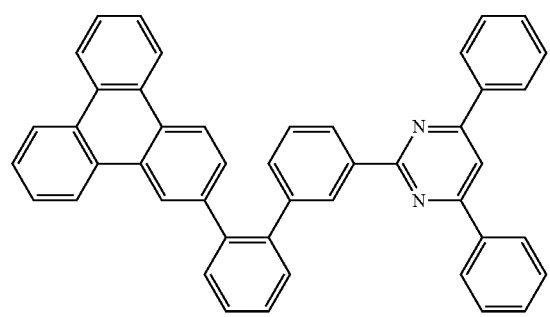
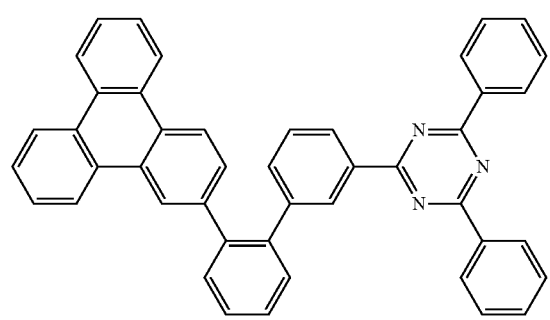
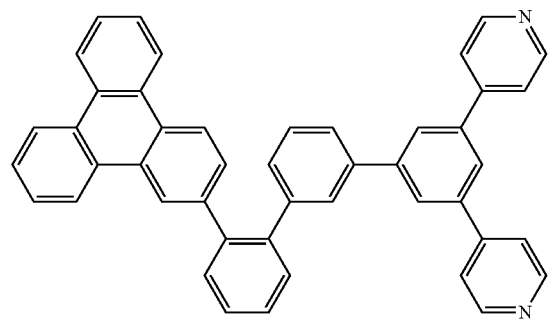
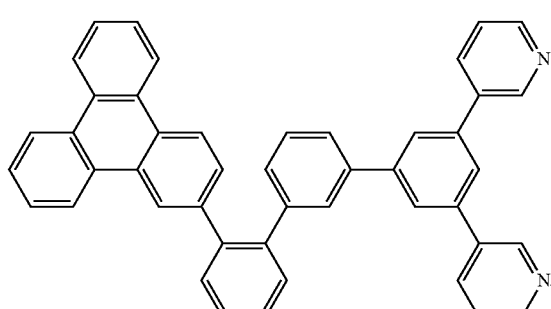
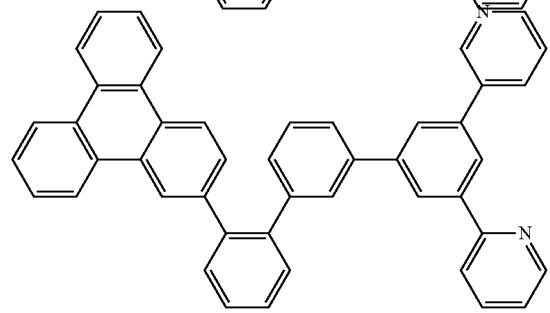
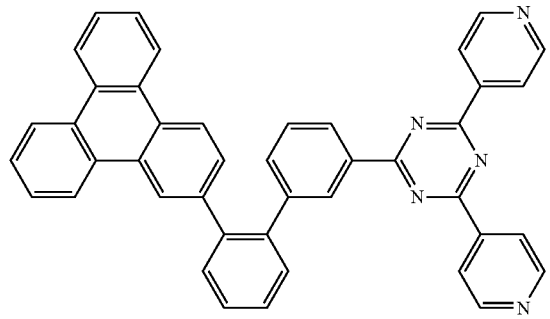
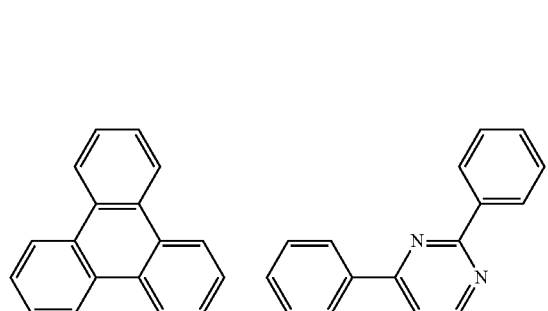
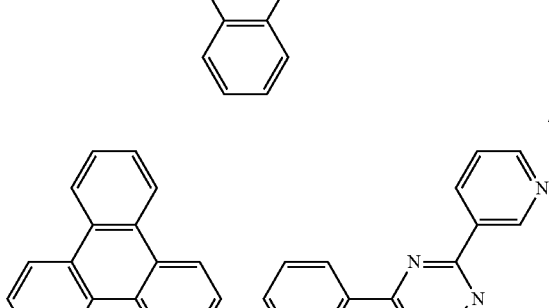
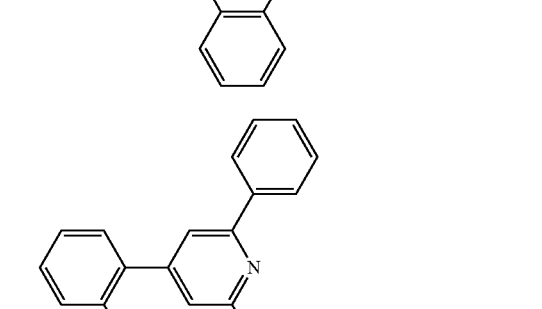
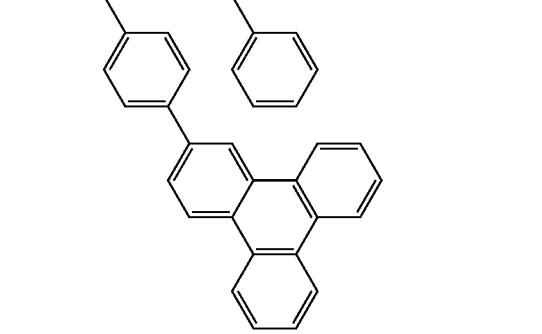

87 50

51

52

88 53

54

55

-continued
56
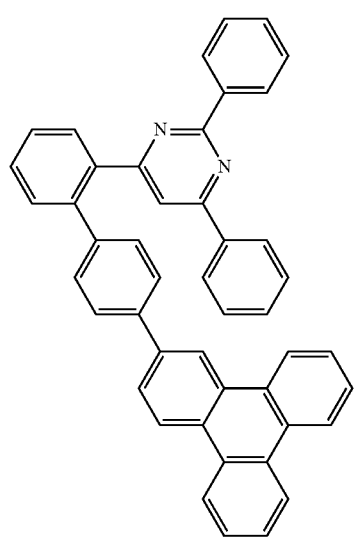
57
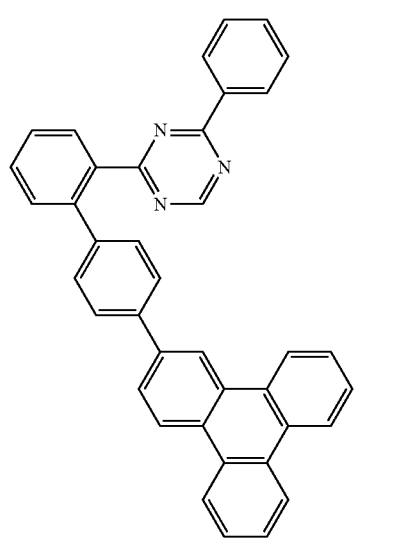
58
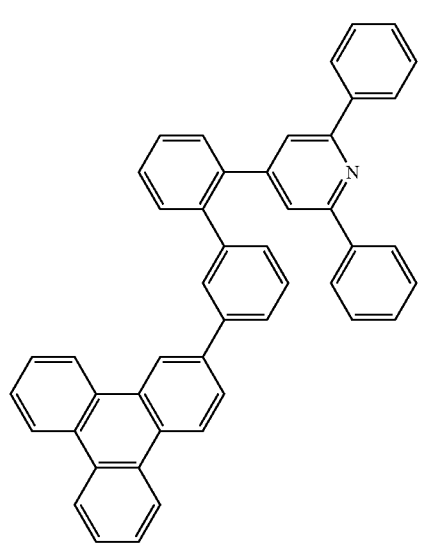
-continued
59
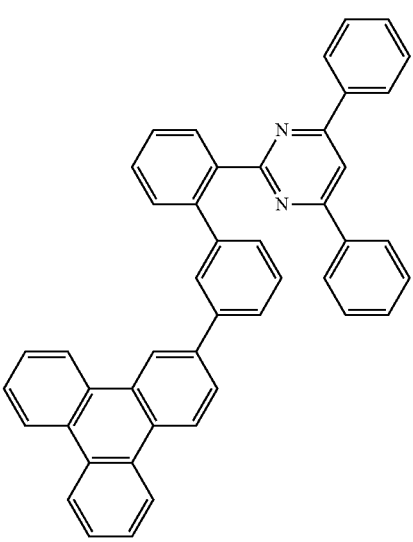
60
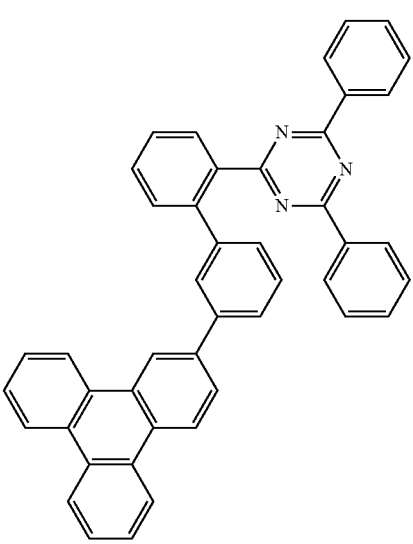
61
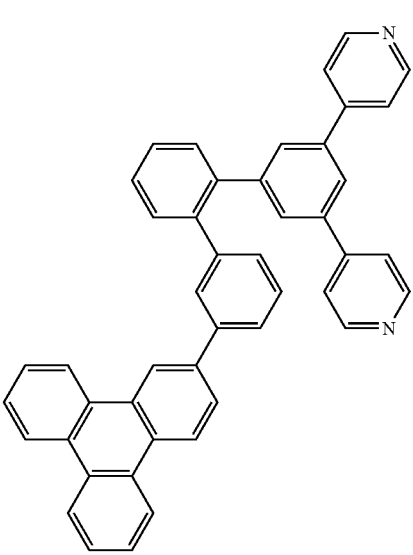

62
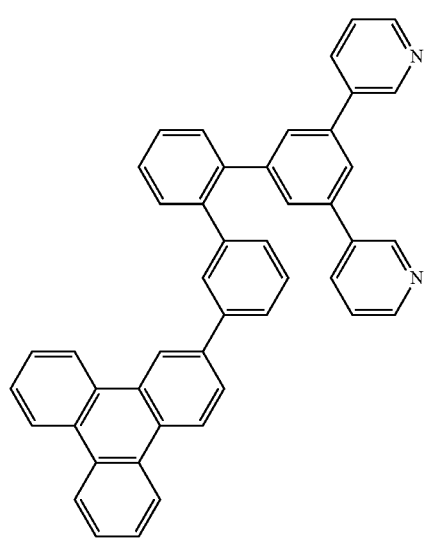
63
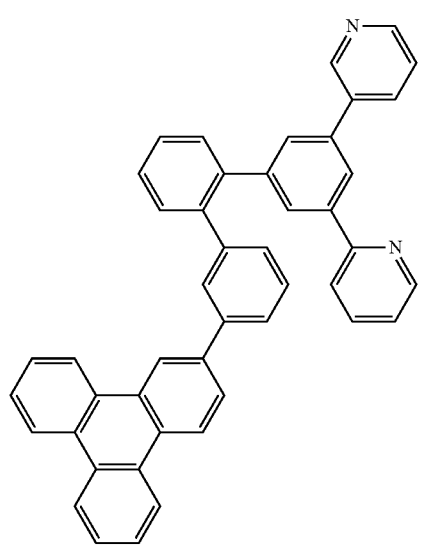
64
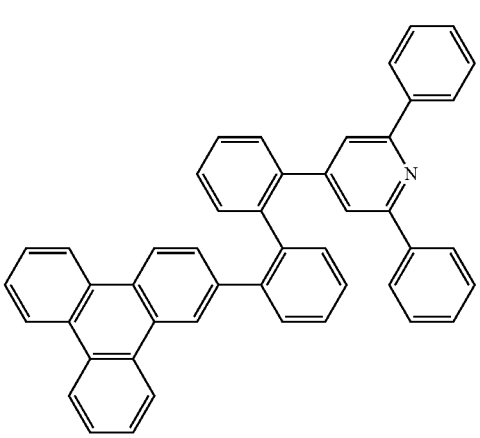
65
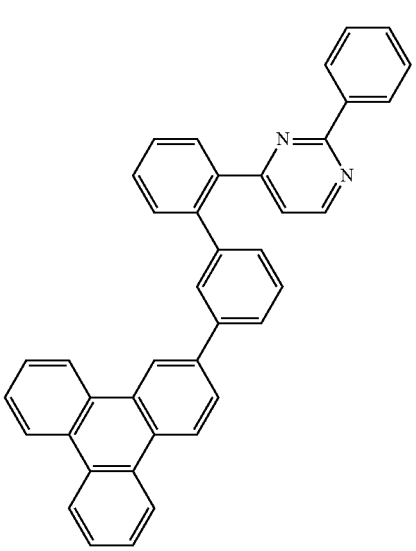
66
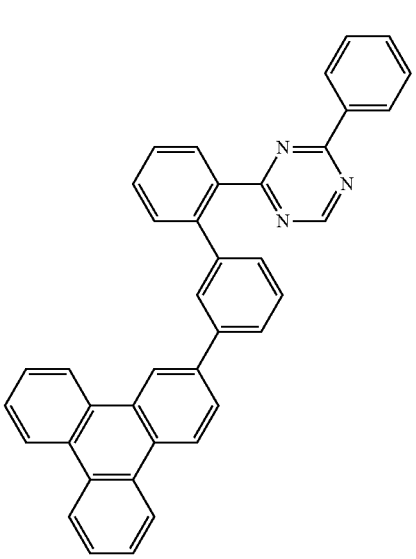
67

-continued
68
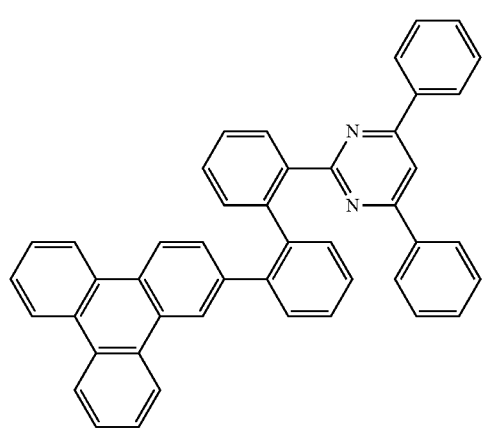
69
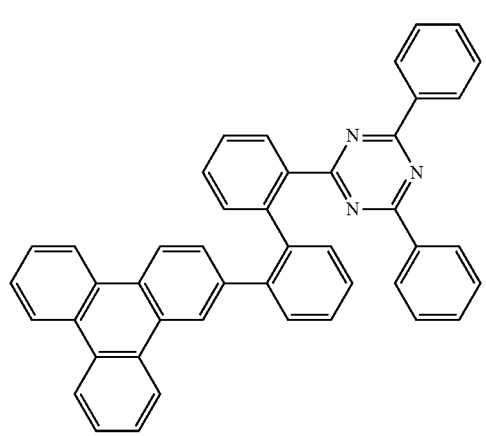
70
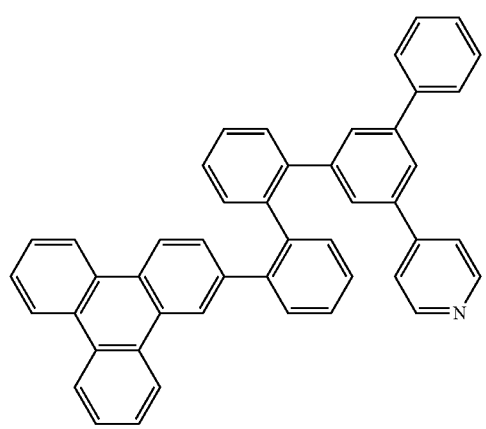
-continued
71
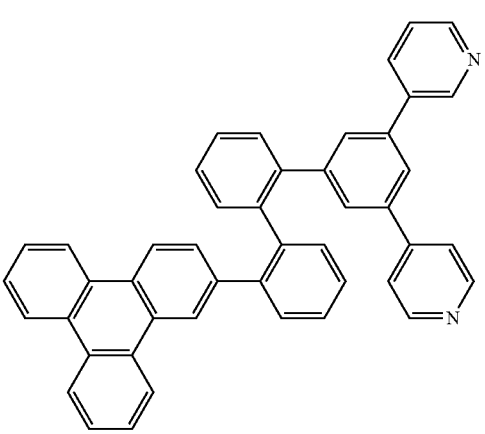
72
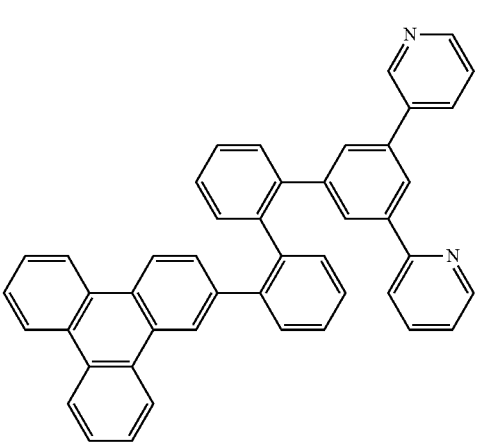
73
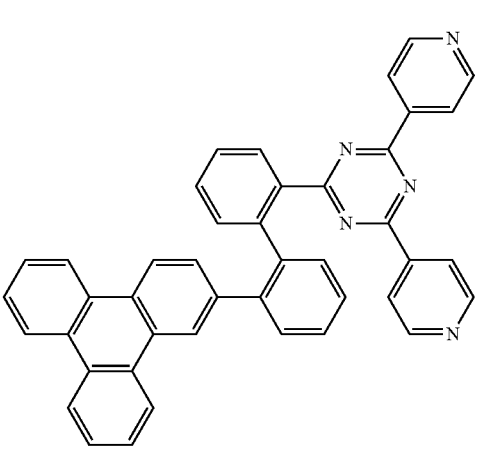

74
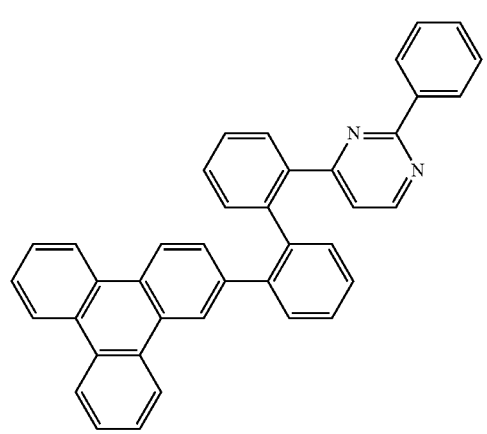
75
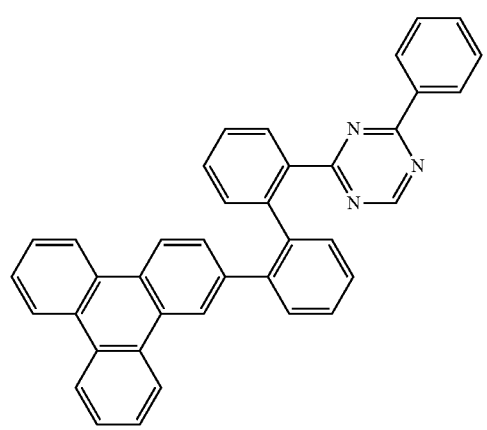
76
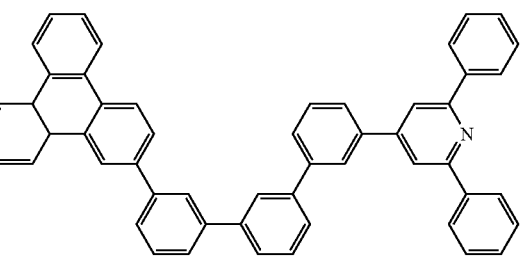
77
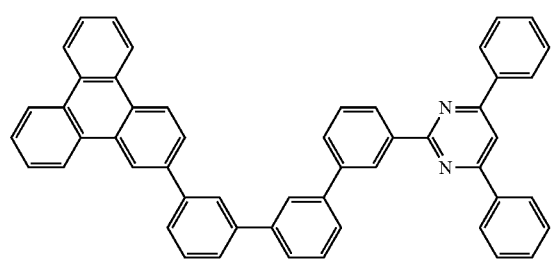
78
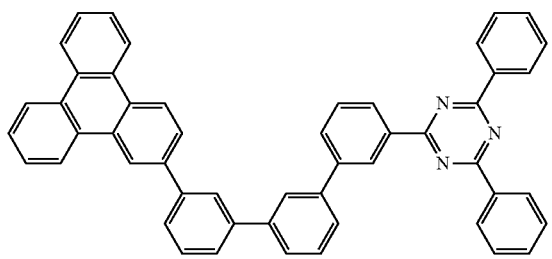
79
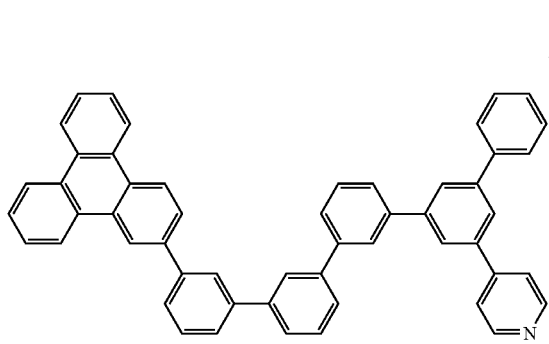
80
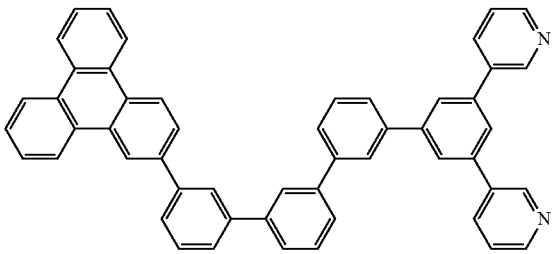
81
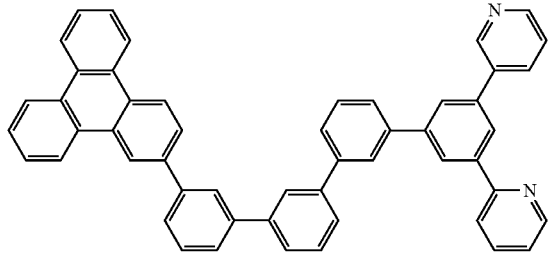
82
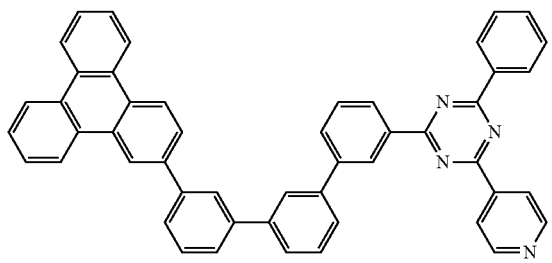

97
-continued
83
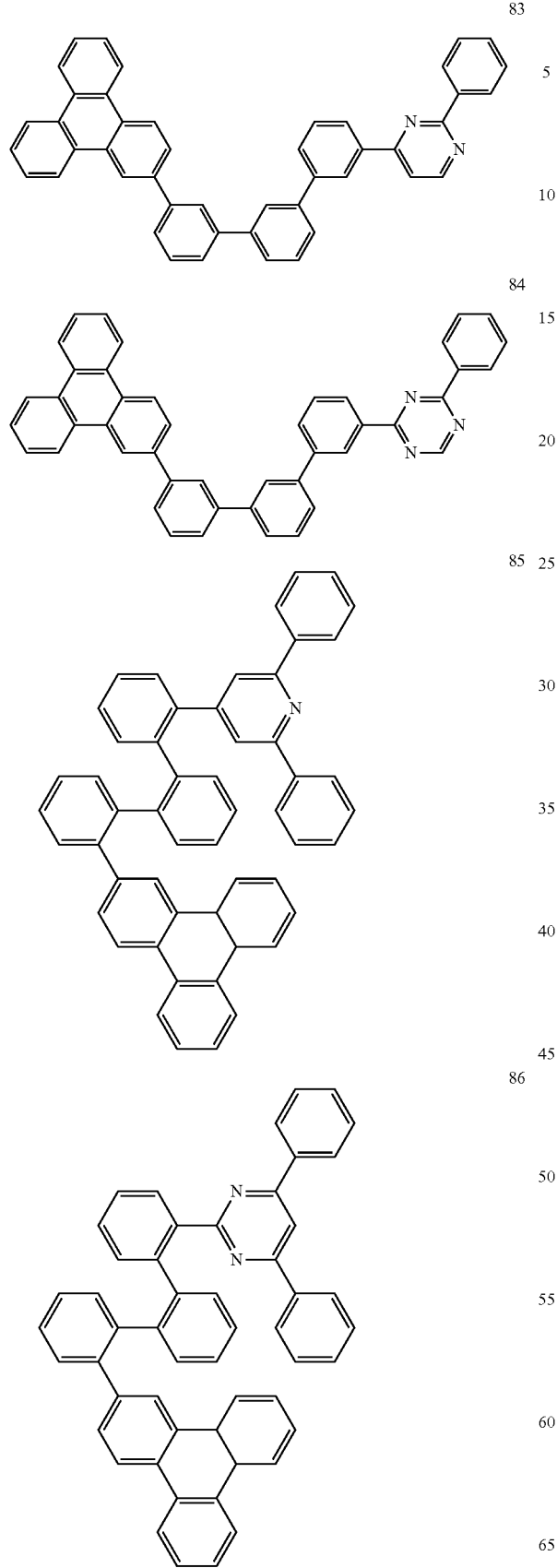
84
85
86
98
-continued
87
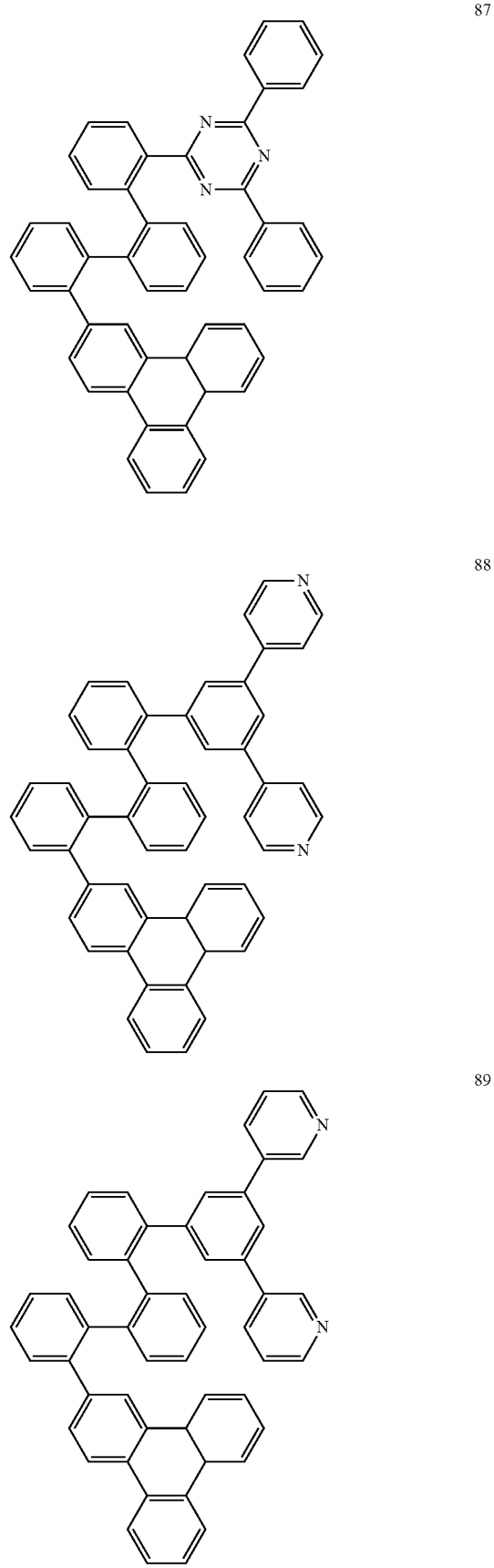
88
89

99
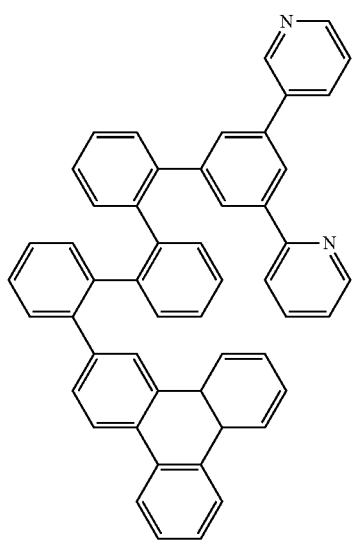
90
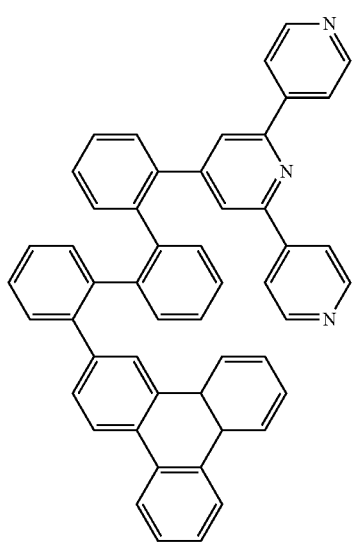
91
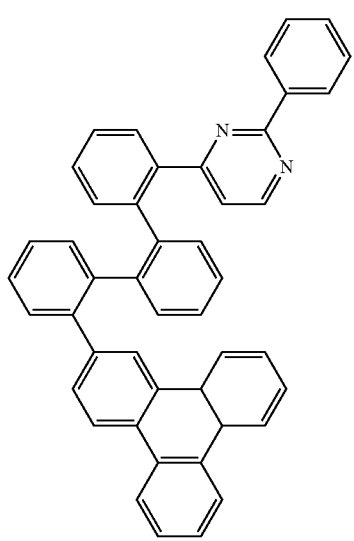
92
100
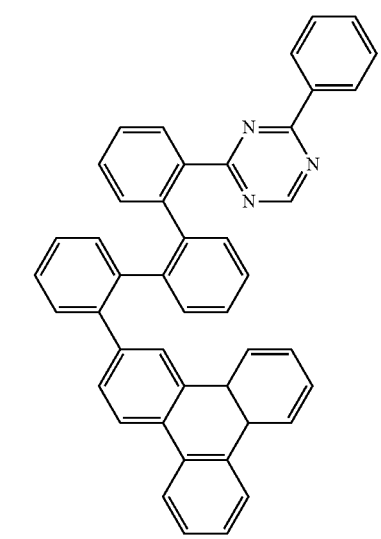
93
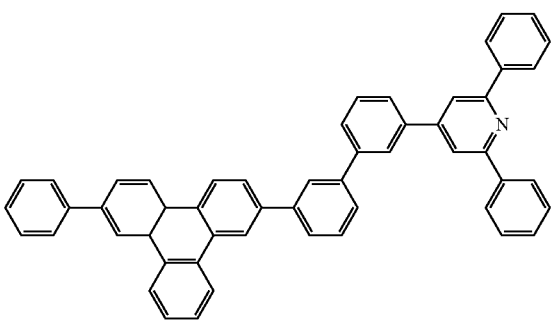
94
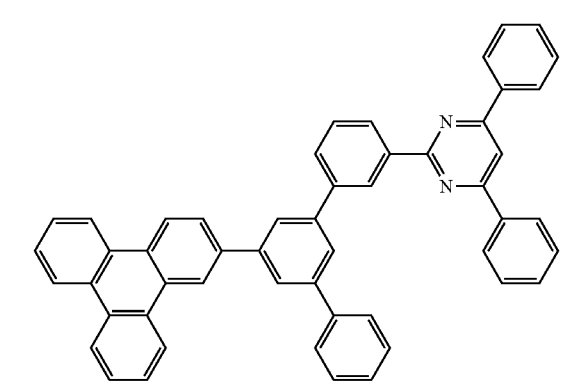
95
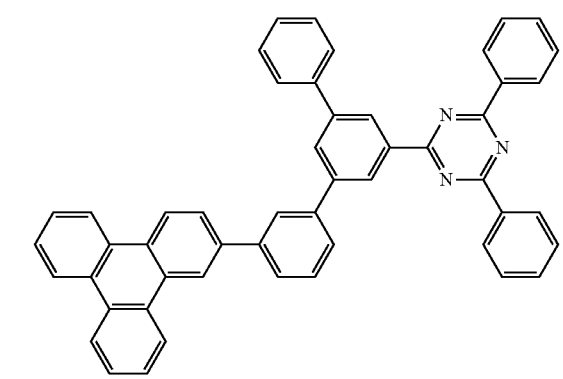
96

101
-continued

97

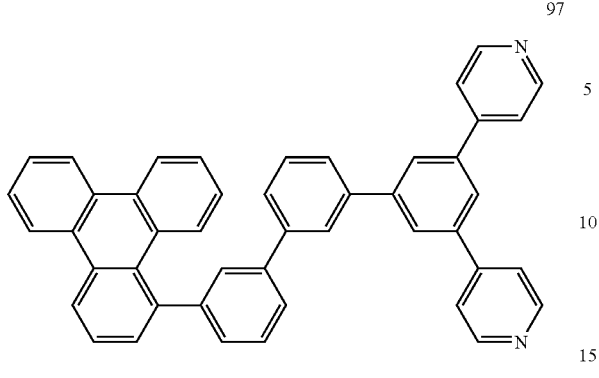

98

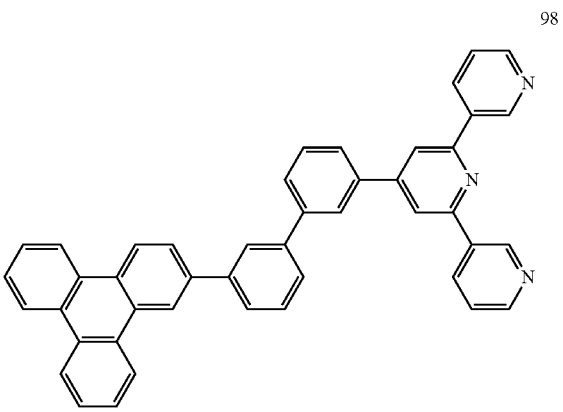

102
-continued

99

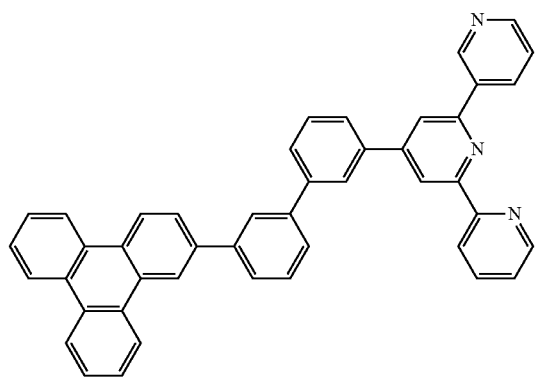

9. The luminescent material for an organic optoelectric device of claim 1, wherein the luminescent material has a LUMO energy of −2.0 to −2.5 eV.

10. An organic optoelectric device, comprising:
an anode and a cathode facing each other, and
an emission layer positioned between the anode and the cathode, the emission layer including the luminescent material according to claim 1.

11. The organic optoelectric device of claim 10, wherein:
the luminescent material is a host of the emission layer, and
the emission layer further includes a dopant.

12. The organic optoelectric device of claim 10, further comprising at least one auxiliary layer selected from a hole injection layer, a hole transport layer, an electron blocking layer, an electron transport layer, an electron injection layer, and a hole blocking layer.

13. A display device comprising the organic optoelectric device according to claim 10.

* * * * *